United States Patent
Giovannini et al.

(10) Patent No.: US 8,410,100 B2
(45) Date of Patent: Apr. 2, 2013

(54) PTERIDINONE DERIVATIVES AS PI3-KINASES INHIBITORS

(75) Inventors: Riccardo Giovannini, Verona (IT); Sara Frattini, Castelleone (IT); Trixi Brandl, Basel (CH); Steffen Breitfelder, Attenweiler (DE); Enzo Cereda, Novi Ligure (IT); Matthias Grauert, Biberach (DE); Matthias Hoffman, Mittelbiberach (DE); Anne T. Joergensen, Copenhagen (DK); Udo Maier, Senden (DE); Alexander Pautsch, Ulm (DE); Monica Quai, Milan (IT); Stefan Scheuerer, Warthausen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 68 days.

(21) Appl. No.: 12/524,791

(22) PCT Filed: Jan. 28, 2008

(86) PCT No.: PCT/EP2008/050986
§ 371 (c)(1),
(2), (4) Date: Nov. 5, 2009

(87) PCT Pub. No.: WO2008/092831
PCT Pub. Date: Aug. 7, 2008

(65) Prior Publication Data
US 2010/0099680 A1    Apr. 22, 2010

(30) Foreign Application Priority Data
Feb. 1, 2007 (EP) .................................. 07101544

(51) Int. Cl.
*A61K 31/50* (2006.01)
*A61K 31/525* (2006.01)

(52) U.S. Cl. ...................................................... 514/249

(58) Field of Classification Search .................... 514/249
See application file for complete search history.

(56) References Cited

U.S. PATENT DOCUMENTS 7,332,491 B2 * 2/2008 Grauert et al. ................ 514/250

FOREIGN PATENT DOCUMENTS

| CA | 2458699 | * | 3/2003 |
| CA | 2 517 020 | A1 | 9/2004 |
| CA | 2578838 | * | 3/2006 |
| WO | 01/19825 | A1 | 3/2001 |
| WO | WO 03/020722 | * | 3/2003 |
| WO | 2004/029055 | A1 | 4/2004 |
| WO | 2004/076454 | A1 | 9/2004 |
| WO | 2005/113556 | A1 | 12/2005 |
| WO | WO 2006/021378 | * | 3/2006 |
| WO | 2006/091737 | A1 | 8/2006 |

OTHER PUBLICATIONS

Anderson (Chem and Biol 10:787-797, 2003).*
Thiel (Nature Biotechnol 2:513-519, 2004).*
Palanki et al (J Med Chem 50:4279-4294, 2007).*
International Search Report for PCT/EP2008/050986 mailed Mar. 14, 2008.

* cited by examiner

*Primary Examiner* — Craig Ricci
(74) *Attorney, Agent, or Firm* — Michael P. Morris; Edward S. Lazer

(57) ABSTRACT

New compounds of Formula (1) are provided which by virtue of their pharmaceutical activity as PI3-kinase modulators may be used in the therapeutic field for the treatment of inflammatory or allergic diseases. Examples of these include inflammatory and allergic respiratory complaints, inflammatory diseases of the gastro-intestinal tract and motor apparatus, inflammatory and allergic skin diseases, inflammatory eye diseases, diseases of the nasal mucosa, inflammatory or allergic conditions involving autoimmune reactions or inflammations of the kidney.

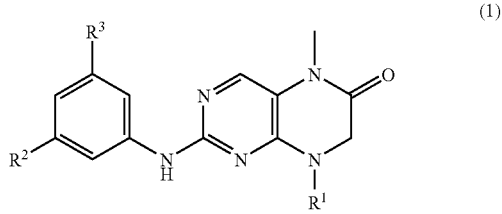

(1)

6 Claims, No Drawings

PTERIDINONE DERIVATIVES AS PI3-KINASES INHIBITORS

This application is the national phase entry under 35 U.S.C. §371 of International Application No. PCT/EP2008/050986, filed Jan. 28, 2008, which claims priority to European Patent Application No. 07101544.0, filed Feb. 1, 2007, each of which is hereby incorporated by reference in its entirety.

TECHNICAL FIELD

Phosphatidylinositol-3-kinases (PI3-kinases) are a subfamily of the lipid kinases which catalyse the transfer of a phosphate group to the 3'-position of the inositol ring of phosphoinositides (Vanhaesebroeck and Waterfield, Exp Cell Res. 1999 Nov. 25; 253(1):239-54).

They have an important role in numerous cell processes such as e.g. cell growth and differentiation processes, the control of cytoskeletal changes and the regulation of intracellular transport processes (Vanhaesebroeck et al., Annu Rev Biochem. 2001; 70:535-602). In view of their in vitro specificity for particular phosphoinositide substrates the PI3-kinases may be divided into different classes. The members of the receptor-regulated class I are heterodimeric enzymes which consist of a catalytic subunit (p110) weighing 110-120 kDa and a non-catalytic subunit (p50, p55, p85, p101) weighing 50-101 kDa. The most highly conserved region in all the PI3-kinases is the C-terminally situated kinase domain. It has structural features which can also be found in the majority of known protein kinases. These also include e.g. highly conserved amino acids which are responsible for the coordination of the ATP molecule (Walker et al., Nature. 1999 Nov. 18; 402(6759):313-20).

Three of the four members of the class I PI3-kinases associate constitutively with an adaptor subunit weighing 50-85 kDa, of which p85 is the prototype. The interaction takes place via the so-called p85 binding domain which can be found on the catalytic subunits of the PI3-kinase α, β and δ. The three forms are grouped in class IA on account of this structural feature. The catalytic subunit γ of the PI3-kinase, p110γ, associates instead with regulatory proteins weighing 101 or 84 kDa, which are known as p101 and p84. This structural division into class IA and IB also shows parallels in the functional properties of the corresponding PI3-kinase isoforms (Vanhaesebroeck and Waterfield, Exp Cell Res. 1999 Nov. 25; 253(1):239-54)

Thus, the PI3-kinase α, β and δ are activated predominantly by receptor-tyrosine-kinases (RTKs) or soluble tyrosine kinases. The p85-subunit serves as an adaptor, as it is able to recognise and bind the phosphorylated tyrosine groups of specific amino acid sequences (YxxM) with its SH2 domains. The PI3Kγ on the other hand is activated mainly by Gβγ-subunits which are released from heterotrimeric G-proteins after activation of heptahelical receptors. This differing coupling to cell surface receptors combined with a more or less restrictive expression necessarily results in very different tasks and functions for the 4 class I PI3-kinases in the intact organism (Wymann et al., Trends Pharmacol Sci. 2003 July; 24(7):366-76).

A number of independent findings indicate that class IA PI3-kinases are involved in uncontrolled cell growth and differentiation processes. Thus, the first detected PI3-kinase activity was associated with the transforming activity of viral oncogenes, such as e.g. the middle T antigen of polyomaviruses, Src tyrosine kinases or activated growth factors (Workman, Biochem Soc Trans. 2004 April; 32(Pt 2):393-6). In many tumours, such as e.g. breast cancer, ovarian or pancreatic carcinoma, there is found to be an overactivity of Akt/PKB, which is activated directly by the lipid products of class I PI3-kinases and thus transmits the signals on into the cell. Moreover, it was found just recently that the PIK3CA-gene which codes for p110α has a high mutation frequency in various types of tumour, such as colon, breast or lung carcinomas, some examples of which were able to be characterised as activating mutations (Samuels et al., Science. 2004 Apr. 23; 304(5670):554).

The most recent member of the class IA PI3-kinases, PI3Kδ, is expressed more restrictively than PI3Kα and β. In so-called "knock-in" mice in which the catalytic subunit of PI3Kδ, p110δ, had been replaced by an inactive mutant, it was demonstrated that this PI3K-isoenzyme plays a specific part in the signal transduction of B- and T-lymphocytes after antigen receptor stimulation (Okkenhaug et al., Science. 2002 August; 297(5583):1031-4). These are mechanisms which play a part especially in autoimmune diseases such as e.g. Crohn's disease or rheumatoid arthritis.

The PI3Kγ is activated almost exclusively by $G_i$-coupling heptahelical receptors. Thus, in neutrophils in mice which express no PI3Kγ, no PI3,4,5-$P_3$ formation was observed if they were stimulated with IL-8, fMLP, $LTB_4$ or C5a (Hirsch et al., to Science. 2000 Feb. 11; 287(5455):1049-53). This shows that at least in this type of cells PI3Kγ is the only PI3-kinase isoform which couples to heptahelical receptors. Moreover, isolated neutrophils and macrophages from the PI3Kγ-deficient mice exhibited a significantly reduced chemotactic activity or production of oxygen radicals elicited by a variety of chemokines and chemoattractors. Also reduced was the IgE-mediated activation of mast cells which had been isolated from p110γ-deficient mice. There has been some discussion that the mechanism responsible might be a positive feedback mechanism in which the PI3Kγ is activated by $G_i$-coupling adenosine $A_3$ receptors (Laffargue et al., Immunity. 2002 March; 16(3):441-51).

In spite of this decreased ability to react to inflammation mediators, the p110γ-deficient mice have normal viability and reproductive powers and have the same life expectancy as wild-type comparison animals reared identically. From this it can be concluded that the class IB PI3Kγ plays a central role in the activation of various inflammatory cells, and therefore isoform-specific inhibitors represent an attractive possibility for anti-inflammatory therapy with comparatively minor side effects (Ward and Finan, Curr Opin Pharmacol. 2003 August; 3(4):426-34). Apart from its function in leukocytes PI3Kγ also appears to be involved in the cardiovascular system, despite its low expression in cardiomyocytes. Thus, p110γ-deficient mice exhibited an increase in cardiac muscle contractility which may presumably be explained by an overproduction of cAMP (Crackower et al., Cell. 2002 Sep. 20; 110(6):737-49). It has only recently been possible to demonstrate that PI3Kγ is also involved in the development of cardiac hypertrophy. Thus, p110γ-deficient mice exhibited significantly reduced hypertrophy and fibrosis compared with wild-type animals in an isoproterenol-induced cardiac insufficiency model (Oudit et al., Circulation. 2003 Oct. 28; 108 (17):2147-52).

The problem of the present invention was to provide new compounds which by virtue of their pharmaceutical efficacy as PI3-kinase modulators may be used in the therapeutic field for the treatment of inflammatory or allergic diseases. Examples which may be mentioned here include inflammatory and allergic respiratory complaints, inflammatory diseases of the gastro-intestinal tract, rheumatoid arthritis, inflammatory and allergic skin diseases, inflammatory eye diseases, diseases of the nasal mucosa, inflammatory or allergic conditions involving autoimmune reactions, or inflammation of the kidneys.

PRIOR ART

PI3-kinase inhibitors for the treatment of inflammatory diseases are known in the literature. Thus, WO 03/072557 discloses 5-phenylthiazole derivatives, WO 04/029055 discloses annelated azolepyrimidines and WO 04/007491 discloses azolidinone-vinyl linked benzene derivatives. Pteridinone derivatives are known from the prior art as active substances with an antiproliferative activity. WO 04/076454 and WO 03/020722 describe the use of pteridinone derivatives for the treatment of cancer, infections, inflammatory and autoimmune diseases.

DETAILED DESCRIPTION OF THE INVENTION

Surprisingly it has been found that the above-mentioned problems are solved by compounds of formula 1. Accordingly, the present invention relates to compounds of formula 1,

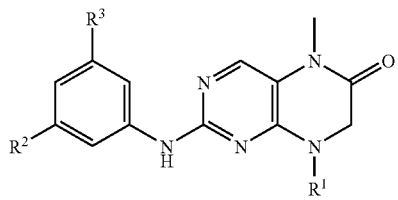

wherein
$R^1$ denotes an optionally substituted group selected from among $C_1$-$C_6$-alkyl, $C_{3\text{-}6}$-cycloalkyl, $C_{6\text{-}14}$-aryl, $C_{3\text{-}8}$-heterocycloalkyl and $C_{5\text{-}10}$-heteroaryl,
$R^2$ denotes
  hydrogen, hal or
  a group selected from among $C_{6\text{-}14}$-aryl, $C_{5\text{-}10}$-heteroaryl, -Q-CO—$NR^4$—$C_{6\text{-}14}$-aryl-$Z^1$—$R^5$, -Q-CO—$NR^4$—$C_{5\text{-}10}$-heteroaryl-$Z^1$—$R^5$, -Q-CO—$NR^4$—$Z^1$—$R^5$, -Q-$NR^4$—CO—$Z^1$—$R^5$, -Q-$NR^4$—CO—X—$R^6$, -Q-$NR^4$—$SO_2$—X—$R^7$, -Q-$NR^4$—$SO_2$—$Z^1$—$R^7$, -Q-$NR^4$—$Z^1$—$R^8$, —$Z^1$—$SO_2$—$R^{16}$, —$SO_2$—$Z^1$—$R^{16}$, CN, $CF_3$, $NO_2$, —COOH, —O—$C_{1\text{-}3}$-alkyl, —$Z^1$—OH, OH and $CONR^4R^8$,
or
a group selected from among formula (I), (II), (III), (IV), (V), (VI) and (VII)

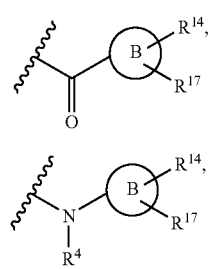

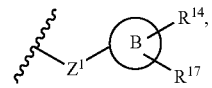

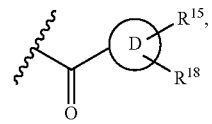

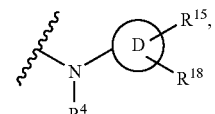

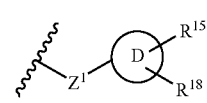

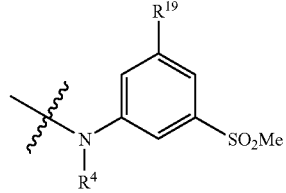

wherein
  X denotes a bond or O,
  $Z^1$ denotes a bond or $C_{1\text{-}4}$-alkylene optionally substituted by $NH_2$ or $C_{1\text{-}6}$-alkyl,
  Q denotes a bond or $C_{1\text{-}6}$-alkyl
  $R^4$ denotes H or $C_{1\text{-}3}$-alkyl,
  $R^5$ denotes $NR^4R^8$,
  or
  an optionally substituted group selected from among $C_{1\text{-}3}$-alkyl, $C_{3\text{-}6}$-cycloalkyl, $C_{6\text{-}14}$-aryl, $C_{3\text{-}8}$-heterocycloalkyl and $C_{5\text{-}10}$-heteroaryl,
  or
  an optionally substituted group of formula (X)

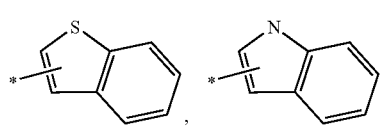

$R^6$ denotes an optionally substituted group selected from among $C_{1\text{-}5}$-alkyl, $C_{3\text{-}6}$-cycloalkyl, $C_{6\text{-}14}$-aryl, $C_{3\text{-}8}$-heterocycloalkyl and $C_{5\text{-}10}$-heteroaryl and benzyl,
$R^7$ denotes an optionally substituted group selected from among $C_{1\text{-}3}$-alkyl, $C_{3\text{-}6}$-cycloalkyl, $C_{6\text{-}14}$-aryl and $C_{5\text{-}10}$-heteroaryl,
$R^8$ denotes H, —$COCH_3$,
  or an optionally substituted group selected from among $C_{3\text{-}6}$-cycloalkyl, benzyl, $C_{3\text{-}8}$-heterocycloalkyl, $C_{6\text{-}14}$-aryl, $C_{5\text{-}10}$-heteroaryl, and $C_{1\text{-}4}$-alkyl
$R^{14}$, $R^{17}$ which may be identical or different, denote H or a group selected from among $C_{1\text{-}3}$-alkyl, $C_{3\text{-}6}$-cycloalkyl, $C_{6\text{-}14}$-aryl, $C_{5\text{-}10}$-heteroaryl, —CO—$C_{1\text{-}4}$-alkyl, —CO—$NR^4R^8$, —$NR^4R^8$, =O, $CH^2OH$, $CH^2NH_2$, CHF and COOH or $R^{14}$, $R^{17}$ form an optionally substituted 5- to 6-membered heterocyclic ring, containing up to two heteroatoms selected from among O, N and S.

$R^{15}$, $R^{18}$ which may be identical or different, denote H or a group selected from among $C_{1-3}$-alkyl, $C_{3-6}$-cycloalkyl, $C_{6-14}$-aryl, $C_{5-10}$-heteroaryl, —CO—$C_{1-4}$-alkyl, —CO—$NR^4R^8$, —$NR^4R^8$, =O, $CH^2OH$, $CH^2NH_2$, CHF and COOH or $R^{15}$, $R^{18}$ form an optionally substituted 5- to 6-membered heterocyclic ring, containing up to two heteroatoms selected from among O, N and S.

$R^{16}$ denotes H, OH, $NR^4R^8$, or an optionally substituted group selected from among $C_{1-3}$-alkyl, $C_{3-6}$-cycloalkyl, $C_{6-14}$-aryl, $C_{3-8}$-heterocycloalkyl and $C_{5-10}$-heteroaryl B denotes $C_{3-8}$-heterocycloalkyl or $C_{3-6}$-cycloalkyl D denotes $C_{5-10}$-heteroaryl or $C_{6-14}$-aryl, or $R^2$ denotes a group of formula (VIII) or (IX)

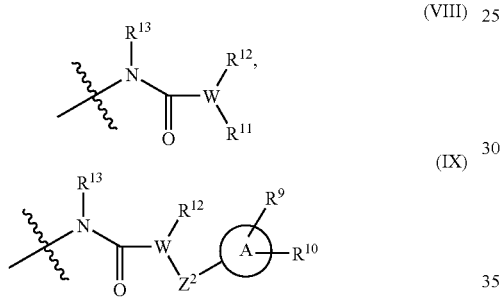

wherein

A denotes a group selected from among $C_{3-6}$-cycloalkyl, $C_{6-14}$-aryl, $C_{3-8}$-heterocycloalkyl and $C_{5-10}$-heteroaryl, W denotes N, C or O, $Z^2$ denotes a bond or $C_1$-$C_4$-alkylene;

$R^9$, $R^{10}$ denote H, hal or a group selected from among $C_{1-3}$-alkyl, $NR^4R^8$, =O, —$C_{1-2}$-alkylene-phenyl, —$NR^4$—$C_{1-2}$-alkylene-phenyl, —COO—$C_{1-5}$-alkyl, —CO-phenyl, —CO—$C_{1-5}$-alkyl, —CO—$Z^2$—$C_{3-6}$-cycloalkyl, $C_{6-14}$-aryl, $C_{5-10}$-heteroaryl, $C_{3-6}$-cycloalkyl and optionally substituted $C_{5-8}$-heterocycloalkyl $R^{11}$ denotes H, $C_{1-3}$-alkyl, $R^{12}$ denotes H, $C_{1-4}$-alkyl, —$Z^2$—$NR^4R^8$ or —$Z^2$—O—$C_{1-3}$-alkyl, or $R^{11}$ and $R^{12}$ form an optionally substituted N-containing 5- to 6-membered heterocyclic ring, $R^{13}$ denotes H or $C_{1-3}$-alkyl, or $R^{13}$ and $R^{12}$ form a N-containing 5- to 6-membered heterocyclic ring, $R^3$ denotes H, hal or a group selected from among $SO_2R^4$, $SO_2NHR_4$; —$CH_2SO_2R^4$; —$CH_2SO_2NR^5R^6$, $CONH_2$, CONHMe; $NHSO_2Me$, COOH, $CH_2OH$, CN, $NO_2$, $NH_2$, $CF_3$, OH and OMe;

and the pharmaceutically acceptable salts, diastereomers, enantiomers, racemates, hydrates or solvates thereof.

Preferred compounds of formula 1 mentioned above are those wherein at least one of $R^2$ or $R^3$ denotes a group selected from among —$NR^4$—$SO_2$—X—$R^7$, —$NR^4$—$SO_2$—$Z^1$—$R^7$, —$Z^1$—$SO_2$—$R^{16}$ and —$SO_2$—$Z^1$—$R^{16}$.

Preferred compounds of formula 1 mentioned above are those wherein at least one of $R^9$ or $R^{10}$ denotes hydrogen.

Particularly preferred compounds of formula 1 mentioned above are those wherein $R^1$ denotes $C_1$-$C_3$-alkyl, preferably propyl, most preferably isopropyl.

Particularly preferred compounds of formula 1 mentioned above are those wherein $R^2$ denotes a group selected from among CO—$NR^4$—$C_{6-14}$-aryl-$Z^1$—$R^5$, —CO—$NR^4$—$Z^1$—$R^5$, —$NR^4CO$—$Z^1$—$R^5$, —$NR^4$—CO—X—$R^6$, —$NR^4$—$SO_2$—$Z^1$—$R^7$, —$Z^1$—$SO_2$—$R^{16}$, $NO_2$ and $CONR^4R^8$, or a group of formula (III) or (IV)

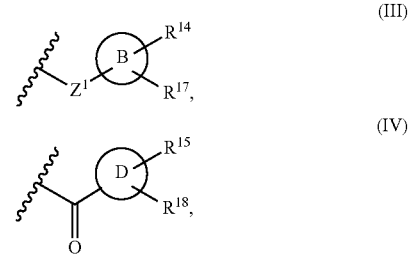

wherein

X denotes a bond or O, $Z^1$ denotes a bond or $C_{1-3}$-alkylene, $R^4$ denotes H, $R^5$ denotes $NR^4R^8$, or an optionally substituted group selected from among $C_{3-6}$-cycloalkyl, $C_{3-8}$-heterocycloalkyl and $C_{5-10}$-heteroaryl, or an optionally substituted group of formula (X)

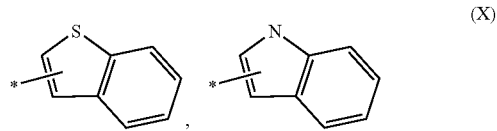

$R^6$ denotes $C_{1-5}$-alkyl, $R^7$ denotes an optionally substituted group selected from among $C_{1-3}$-alkyl, preferably methyl, and phenyl, $R^8$ denotes H, $R^{14}$, $R^{17}$ which may be identical or different, denote H, $C_{3-6}$-cycloalkyl or =O, $R^{15}$, $R^{18}$ which may be identical or different, denote H or COOH or $R^{16}$ denotes H or $C_{1-3}$-alkyl,
B denotes $C_{3-8}$-heterocycloalkyl
D denotes $C_{6-14}$-aryl,
or
$R^2$ denotes
  a group of formula (VIII) or (IX)

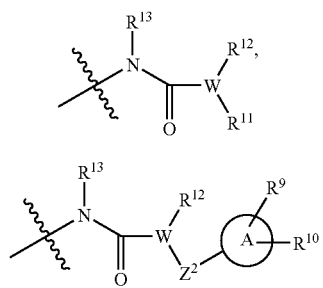

wherein
  A denotes a group selected from among $C_{3-6}$-cycloalkyl, preferably cyclohexyl, $C_{6-14}$-aryl, preferably phenyl, $C_{3-8}$-heterocycloalkyl, preferably N-containing 5- or 6-membered heterocycle, most preferably pyrrolidinyl, and $C_{5-10}$-heteroaryl, preferably N-containing 5- or 6-membered heteroaryl, most preferably pyridinyl and imidazolyl;
  W denotes N, C or O,
  $Z^2$ denotes a bond or $C_1$-$C_4$-alkylene;
  $R^9$, $R^{10}$ denote H, hal, or
    a group selected from among $C_{1-3}$-alkyl, $NR^4R^8$, =O, —$C_{1-2}$-alkylene-phenyl, —$NR^4$—$C_{1-2}$-alkylene-phenyl, —COO—$C_{1-5}$-alkyl, —CO-phenyl, —CO—$C_{1-5}$-alkyl, —CO—$Z^2$—$C_{3-6}$-cycloalkyl, $C_{6-14}$-aryl, $C_{5-10}$-heteroaryl, $C_{3-6}$-cycloalkyl and optionally substituted $C_{5-8}$-heterocycloalkyl
  $R^{11}$ denotes H, $C_{1-3}$-alkyl,
  $R^{12}$ denotes H, $C_{1-4}$-alkyl, —$Z^2$—$NR^4R^8$ or —$Z^2$—O—$C_{1-3}$-alkyl,
  or
  $R^{11}$ and $R^{12}$ form an optionally substituted N-containing 5- to 6-membered heterocyclic ring,
  $R^{13}$ denotes H or $C_{1-3}$-alkyl,
  or
  $R^{13}$ and $R^{12}$ form a N-containing 5- to 6-membered heterocyclic ring, Particularly preferred $R^2$ denotes a group of formula (VIII) or (IX).

In a preferred aspect the present invention relates to compounds of formula 1 as pharmaceutical compositions.

In a preferred aspect the present invention relates to the use of therapeutically effective amounts of the active substance 1 for preparing a pharmaceutical composition for the treatment of diseases whose pathology involves an activity of PI3-kinases, wherein therapeutically effective doses of the compounds of formula 1 may provide a therapeutic benefit.

Preferably, therapeutically effective amounts of a compound of formula 1 are used as specified above for preparing a pharmaceutical composition for the treatment of inflammatory and allergic diseases of the airways.

It is particularly preferable to use therapeutically effective amounts of a compound of formula 1 as specified above for preparing a pharmaceutical composition for the treatment of chronic bronchitis, acute bronchitis, bronchitis caused to by bacterial or viral infection or fungi or helminths, allergic bronchitis, toxic bronchitis, chronic obstructive bronchitis (COPD), asthma (intrinsic or allergic), pediatric asthma, bronchiectasis, allergic alveolitis, allergic or non-allergic rhinitis, chronic sinusitis, cystic fibrosis or mucoviscidosis, alpha-1-antitrypsin deficiency, cough, pulmonary emphysema, interstitial lung diseases, alveolitis, hyperreactive airways, nasal polyps, pulmonary oedema, pneumonitis of different origins, e.g. radiation-induced or caused by aspiration, or infectious pneumonitis, collagenoses such as lupus eryth, systemic sclerodermy, sarcoidosis and Boeck's disease.

It is also preferable to use therapeutically effective amounts of a compound of formula 1 as specified above for preparing a pharmaceutical composition for the treatment of diseases of the nasal mucosa.

In a preferred aspect the present invention relates to pharmaceutical formulations, characterised in that they contain one or more compounds of formula 1.

In a preferred aspect the present invention relates to pharmaceutical formulations for administration by inhalation, characterised in that it contains a compound of formula 1.

Terms and Definitions Used

In general, all tautomeric forms and isomeric forms and mixtures, whether individual geometric isomers or optical isomers or racemic or non-racemic mixtures of isomers, of a chemical structure or compound is intended, unless the specific stereochemistry or isomeric form is specifically indicated in the compound name or structure.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, to or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isothionic, and the like. (also see Pharmaceutical salts, Birge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remingto which release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional.

By the term "$C_{1-6}$-alkyl" (including those which are part of other groups) are meant branched and unbranched alkyl groups with 1 to 6 carbon atoms, and by the term "$C_{1-4}$-alkyl" are meant branched and unbranched alkyl groups with 1 to 4 carbon atoms. Alkyl groups with 1 to 4 carbon atoms are preferred. Examples of these include: methyl, ethyl, n-propyl, iso-propyl, n-butyl, iso-butyl, sec-butyl, tert-butyl, n-pentyl, iso-pentyl, neo-pentyl or hexyl. The abbreviations Me, Et, n-Pr, i-Pr, n-Bu, i-Bu, t-Bu, etc. may optionally also be used for the above-mentioned groups. Unless stated otherwise, the definitions propyl, butyl, pentyl and hexyl include all the possible isomeric forms of the groups in question. Thus, for example, propyl includes n-propyl and iso-propyl, butyl includes iso-butyl, sec-butyl and tert-butyl etc.

By the term "$C_{1-6}$-alkylene" (including those which are part of other groups) are meant branched and unbranched alkylene groups with 1 to 6 carbon atoms and by the term "$C_{1-4}$-alkylene" are meant branched and unbranched alkylene groups with 1 to 4 carbon atoms. Alkylene groups with 1 to 4 carbon atoms are preferred. Examples include: methylene, ethylene, propylene, 1-methylethylene, butylene, 1-methylpropylene, 1,1-dimethylethylene, 1,2-dimethylethylene, pentylene, 1,1-dimethylpropylene, 2,2-dimethylpropylene, 1,2-dimethylpropylene, 1,3-dimethylpropylene or hexylene. Unless stated otherwise, the definitions propylene, butylene, pentylene and hexylene also include all the possible isomeric forms of the relevant groups with the same number of carbons. Thus for example propyl also includes 1-methylethylene and butylene includes 1-methylpropylene, 1,1-dimethylethylene, 1,2-dimethylethylene.

By the term "$C_{3-8}$-cycloalkyl" (including those which are part of other groups) are meant cyclic alkyl groups with 3 to 8 carbon atoms, by the term "$C_{3-6}$-cycloalkyl" are meant cyclic alkyl groups with 3 to 8 carbon atoms and by the term "$C_{5-6}$-cycloalkyl" are meant cyclic alkyl groups with 5 to 6 carbon atoms. Examples include: cyclopropyl, cyclobutyl, cyclopentyl, cyclohexyl, cycloheptyl or cyclooctyl.

By the term "aryl" (including those which are part of other groups) are meant aromatic ring systems with 6 or 10 carbon atoms. Examples include: phenyl or naphthyl, the preferred aryl group being phenyl.

By the term "heterocyclic" are meant five-, six- or seven-membered, saturated or unsaturated heterocyclic rings or 5-10 membered, bicyclic heterorings which may contain one, two or three heteroatoms, selected from among oxygen, sulphur and nitrogen; the ring may be linked to the molecule by a carbon atom or, if present, by a nitrogen atom. The following are examples of five-, six- or seven-membered, saturated or unsaturated heterocyclic rings:

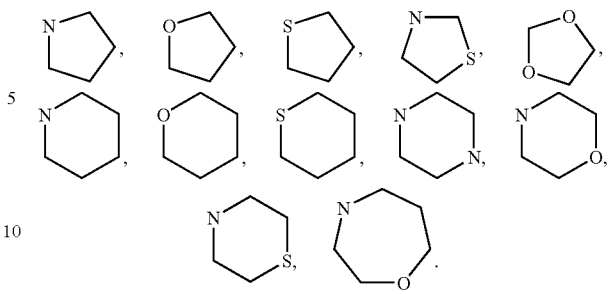

Unless stated otherwise, a heterocyclic ring may be provided with a keto group.

Examples Include:

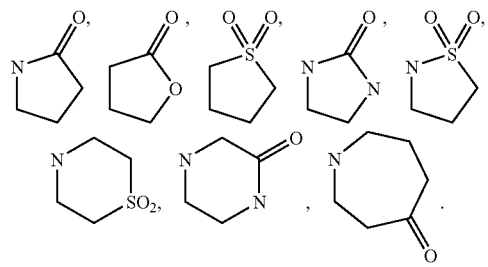

Examples of 5-10-membered bicyclic heterorings are pyrrolizine, indole, indolizine, to isoindole, indazole, purine, quinoline, isoquinoline, benzimidazole, benzofuran, benzopyran, benzothiazole, benzoisothiazole, pyridopyrimidine, pteridine, pyrimidopyrimidine,

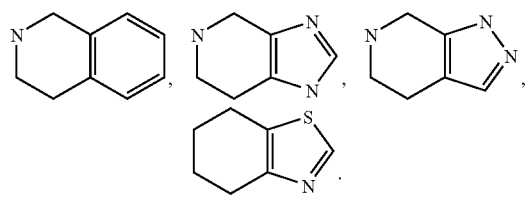

Although the term heterocyclic rings includes "heteroaryl", i.e. heterocyclic aromatic groups, the term heterocyclic aromatic groups denotes five- or six-membered heterocyclic aromatic groups or 5-10 membered, bicyclic heteroaryl rings which may contain one, two or three heteroatoms, selected from among oxygen, sulphur and nitrogen, which contain sufficient conjugated double bonds that an aromatic system is formed. The ring may be linked to the molecule through a carbon atom or if present through a nitrogen atom. The following are examples of five- or six-membered heterocyclic aromatic groups:

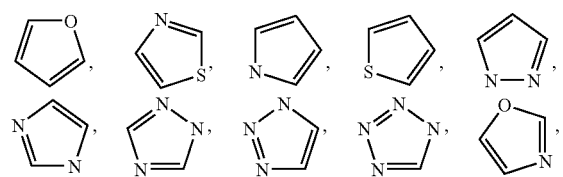

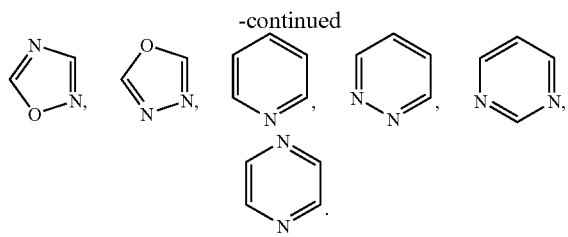

Examples of 5-10-membered bicyclic hetaryl rings include pyrrolizine, indole, indolizine, isoindole, indazole, purine, quinoline, isoquinoline, benzimidazole, benzofuran, benzopyran, benzothiazole, benzoisothiazole, pyridopyrimidine, pteridine, pyrimidopyrimidine.

By the term "optionally substituted" is meant within the scope of the invention the above-mentioned group, optionally substituted by a lower-molecular group. Examples of lower-molecular groups regarded as chemically meaningful are groups consisting of 1-200 atoms. Preferably such groups have no negative effect on the pharmacological efficacy of the compounds.

For example the groups may comprise:
Straight-chain or branched carbon chains, optionally interrupted by heteroatoms, optionally substituted by rings, heteroatoms or other common functional groups.
Aromatic or non-aromatic ring systems consisting of carbon atoms and optionally heteroatoms, which may in turn be substituted by functional groups.
A number of aromatic or non-aromatic ring systems consisting of carbon atoms and optionally heteroatoms which may be linked by one or more carbon chains, optionally interrupted by heteroatoms, optionally substituted by heteroatoms or other common functional groups.

Synthesis of the Reagents

Preparation of
3-(Methylsulfonyl)-5-trifluoromethyl-phenylamine

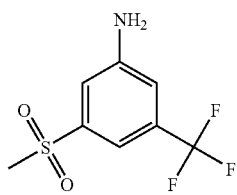

A suspension of sodium sulfite (3.0 g, 24 mmol), sodium bicarbonate (3.7 g; 44 mmol and 3-trifluormethylbenzenesulfonylchloride (5.0 g; 20 mmol) in 70 mL water, was heated at 75° C. for 1 hour. Then 5 mL 50% aqueous sodium hydroxide to solution and ethyl bromoacetic acid (2.65 mL; 22 mmol) was added and the mixture was refluxed for 30 hours. Then the mixture was extracted with dichloromethane and concentrated to provide 1 g (4.46 mmol; 20% yield) of 1-methanesulfonyl-3-trifluoromethylbenzene as a solid.

1-methanesulfonyl-3-trifluoromethylbenzene (220 mg; 1 mmol) was dissolved at 0° C. in 3 mL 98% sulfuric acid and 2 mL of 100% $HNO_3$ were added. The mixture was heated 2 hours at 80° C. and then poured onto ice; a precipitate was isolated: 110 mg (0.40 mmol; 40% yield) of 1-methanesulfonyl-3-nitro-5-trifluoromethylbenzene were obtained as a solid.

1-methanesulfonyl-3-nitro-5-trifluoromethylbenzene (500 mg; 1.9 mmol) was dissolved in 100 mL methanol, 70 mg of Pd/C (10%) was added and the mixture was hydrogenated at 3 bar. The reaction mixture was filtrated and solvent removed under reduced pressure. 250 mg (1.04 mmol; 55% yield) of a colorless solid were obtained.

Preparation of N-(3-Amino-5-trifluormethylphenyl)-methanesulfonamide

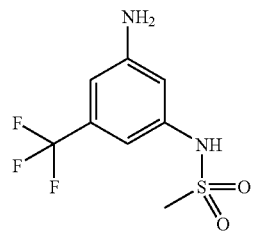 [SMILES: CS(=O)(=O)Nc1cc(N)cc(C(F)(F)F)c1]

3-Nitro-5-trifluoromethylaniline (0.8 g; 4 mmol) was suspended in pyridine (5 mL), methanesulfonylchloride (0.6 mL; 8 mmol) was added at 0° C. and the mixture stirred for 5 hours at room temperature. A solution of sodium bicarbonate was then added to the reaction mixture and the precipitate obtained was washed with diluted hydrochloric acid and dried. 0.6 g (2.11; 52.8% yield) of N-(3-nitro-5-trifluoromethyl-phenyl)-methylsulfonamide were obtained as solid.

N-(3-nitro-5-trifluoromethyl-phenyl)-methylsulfonamide (0.1 g; 0.4 mmol) ammonium formate (0.1 g; 1.8 mmol) and Raney-Nickel (16 mg) were dissolved in 0.4 mL of dioxane. The reaction was heated to 140° C. for 6 minutes in a micro wave reactor. The mixture was then diluted with dichloromethane, filtrated and the filtrate concentrated. 70 mg (0.27 mmol; 68% yield) of an orange oil were obtained.

Preparation of
3-(methylsulfonyl)methyl-5-trifluoromethyl-aniline

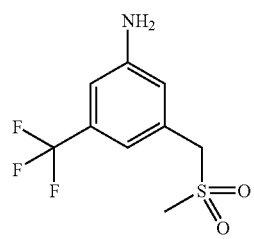 [SMILES: CS(=O)(=O)Cc1cc(N)cc(C(F)(F)F)c1]

Borane [1 M solution of in tetrahydrofuran (31.9 ml; 31.9 mmol)] was added dropwise to a cooled (0° C.) solution of 3-nitro-5-(trifluoromethyl)benzoic acid (5 g; 21.26 mmol) in THF (100 mL) under nitrogen atmosphere. The reaction mixture was allowed to reach room temperature and was maintained at that temperature overnight.

$NH_4Cl$ solution (50 ml) was then added slowly to the reaction mixture, the precipitate formed was filtered and the phases were separated. The organic phase was diluted with dichloromethane, filtered, dried over $MgSO_4$ and concentrated in vacuo. 4.36 g (19.71 mmol; 93% yield) of (3-nitro-5-trifluoromethyl-phenyl)-methanol as a colourless oil were obtained.

Thionyl chloride (0.99 ml; 13.56 mmol) was slowly added to a previously cooled (0° C.) solution of 3-nitro-5-trifluoromethyl-phenylmethanol (500 mg; 2.26 mmol) in 50 ml of dichloromethane. The reaction mixture was allowed to reach room temperature and was maintained at that temperature overnight.

The reaction mixture was concentrated in vacuo and 520 mg (2.170 mmol; 96% yield) of 1-chloromethyl-3-nitro-5-trifluoromethyl-benzene were obtained as yellow oil.

A solution of 1-chloromethyl-3-nitro-5-trifluoromethyl-benzene (520 mg; 2.170 mmol) and methanesulfinic acid sodium salt (664 mg; 6.511 mmol) in Methanol (10 ml) of was refluxed overnight. The reaction was then cooled to room temperature and the product precipitated was filtered and diluted with dichloromethane. The solid was removed and the organic phase was concentrated in vacuo 520 mg (2 mmol; 85% yield) of 1-methylsulfonylmethyl-3-nitro-5-trifluoromethyl-benzene were obtained.

A suspension of 1-methylsulfonylmethyl-3-nitro-5-trifluoromethyl-benzene (520 mg; 2.170 mmol) and 50 mg of Pd/C 10% in methanol (50 ml) was hydrogenated (1 bar) overnight. The reaction mixture was filtered on a celite pad and the obtained solution concentrated in vacuo. The crude was washed with dichloromethane in order to filter salts, coming from the previous reaction. 100 mg (0.395 mmol; 18% yield) were obtained.

Preparation of 3-amino-5-nitro-benzenesulfonamide

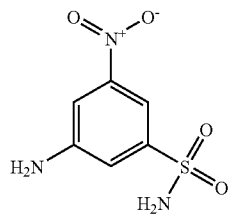 [SMILES: Nc1cc([N+](=O)[O-])cc(S(N)(=O)=O)c1]

20 ml of fuming nitric acid was added dropwise to 10 ml of cooled oleum 65% solution. 3-nitrobenzenesulfonic acid sodium salt (5 g; 22.2 mmol) was added in portions to the cooled sulfonitric mixture (500 mg portions). The reaction mixture was allowed to reach room temperature and then warmed to 120° C. for 1 h.

Then, the reaction was cooled to 0° C. and Ca(OH)$_2$ was added in small portions. After the neutralisation CaSO$_4$ formed was filtered and the aqueous solution concentrated in vacuo. 5 g (20 mmol; 91% yield) of 3,5-dinitro-benzenesulfonic acid were obtained as an orange powder.

3,5-dinitro-benzenesulfonic acid (15 g; 60.44 mmol), phosphorus pentachloride (37 g; 181 mmol) in phosphorus oxychloride (350 ml) were refluxed overnight. The reaction mixture was concentrated in vacuo. The residue was immediately diluted with 100 ml of 1,4-dioxane, cooled to 0° C. and ammonium hydroxide [(30%), 50 ml] was added dropwise. The reaction mixture was allowed to reach room temperature and maintained to that temperature for 1 h. Then, it was concentrated in vacuo. The crude was precipitated with water and the precipitate was filtered and dried in vacuo. 6 g (24 mmol; 43% yield) of 3,5-dinitro-benzenesulfonamide were obtained.

A suspension of sodium hydrogensulfide hydrate (3.88 g; 49 mmol) in Methanol (200 ml) was added to a solution of 3,5-dinitro-benzenesulfonamide (6 g; 24.27 mmol) in Methanol (500 ml). The reaction mixture was refluxed for 3 h then cooled to room temperature, filtered and concentrated in vacuo. The crude was washed with water, filtered and dried in vacuo. 3.2 g (15 mmol; 61% yield) of orange powder were obtained.

Preparation of
3-Amino-5-(methylsulfonyl)amino-benzoic acid
methyl ester

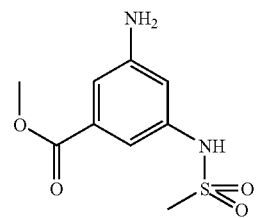 [SMILES: COC(=O)c1cc(N)cc(NS(C)(=O)=O)c1]

3-amino-5-nitro-benzoic acid (25 g; 0.14 mol) in 250 ml methanolic hydrogen chloride solution was heated at 70° C. for 3 hours. The mixture was concentrated in vacuo, diluted in ethyl acetate, washed with NaHCO$_3$ solution and the organic phase concentrated. 25 g (0.13 mmol; 91% yield) of 3-amino-5-nitro-benzoic acid methyl ester were obtained, as a yellow solid.

3-amino-5-nitro-benzoic acid methyl ester (25 g; 0.13 mol) was dissolved in to dichloromethane (300 ml) and treated at 0° C. with 11 ml of pyridine. Methanesulfonylchloride (11 ml; 0.14 mol) was added and the reaction mixture was stirred overnight at room temperature. Water was added and the precipitate filtered and washed with dichloromethane/diethylether. 32 g (0.11 mmol; 89% yield) of 3-methylsulfonylamino-5-nitro-benzoic acid methyl ester were obtained as a solid.

3-methylsulfonylamino-5-nitro-benzoic acid methyl ester (32 g; 0.12 mol) was suspended in methanol (500 ml), 4 g (5% w/w; 4 g) was added and the mixture was hydrogenated at 4-5 bar. The reaction mixture was subsequently filtered on a Celite pad and the filtrate concentrated. 23 g (0.08 mmol; 66% yield) of a yellow powder were obtained.

Preparation of N-(3-Amino-5-(methylsulfonyl)-phenyl)-methylsulfonamide

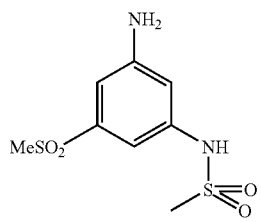

3-methylsulfonyl-5-nitro-aniline (0.26 g; 1.2 mmol) was dissolved in pyridine (10 ml). A solution of methanesulfonylchloride (0.2 mL; 2.4 mmol) in 2 mL of pyridine was added and the reaction mixture was stirred for 12 hours at ambient temperature. NaHCO$_3$ solution was added and the mixture extracted with dichloromethane. The aqueous phase was acidified and extracted with ethyl acetate. The organic phase was dried and concentrated. 0.12 g (0.5 mmol; 43% yield) of N-(3-methyl-5-nitro-phenyl)-methylsulfonamide were obtained as a yellow solid.

A mixture of N-(3-methyl-5-nitro-phenyl)-methylsulfonamide (0.12 g; 0.4 mmol), ammonium formate (0.26 g; 4 mmol) and Raney-Nickel in 1 mL dioxane was heated at 120° C. in a microwave oven for 20 minutes. The mixture was then filtrated on a celite pad and concentrated. 70 mg (0.35 mmol; 87% yield) of a red oil were obtained.

Preparation of 3-Bromo-5-(methylsulfonyl)-aniline

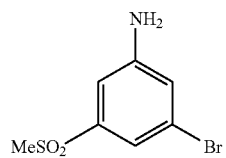

A solution of NaNO$_2$ (0.2 g; 3 mmol) in water (1 ml) was added at 0° C. to a solution of 3-(methylsulfonyl)-5-nitroaniline (0.4 g; 2 mmol) in concentrated HBr (5 ml). After 30 minutes, a solution of Cu(I)-bromide (0.4 g; 3 mmol) in concentrated HBr (5 ml) was added. The mixture was slowly warmed to room temperature and stirred for 16 hours at room temperature. Ethyl acetate and ice water were added. The organic phase was separated, dried and concentrated.

The crude was purified by flash chromatography (hexane/ethyl acetate). 100 mg (0.46 mmol; 15% yield) of 1-Bromo-3-methylsulfonyl-5-nitro-benzene were obtained as a yellow solid.

1-Bromo-3-methylsulfonyl-5-nitro-benzene (100 mg; 0.4 mmol) was dissolved in THF (10 ml). Raney-Nickel was added and the mixture hydrogenated at 1 bar. The reaction mixture was filtrated and concentrated. 30 mg (0.16 mmol; 40%) of target compound were obtained as a yellow solid.

Preparation of 3-Chloro-5-(methylsulfonyl)-aniline

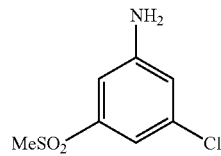

3-Chlor-5-(methylsulfonyl)-aniline was synthesized in analogy to 3-Bromo-5-(methylsulfonyl)-aniline.

Preparation of (3-Amino-5-methanesulfonyl-phenyl)-methanol

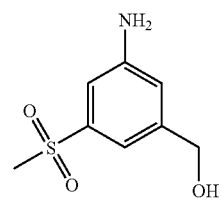

3-Amino-5-(methylsulfonyl)-benzoic acid ethyl ester (100 mg; 0.4 mmol) was dissolved in THF (4 ml), treated with lithium aluminiumhydride (33 mg; 0.9 mmol) and stirred for 18 hours at room temperature. The reaction mixture was treated in sequence with ethyl acetate (4 ml), water (0.5 ml), hydrochloric acid (5% solution in water; 0.5 ml) and a saturated aqueous ammoniumchloride solution (1.5 ml). The aqueous phase was extracted with dichloromethane and the organic phase was filtrated on a silica pad then dried and concentrated. 55 mg (0.27 mmol; 68% yield) of an orange oil were obtained.

Preparation of 3-(Methylsulfonyl)-5-methoxy-aniline

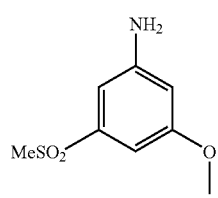

Methylphenylsulfone (5.0 g; 32 mmol) was added to an ice cold solution of 10 mL of fuming HNO$_3$ and 65% oleum. The mixture was slowly heated to 140° C. and stirred for 6 hours. After cooling to room temperature, the mixture was poured onto to ice and the precipitate filtered and washed with diisopropylether. 5.5 g (22.3 mmol; 70% yield) of 1-methylsulfonyl-3,5-dinitro-benzene were obtained as a colorless solid.

To a solution of 1-methylsulfonyl-3,5-dinitro-benzene (2.0 g; 8 mmol) in methanol (15 ml) a solution of sodium methoxide (0.5 g; 10 mmol) in methanol (5 ml) was added. The mixture was refluxed for 2 hours. Water was added and the precipitate washed with a diisopropylether/ethanol mixture. 1.3 g (5.62 mmol; 70% yield) of 1-methylsulfonyl-3-methoxy-5-nitro-benzene were obtained as a yellow solid.

1-Methylsulfonyl-3-methoxy-5-nitro-benzene (1.3 g; 5.6 mmol) was dissolved in methanol (40 ml) and 80 mg Pd/C (5% w/w) were added and the reaction mixture was hydrogenated at 2 bar. The mixture was then diluted with dichloromethane, filtrated above over a celite pad, concentrated and the residual was crystallized from methanol. 0.5 g (2.48 mmol; 44% yield) of a solid were obtained.

Preparation of 3-(Methylsulfonyl)-5-nitro-aniline

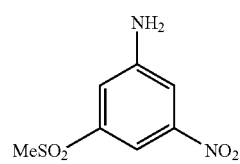

A solution of 1-(methylsulfonyl)-3,5-dinitro-benzene (1 g; 4 mmol) in methanol (80 ml) and toluene (20 ml) was treated with a solution of sodium hydrogensulfide-hydrate (227 mg; 4 mmol) in 20 ml methanol. The mixture was then refluxed for 3 hours additional 500 mg sodium hydrogensulfide-hydrate were added and refluxed for an additional hour. After cooling, the precipitate was filtrated and the filtrate concentrated. The residual was crystallized from methanol. 500 mg (2.31 mmol; 57% yield) of a yellow solid were obtained.

Preparation of 3-amino-5-(methylsulfonyl)-benzoic acid methyl ester

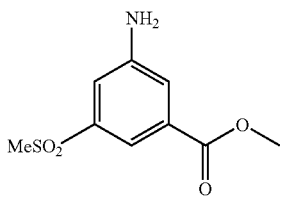

To a suspension of 3-(methylsulfonyl)-benzoic acid (32.5 g; 0.16 mol) in 130 mL 98% sulphuric acid at 0° C. was slowly added potassium nitrate (32.8 g; 0.32 mol). The reaction mixture was heated for 3 hours at 110° C., subsequently cooled to room temperature and poured onto ice and the precipitate collected. 28 g (0.114 mmol; 71% yield) of 3-(methylsulfonyl)-5-nitro-benzoic acid were obtained as a solid.

3-(methylsulfonyl)-5-nitro-benzoic acid methyl ester (34 g; 0.14 mol) was dissolved in 350 mL of methanol, 10 ml of 98% sulfuric acid were added and the mixture refluxed for 10 hours. After cooling the precipitate was filtered and washed with methanol. Concentrating the filtrate yields further material. 32 g (0.12 mmol; 88% yield) of 3-(methylsulfonyl)-5-nitro-benzoic acid methyl ester were obtained as a colorless solid.

3-(Methylsulfonyl)-5-nitro-benzoic acid methyl ester (32 g; 0.12 mol) was dissolved in methanol (300 ml), 4 g Pd/C (5%) were added and the mixture was hydrogenated at 5 bar. The mixture was filtered and the filtrate concentrated. 26 g (0.11 mmol; 94% yield) were obtained as a colorless solid.

Preparation of 3-(5-cyclopropyl-1H-pyrazol-3-yl)-5-(methylsulfonyl)-aniline

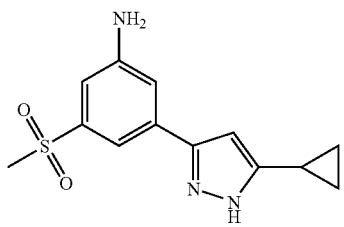 [SMILES: CS(=O)(=O)c1cc(N)cc(-c2cc(C3CC3)[nH]n2)c1]

3-Amino-5-(methylsulfonyl)benzoic acid methyl ester (8 g; 34.86 mmol) was diluted in 250 ml of dry 1,4-dioxane. Triethylamine (9.8 ml; 0.042 mol) and dimethylaminopyridine (5 g; 0.070 mol) were added. A solution of di-tert-butyl-dicarbonate (9 g; 0.042 mol) in 50 ml of 1,4-dioxane was added dropwise. The reaction mixture was refluxed 2 h, then it was concentrated in vacuo. The crude was diluted with dichloromethane and washed with saturated sodium bicarbonate solution. The organic phase was dried over MgSO$_4$ and concentrated in vacuo. The crude was treated with isopropyl ether and the precipitate filtered and dried in vacuo. 8.45 g (26 mmol; 73.5% yield) of 3-tert-butoxycarbonylamino-5-(methylsulfonyl)-benzoic acid methylester, as a white solid, were obtained.

3-tert-butoxycarbonylamino-5-(methylsulfonyl)-benzoic acid methyl ester (8.45 g; 25.65 mmol) was suspended in 1,4-dioxane (75 ml) and 100 ml of NaOH 1N solution. The reaction mixture was stirred at room temperature overnight. Then, it was concentrated in vacuo. The crude was suspended in water and treated with citric acid until pH 4. Then ethyl acetate was added, the organic phase separated, dried with MgSO$_4$ and concentrated in vacuo. 6.85 g (22 mmol; 84% yield) of 3-tert-butoxycarbonylamino-5-(methylsulfonyl)-benzoic acid were obtained.

3-Tert-butoxycarbonylamino-5-(methylsulfonyl)-benzoic acid (850 mg; 2.695 mmol) was diluted in 30 ml of THF, 1,1'-carbonyldiimidazole (1.3 g; 8.086 mmol) and triethylamine (0.818 ml; 5.661 mmol) were added. The reaction mixture was stirred at room temperature for 30 min., then, N,O-dimethylhydroxylamine (0.329 g; 0.005 mol) was added. The reaction mixture was refluxed overnight. Then, it was concentrated in vacuo. The crude was diluted with dichloromethane and to washed with a saturated sodium bicarbonate solution. The organic phase was separated, dried on MgSO$_4$ and concentrated in vacuo. The crude was treated with isopropyl ether/ethyl acetate 2/1. The precipitate formed was filtered and dried in vacuo. 460 mg (1.25 mmol; 46% yield) of [3-methanesulfonyl-5-(methoxy-methyl-carbamoyl)-phenyl]-carbamic acid tert-butyl ester were obtained as a white solid.

3-(Methylsulfonyl)-5-(methoxy-methyl-carbamoyl)-phenyl]-carbamic acid tert-butyl ester (250 mg; 1.256 mmol) was suspended in 35 ml of dry THF and the reaction mixture was cooled to −70° C. A 3M solution of methylmagnesiumchloride in THF (0.377 ml; 1.130 mmol) was added. The reaction mixture was stirred at −70° C. for 1 h. At the same time, a solution of n-butyllithium (1.412 ml of a 1.6M solution in hexane), was cooled at −70° C. and cyclopropylacetylene (0.119 ml; 1.256 mmol) was added. This solution was maintained at that temperature for 1 h then it was added to the reaction mixture. The reaction mixture was maintained at −70° C. for 30 min and then it was allowed to reach room temperature and maintained at that temperature for 2 h. The reaction mixture was then diluted with NH$_4$Cl saturated solution, the organic phase was separated, washed with brine, dried on MgSO$_4$ and concentrated in vacuo. 250 mg (0.688 mmol; 54% yield) of [3-(3-cyclopropyl-propynoyl)-5-methanesulfonyl-phenyl]-carbamic acid tert-butyl ester were obtained as an oil.

[3-(3-Cyclopropyl-propionyl)-5-methanesulfonyl-phenyl]-carbamic acid tert-butyl ester (250 mg; 0.688 mmol) was diluted in 5 ml of ethanol and hydrazine hydrate (0.186 ml; 3.439 mmol) was added. The reaction mixture was stirred at room temperature for 1 h. Then, it was concentrated under vacuum. 200 mg (0.53 mmol; 77% yield) of [3-(5-cyclopropyl-1H-pyrazol-3-yl)-5-(methylsulfonyl)-phenyl]-carbamic acid tert butyl ester were obtained.

[3-(5-Cyclopropyl-1H-pyrazol-3-yl)-5-(methylsulfonyl)-phenyl]-carbamic acid tert butyl ester (250 mg; 0.662 mmol) was suspended in 0.5 ml of 4 M HCl solution in 1,4-dioxane. The reaction mixture was stirred at room temperature for 1 h then it was concentrated in vacuo. 200 mg (0.638 mmol; 96% yield) of the desired aniline were obtained as hydrochloride.

Preparation of 3-(Ethylsulfonyl)-aniline

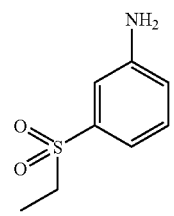

Ethylphenylsulfone (3.0 g; 18 mmol) was dissolved in 7 mL of conc. sulphuric acid then treated in portions with potassium nitrate (2.7 g; 26 mmol) and subsequently heated for 2 hours at 90° C. The reaction mixture cooled to ambient temperature was then poured onto ice and the precipitate was filtered off and dried to yield 3.8 g of an intermediate as yellow solid.

1-(Ethylsulfonyl)-3-nitro-benzene (1.9 g; 9 mmol) was dissolved in 80 mL of methanol then 1 g of Raney-Nickel is added and the mixture treated with hydrogen gas. The reaction mixture was subsequently filtered and concentrated to yield 1.5 g (8.1 mmol; yield=93%) of an yellow oil.

Preparation of 3-Isopropylsulfonylaniline

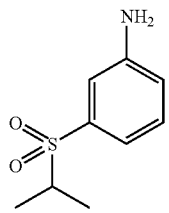

3-Isopropylsulfonylaniline was synthesized in analogy to 3-ethylsulfonylaniline starting with 3-(isopropylsulfonyl)-benzene.

Preparation of 2-(3-Amino-phenylsulfonyl)-ethanol

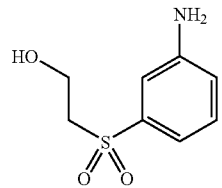 [SMILES: Nc1cccc(S(=O)(=O)CCO)c1]

2-(3-Nitrophenylsulfonyl)ethanol (10 g; 43 mmol) was dissolved in 200 ml tetrahydrofuran and 200 mL ethanol, 3 g Pd/C (10%) was added and the mixture treated with hydrogen gas. The solvents were removed to obtain 8.8 g (43 mmol, 100% yield) of the desired compound as colourless oil.

Preparation of 3-(2-dimethylaminoethylsulfonyl)-aniline

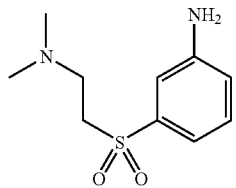

2-(Phenylsulfonyl)-ethanol (2.5 g; 13 mmol) was dissolved in 5.5 ml of conc. sulphuric acid and treated in portions with potassium nitrate (2 g; 20 mmol). The reaction mixture was heated for 2 hours at 90° C., then poured onto ice and potassium carbonate was added. The mixture was extracted several times with ethyl acetate and the combined organic layers were concentrated to obtain 0.9 g (3.9 mmol, 30% yield) of 2-(3-nitro-phenylsulfonyl)-ethanol as a yellow solid.

2-(3-Nitro-phenylsulfonyl)-ethanol (0.5 g; 2.6 mmol) was dissolved in 3 mL ethanol and 2 mL of dichloromethane. Then 1 mL of (7.8 mmol) dimethylamine (33% in ethanol) was added, the reaction mixture was subsequently concentrated in vacuo, dissolved in dichloromethane, and the product was precipitated by adding diethyl ether and petrol ether. 0.4 g (1.55 mmol; 59% yield) of dimethyl-[2-(3-nitro-benzenesulfonyl)-ethyl]-amine were obtained as a yellow solid.

Dimethyl-[2-(3-nitro-benzenesulfonyl)-ethyl]-amine (0.4 g; 1.5 mmol) was dissolved in 5 mL tetrahydrofuran and 5 mL ethanol. After addition of 150 mg Pd/C (5%) the mixture was treated with hydrogen, then filtered and concentrated in vacuo. The resulting residue was dissolved in acetone and precipitated with ethereal oxalic acid solution. 0.3 g (1.3: 88% yield) were obtained as a white solid (compound as the oxalic acid salt).

Preparation of 3-(2-morpholin-4-ylethylsulfonyl)-phenylaniline

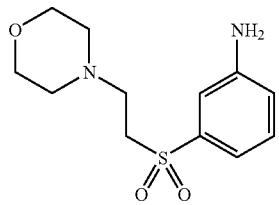 [SMILES: Nc1cccc(S(=O)(=O)CCN2CCOCC2)c1]

This aniline was prepared with the same procedure described for the preparation of 3-(2-Dimethylaminoethyl-sulfonyl)-aniline, using morpholine instead of dimethylamine. 770 mg (2.137 mmol; 98.7% yield) were obtained.

Preparation of (S)-3-N,S-dimethylsulfonimidoyl)aniline

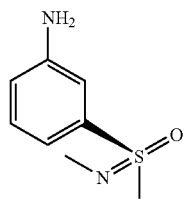

N,S-Dimethyl-5-phenylsulfoximine (3 g; 18 mmol) was dissolved in 20 mL conc. sulphuric acid and treated in portions with potassium nitrate (2.7 g; 27 mmol). The mixture was then heated for 3 hours to 100° C. and then poured onto ice. The aqueous mixture was then neutralized with potassium carbonate and extracted with dichloromethane and ethyl acetate. The combined organic layers were dried, concentrated and the resulting residue treated with small amounts of methanol. 2.3 g (10.7 mmol; 60% yield) of 3-nitro-N,S-dimethyl-5-phenylsulfoximine as white solid.

3-Nitro-N,S-Dimethyl-5-phenylsulfoximine (1.5 g; 7 mmol) was dissolved in 30 mL tetrahydrofuran, then a solution of tetrabutylammonium hydrogensulfate (0.5 g; 1.5 mmol) in 30 mL water was added and the mixture warmed to 60° C. Subsequently, sodium dithionite (5 g; 29 mmol) was added in portions and the mixture warmed for 4 hours to 80° C. After cooling to room temperature the mixture was concentrated and purified on silica gel (dichloromethane/methanol). 0.7 g (3.8 mmol; 54% yield) were obtained of colourless oil, which crystallizes on standing.

Preparation of (R)-1-(3-Amino-5-methanesulfonyl-phenyl)-5-ethyl-4-methyl-piperazin-2-one

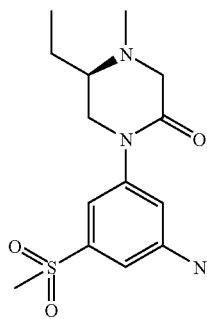 [SMILES: CC[C@@H]1CN(c2cc(N)cc(S(C)(=O)=O)c2)C(=O)CN1C]

3-(Methylsulfonyl)-5-nitro-aniline (4.3 g; 19.89 mmol) was diluted in 60 ml of ethyl acetate and a solution of potassium hydrogen carbonate (219 g, 21.87) in 10 ml of water was added. The reaction mixture was stirred at 0° C. and chloroacetylchloride (2.47 ml; 21.87 mmol) was added dropwise. The reaction mixture was allowed to reach room temperature and stirred for 2 h. Then, the phases were separated. The organic phase was dried on MgSO₄ and concentrated under vacuum. The oil obtained was treated with acetone/di-isopropyl ether (1/5) and the solid obtained was filtered. 2.5 g (8.54 mmol; 43% yield) of the desired 2-Chloro-N-(3-methanesulfonyl-5-nitro-phenyl)-acetamide were obtained.

2-Chloro-N-(3-methanesulfonyl-5-nitro-phenyl)-acetamide (750 mg; 2.56 mmol) was diluted in 40 of ethyl acetate, (R)-(−)-2-amino-1-butanol (1.01 ml; 10.25 mmol) was added and the reaction mixture was stirred at 75° C. overnight. The solvent was concentrated under vacuum and the crude was purified by flash chromatography (Isolute Silica cartridge 10 g; eluent: Dichloromethane:MeOH=99:1). 380 mg (1.10 mmol; 43% yield) of the desired 2-((R)-1-Hydroxymethyl-propylamino)-N-(3-methanesulfonyl-5-nitro-phenyl)-acetamide were obtained.

2-((R)-1-Hydroxymethyl-propylamino)-N-(3-methanesulfonyl-5-nitro-phenyl)-acetamide (180 mg; 0.521 mmol) was diluted in 5 ml of acetonitrile and a 36% solution of formaldehyde in water (0.087 ml; 10 mmol) was added. The reaction mixture was stirred for 5 min then triacetoxyborohydride (331 mg; 1.564 mmol) was added. The reaction mixture was stirred for 1 h and then the solvent was concentrated under vacuum. The crude was diluted with dichloromethane; the organic phase was washed with a saturated sodium hydrogen carbonate solution, and loaded on a SCX cartridge. The desired compound was recovered after washing the SCX cartridge with a 7 M solution of ammonia in methanol. This solution was concentrated under vacuum. 120 mg (0.33 mmol; 64% yield) of the desired 2-[((R)-1-Hydroxymethyl-propylmethyl-amino]-N-(3-methanesulfonyl-5-nitro-phenyl)-acetamide were obtained as yellow solid.

2-[((R)-1-Hydroxymethyl-propylmethyl-amino]-N-(3-methanesulfonyl-5-nitro-phenyl)-acetamide (120 mg; 0.334 mmol) was diluted in 3 ml of ethyl acetate, a solution of di-tert-butyl-azodicarboxylate (107 mg; 0.467 mmol) in of ethyl acetate (1 ml) and a solution of tri-N-butylphosphine (0.118 ml; 0.467 mmol) in ethyl acetate (3 ml) were added in sequence. The reaction mixture was warmed to 50° C. for 30 min. Then, the reaction mixture was diluted with methanol and loaded on a SCX cartridge. The desired compound was recovered after washing the SCX cartridge with a 7 M solution of ammonia in methanol. This solution was to concentrated under vacuum. The crude obtained was purified by flash chromatography (Isolute Silica cartridge 10 g; eluent: Dichloromethane:MeOH=98:2). 85 mg (0.249 mmol; 74% yield) of the desired (R)-5-Ethyl-1-(3-methanesulfonyl-5-nitro-phenyl)-4-methyl-piprazin-2-one were obtained.

R)-5-Ethyl-1-(3-methanesulfonyl-5-nitro-phenyl)-4-methyl-piprazin-2-one (85 mg; 0.149 mmol) was diluted in methanol, (10 ml) and 5 mg Pd/C (5% w/w) were added and the reaction mixture was hydrogenated at 2 bar. The mixture was then diluted with 1,4-dioxane, filtrated over a celite pad and loaded on SCX cartridge. The desired compound was recovered after washing the SCX cartridge with a 7 M solution of ammonia in methanol. The solution was concentrated under vacuum. 52 mg (0.16 mmol; 77.5% yield) of (R)-1-(3-Amino-5-methanesulfonyl-phenyl)-5-ethyl-4-methyl-piperazin-2-one were obtained.

Preparation of (S)-cyclopentyl-pyrrolidin-3-ylamine

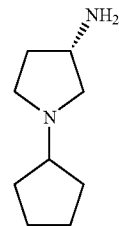 [SMILES: N[C@H]1CCN(C2CCCC2)C1]

(S)-Pyrrolidin-3-yl-carbamic acid tert-butyl ester (3 g; 0.016 mol) was suspended in 100 ml of dichloromethane and sodium triacetoxyborohydride (6.349 g; 0.030 mol) was added. A solution of cyclopentanone (4.29 ml; 0.048 mol) in 50 ml of dichloromethane was added dropwise to the reaction mixture. The reaction mixture was maintained at room temperature overnight; it was then diluted with dichloromethane and washed with saturated sodium bicarbonate solution. The organic phase was dried with MgSO₄ and concentrated under reduced pressure. 4 g of (S)-(1-cyclopentyl-3-yl)-carbamic acid tert-butyl ester were recovered as an colourless oil.

(S)-(1-cyclopentyl-pyrrolidine-3-yl)-carbamic acid tert-butyl (1 g; 3.91 mmol) was diluted in 10 ml of methanol and 3 ml of HCl 37% were added. The reaction mixture was stirred at room temperature overnight, then it was concentrated under reduced pressure. 860 mg (3.78 mmol; 96% yield) of the desired product were obtained as di-hydrochloride.

Preparation of (R)-cyclopentyl-pyrrolidin-3-ylamine

The preparation of (R)-cyclopentyl-pyrrolidin-3-ylamine di-hydrochloride was performed with the same procedure described for the (S) enantiomer. 900 mg (3.96 mmol; 100% yield) of the desired product were obtained as di-hydrochloride.

Preparation of (R)-(1-pyridin-4-yl-pyrrolidin-2-yl)-methylamine

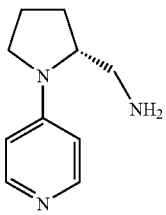 [SMILES: NC[C@H]1CCCN1c1ccncc1]

(R)-Pyrrolidin-2-ylmethyl-carbamic acid tert-butyl ester (80 mg; 0.99 mmol), 4-bromopyridine hydrochloride (77 mg; 0.99 mmol), NaOH 10% (0.2 ml) and 1,4-dioxane (0.2 ml) were mixed together. The reaction mixture was irradiated in a microwave reactor (OEM; 15 W, ramp 5 min.; hold 25 min.; 130° C.; 150 psi), then stirred at 70° C. overnight.

The reaction mixture was concentrated under reduced pressure and the crude was treated with 0.2 ml of 1,4-dioxane, 1 ml of water and 0.5 ml of HCl 37%. The reaction mixture was maintained at room temperature for 3 h, then treated with 2 ml of NaOH 10% and diluted with 10 ml of dichloromethane. The organic phase was separated, dried on $MgSO_4$ and concentrated under reduced pressure. 50 mg (0.282 mmol; 28%) of the desired product were obtained.

Preparation of (R)-1-(8-tetrahydro-pyran-4-yl)-pyrrolidin-3-ylamine

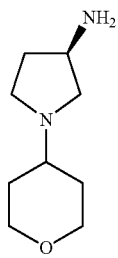 [SMILES: N[C@@H]1CCN(C2CCOCC2)C1]

(R)-Pyrrolidin-3-yl carbamic acid tert-butyl ester (200 mg; 1.074 mmol) was suspended in 7 ml of dichloromethane and sodium triacetoxyborohydride (455 mg; 2.15 mmol) was added. A solution of tetrahydro-4H-pyran-4-one (0.297 ml; 3.22 mmol) in 3 ml of dichloromethane was added drop-wise to the reaction mixture. The reaction mixture was maintained at room temperature overnight, it was then diluted with dichloromethane and washed with saturated sodium bicarbonate solution. The organic phase was dried with $MgSO_4$ and concentrated in vacuo. The product was obtained after loading the crude on a SCX-cartridge and recovering with MeOH/ammonia solution. 220 mg (0.641 mmol; 60% yield) of (R)-[1-(tetrahydro-pyran-4-yl)-pyrrolidin-3-yl]-carbamic acid tert-butyl ester were obtained as colourless oil.

(R)-[1-(Tetrahydro-pyran-4-yl)-pyrrolidin-3-yl]-carbamic acid tert-butyl ester (220 g; 0.814 mmol) was diluted in 5 ml of methanol and 0.5 ml of HCl 37% were added. The reaction mixture was stirred at room temperature overnight, then it was concentrated in vacuo. 165 mg (0.679 mmol; 83% yield) of the desired product were obtained as di-hydrochloride Preparation of (S)-1-(8-tetrahydro-pyran-4-yl)-pyrrolidin-3-ylamine (S)-enantiomer was prepared with the same procedure used for the preparation of the (R)-enantiomer. 190 mg (0.781 mmol; 96% yield) of the desired product were obtained as di-hydrochloride.

Preparation of (S)-1-cyclopentyl-pyrrolidin-2-ylmethyl)-methyl-amine

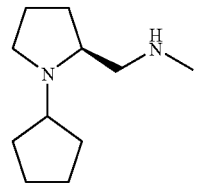

A 1M solution of lithiumaluminiumhydride in THF (6.52; 6.52 mmol) was added dropwise to a cooled (0° C.) solution of the (S)-pyrrolidin-2-ylmethyl-carbamic acid tert-butyl ester (500 mg; 1.863 mmol) in 50 ml of dry THF, under nitrogen atmosphere. The reaction mixture was allowed to reach room temperature and then refluxed overnight. Water was added and the reaction mixture was filtered on a celite pad and the THF solution concentrated in vacuo. The water phase was washed with ethyl acetate. The organic phase was dried on $MgSO_4$ and concentrated in vacuo. 300 mg (1.65 mmol; 88% yield) of product were obtained as oil.

Preparation of (R)-1-cyclopentyl-pyrrolidin-2-ylmethyl)-methyl-amine (R)-Enantiomer was prepared with the same procedure for the preparation of the (S)-enantiomer. 300 mg (1.65 mmol; 88% yield) of product were obtained as oil.

Preparation of (R)-1-cyclopentyl-pyrrolidin-3-ol

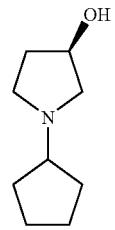 [SMILES: O[C@@H]1CCN(C2CCCC2)C1]

N-(Tert-butoxycarbonyl)-(R)-3-pyrrolidinol (5 g; 26.70 mmol) was diluted in 15 ml of methanol and 5 ml of HCl 37% were added. The reaction mixture was stirred at room temperature overnight, then it was concentrated in vacuo. 2.1 g (17.07 mmol; 63%) of the desired product were obtained as hydrochloride.

(R)-Pyrrolidin-2-ol hydrochloride (0.9 g; 7.31 mmol) was suspended in 50 ml of dichloromethane and sodium triacetoxyborohydride (4.37 g; 0.021 mol) was added. A solution of cyclopentanone (2.75 ml; 0.031 mol) in 530 ml of to dichloromethane was added drop-wise to the reaction mixture. The reaction mixture was maintained at room temperature overnight; it was then diluted with dichloromethane and washed with saturated sodium bicarbonate solution. The water phase was concentrated in vacuo. The crude was treated with dichloromethane in order to separate the salts. The salts were precipitated and filtered. The organic phase concentrated in vacuo. 450 mg (2.90 mmol; 40% yield) of the desired compound were obtained.

Preparation of (S)-1-cyclopentyl-pyrrolidin-3-ol (S)-Enantiomer was prepared with the same procedure for (R)-enantiomer. 500 mg (3.22 mmol; 41%) of the desired compound were obtained.

Synthesis of the Intermediate Compounds

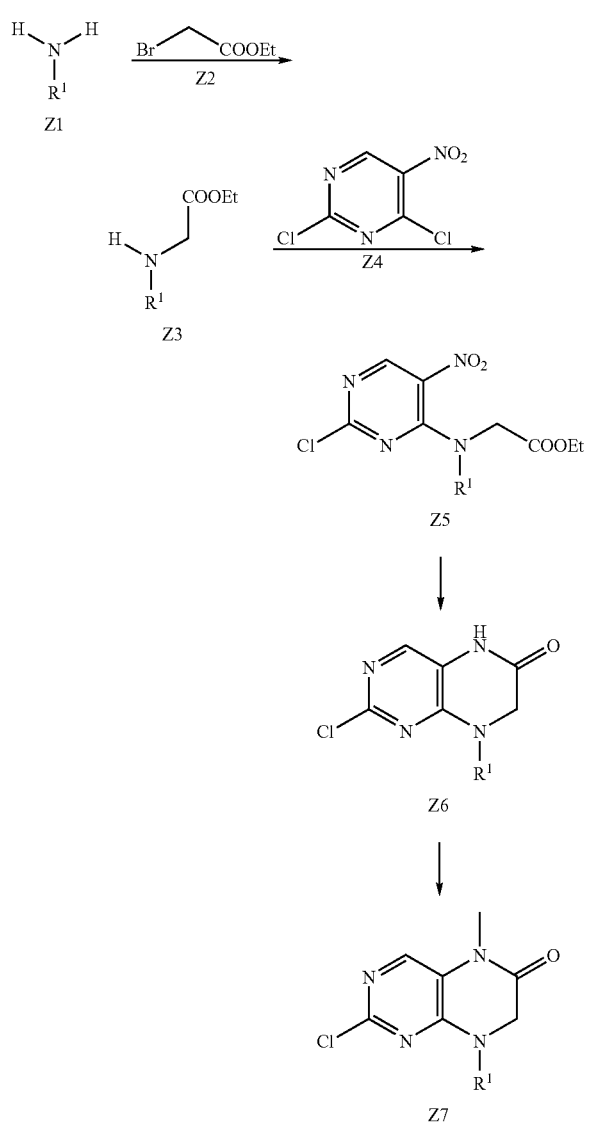

Preparation of 2-chloro-8-isopropyl-5-methyl-7,8-dihydro-5H-pteridin-6-one: ($R^1$=iPr)

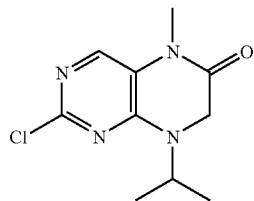 [SMILES: CC(C)N1CC(=O)N(C)c2cnc(Cl)nc21]

Preparation of [(2-chloro-5-nitro-pyrimidin-4yl)-isopropyl-amino]-acetic acid ethyl ester

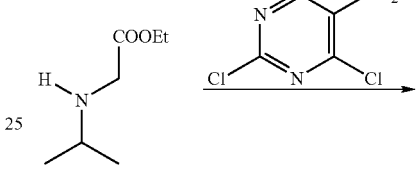

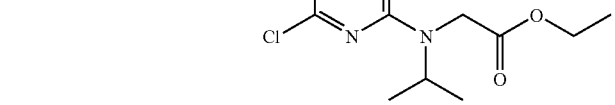

2,4-Dichloro-5-nitro-pyrimidine (40 g; 0.207 mol) was added to a cooled (0-10° C.) solution of isopropylamino-acetic acid ethyl ester (30 g; 0.207 mol) in 300 ml of acetone. A solution of potassium carbonate (28.5 g; 0.207 mol) in water was then added to the cooled reaction mixture. The reaction mixture was allowed to reach room temperature and was maintained at that temperature until complete conversion of the starting material into the desired product.

The reaction mixture was concentrated in vacuo, diluted with dichloromethane and washed with water. The organic phase was dried with $MgSO_4$ and concentrated in to vacuo. 45 g (0.149 mol; 72% yield) of yellow powder were obtained.

Preparation of
2-chloro-8-isopropyl-7,8-dihydro-5H-pteridin-6-one

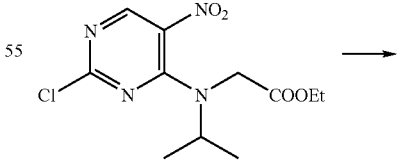

A suspension of [(2-chloro-5-nitro-pyrimidin-4-yl)-isopropyl-amino]-acetic acid ethyl ester (40 g; 0.132 mol), Pt/C$_5$% (2 g) and vanadylacetylacetonate (2 g; 0.754 mmol) in THF (50 ml) was treated with hydrogen (5 bar) overnight. The reaction mixture was warmed (in order to solubilize the precipitate formed) and filtered on a celite pad, then concentrated in vacuo. The crude was diluted in ethyl acetate and the organic phase was washed with NaOH 10% solution, dried with MgSO4 and concentrated in vacuo. 28 g (0.115 mol; 87% yield) of solid material were obtained.

Preparation of 2-chloro-8-isopropyl-5-methyl-7,8-dihydro-5H-pteridin-6-one

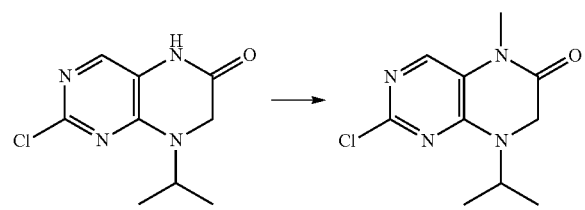 [SMILES: CC(C)N1CC(=O)Nc2cnc(Cl)nc21 ; CC(C)N1CC(=O)N(C)c2cnc(Cl)nc21]

2-Chloro-8-isopropyl-7,8-dihydro-5H-pteridin-6-one (28 g; 0.118 mol) in Dimethylacetamide (100 ml) was cooled to −5° C. and iodomethane (8.839 ml; 0.141 mmol)) was quickly added. Then, NaH (7.1 g; 0.177 mmol) was added in portions. After 1 h the reaction mixture was allowed to reach room temperature and was maintained at that temperature until complete conversion of the starting material into the desired product. The reaction mixture was diluted with water and ice and the precipitate formed was filtered and dried in vacuo. 20 g (0.083 mol; 70% yield) of a white powder were obtained.

Preparation of 2-chloro-8-cyclopropyl-5-methyl-7,8-dihydro-5H-pteridin-6-one: (R1=cyclopropyl)

This intermediate was prepared with the same procedure as for $R^1$=iPr.

Preparation of 3-(8-isopropyl-5-methyl-6-oxo-5,6,7,8-tetrahydro-pteridin-2-ylamino)-5-trifluoromethyl-benzoic acid 2-Chloro-8-isopropyl-5-methyl-7,8-dihydro-5H-pteridin-6-one (3.5 g; 14.54 mmol) and 3-amino-5-(trifluoromethyl)-benzoic acid (2.98 g; 14.54 mmol) were diluted in 15 ml of water and 15 ml of 1,4-dioxane, 2 ml of HCl 37% were added. The reaction mixture was refluxed 24 h, then cooled to room temperature. The desired product precipitated from the reaction mixture, it was filtered, washed with water and dried in vacuo. 4.77 g (0.012 mol; 80% yield) were obtained as white powder.

Preparation of 3-(8-isopropyl-5-methyl-6-oxo-5,6,7,8-tetrahydro-pteridin-2-ylamino)-5-(methylsulfonyl) amino-benzoic acid This intermediate was prepared following the same procedure used for the preparation of 3-(8-isopropyl-5-methyl-6-oxo-5,6,7,8-tetrahydro-pteridin-2-ylamino)-5-trifluoromethyl-benzoic acid (R═CF$_3$) and described in Scheme 2.

Starting from 2-chloro-8-isopropyl-5-methyl-7,8-dihydro-5H-pteridin-6-one (1.5 g; 6.25 mmol) and 3-amino-5-(methylsulfonyl)aminobenzoic acid methyl ester (3.49 g; 14.502 mmol), 950 mg (2.18 mmol; 35% yield) of the desired product were obtained as a powder.

Preparation of 3-(8-isopropyl-5-methyl-6-oxo-5,6,7,8-tetrahydro-pteridin-2-ylamino)-5-methanesulfonyl-benzoic acid This intermediate was prepared following the same procedure used for the preparation of 3-(8-isopropyl-5-methyl-6-oxo-5,6,7,8-tetrahydro-pteridin-2-ylamino)-5-trifluoromethyl-benzoic acid (R═CF$_3$) and described in Scheme 2.

Starting from 2-chloro-8-isopropyl-5-methyl-7,8-dihydro-5H-pteridin-6-one (4.8 g; 0.05 mmol) and 3-amino-5-(methylsulfonyl)-benzoic acid methyl ester (5.5 g; 0.024 mmol), 6.4 g (15.27 mmol; 77% yield) of white powder were obtained.

Scheme 2

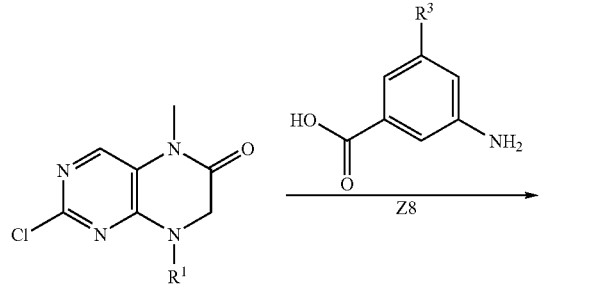

Scheme 3

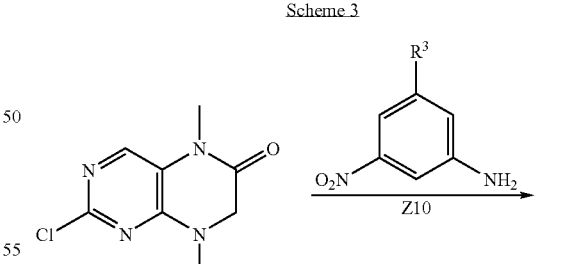

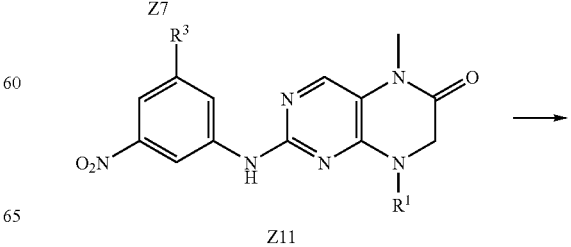

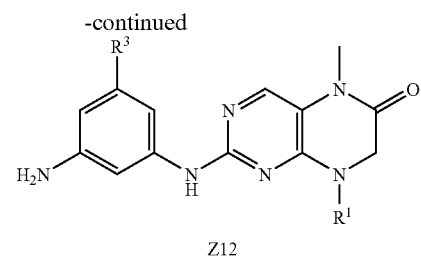

Z12

Preparation of 2-(3-amino-5-trifluoromethyl-phenylamino)-8-isopropyl-5-methyl-7,8-dihydro-5H-pteridin-6-one

Preparation of 8-isopropyl-5-methyl-2-(3-nitro-5-trifluoromethyl-phenylamino)-7,8-dihydro-5H-pteridin-6-one 2-Chloro-8-isopropyl-5-methyl-7,8-dihydro-5H-pteridin-6-one of (2 g; 8.30 mmol) and 3-nitro-5-trifluoromethyl-phenylamine (1.71 g; 8.30 mmol) were diluted in 10 ml of water and 10 ml of 1,4-dioxane. 2 ml of HCl 37% were added. The reaction mixture was refluxed 48 h, then cooled to room temperature. The desired product precipitated from the reaction mixture, so, it was filtered, washed with water and dried in vacuo. Recrystallisation with 1,4-dioxane/water 1:1 gave 1.65 g (4.04 mmol; 49% yield) of white-yellow powder.

Preparation of 2-(3-nitro-5-trifluoromethyl-phenylamino)-8-isopropyl-5-methyl-7,8-dihydro-5H-pteridin-6-one The suspension of 8-isopropyl-5-methyl-2-(3-nitro-5-trifluoromethyl-phenylamino)-7,8-dihydro-5H-pteridin-6-one (1.6 g; 3.08 mmol) and Pd—C 10% (160 mg) in 150 ml of methanol was hydrogenated (1 bar) 36 h. The catalyst was filtered on celite and the reaction solution was concentrated in vacuo. 940 mg (2.47 mmol; 64% yield) of the desired product were obtained as powder.

Preparation of 3-amino-5-(8-isopropyl-5-methyl-6-oxo-5,6,7,8-tetrahydro-pteridin-2-ylamino)-benzenesulfonamide This intermediate was prepared following the same procedure used for the preparation of 2-(3-Amino-5-trifluoromethyl-phenylamino)-8-isopropyl-5-methyl-7,8-dihydro-5H-pteridin-6-one (R=CF$_3$) and described in Scheme 3.

Preparation of 3-(8-isopropyl-5-methyl-6-oxo-5,6,7,8-tetrahydro-pteridin-2-ylamino)-5-nitro-benzenesulfonamide Starting from 2-chloro-8-isopropyl-5-methyl-7,8-dihydro-5H-pteridin-6-one (3.15 g; 4.502 mmol) and 3-amino-5-nitro-benzenesulfonamide (3.49 g; 14.502 mmol), 4.4 g (10.45 mmol; 72% yield) of the desired nitro-product were obtained as a powder.

Preparation of 3-amino-5-(8-isopropyl-5-methyl-6-oxo-5,6,7,8-tetrahydro-pteridin-2-ylamino)-benzenesulfonamide Starting from 3-(8-isopropyl-5-methyl-6-oxo-5,6,7,8-tetrahydro-pteridin-2-ylamino)-5-nitro-benzenesulfonamide (4.4 g; 10.44 mmol), 2.5 g (6.39 mmol; 61% yield) of the desired compound were obtained.

Preparation of 2-(3-amino-5-methanesulfonyl-phenylamino)-8-isopropyl-5-methyl-7,8-dihydro-5H-pteridin-6-one This intermediate was prepared following the same procedure used for the preparation of 2-(3-amino-5-trifluoromethyl-phenylamino)-8-isopropyl-5-methyl-7,8-dihydro-5H-pteridin-6-one (R=CF$_3$) and described in Scheme 3.

Preparation of 8-isopropyl-2-(3-(methanesulfonyl-5-nitro-phenylamino)-5-methyl-7,8-dihydro-5H-pteridin-6-one Starting from 2-chloro-8-isopropyl-5-methyl-7,8-dihydro-5H-pteridin-6-one (9.35 g; 38.85 mmol) and 3-methansulfonyl-5-nitro-phenylamine (8.4 g; 38.5 mmol), 9.4 g (22.38 mmol; 57.5% yield) of the desired nitro-product were obtained as a powder.

Preparation of 2-(3-amino-5-methanesulfonyl-phenylamino)-8-isopropyl-5-methyl-7,8-dihydro-5H-pteridin-6-one Starting from 8-isopropyl-2-(3-methanesulfonyl-5-nitro-phenylamino)-5-methyl-7,8-dihydro-5H-pteridin-6-one (9.4 g; 22.35 mmol), 7.35 g (18.84 mmol; 84% yield) of the desired compound were obtained as a powder.

Scheme 4

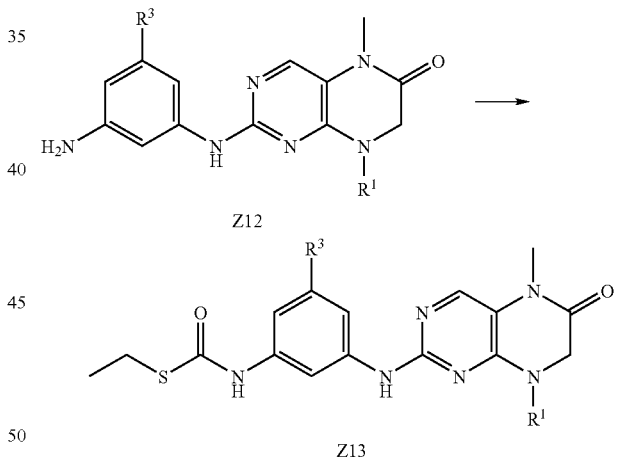

Preparation of [3-(8-Isopropyl-5-methyl-6-oxo-5,6,7,8-tetrahydro-pteridin-2-ylamino)-5-trifluoromethyl-phenyl]-thiocarbamic acid ethyl ester Ethylchlorothioformate (0.754 ml; 7.230 mmol) was added dropwise to a cooled (0° C.) suspension of 2-(3-Amino-5-trifluoromethyl-phenylamino)-8-isopropyl-5-methyl-7,8-dihydro-5H-pteridin-6-one (2.5 g; 6.573 mmol) in 10 ml of dry Pyridine. The reaction mixture was allowed to reach room temperature and maintained at that temperature 2 h. Water was added to the reaction mixture and the precipitated formed was filtered washed with water and dried in vacuo. 2.1 g (4.48 mmol; 68% yield) of a yellow powder were obtained.

Preparation of [3-(8-isopropyl-5-methyl-6-oxo-5,6,7,8-tetrahydro-pteridin-2-ylamino)-5-sulfamoyl-phenyl]-thiocarbamic acid ethyl ester (R=SO₂NH₂)

This intermediate was prepared following the same procedure used for the preparation of [3-(8-isopropyl-5-methyl-6-oxo-5,6,7,8-tetrahydro-pteridin-2-ylamino)-5-trifluoromethyl-phenyl]-thiocarbamic acid ethyl ester and described in Scheme 4. Starting from ethylchlorothioformate (0.380 ml; 3.65 mmol) and 3-amino-5-(8-isopropyl-5-methyl-6-oxo-5,6,7,8-tetrahydro-pteridin-2-ylamino)-benzenesulfonamide (1.3 g; 3.321 mmol), 900 mg (18.78 mmol; 57% yield) of a yellow powder were obtained.

Preparation of [3-(8-isopropyl-5-methyl-6-oxo-5,6,7,8-tetrahydro-pteridin-2-ylamino)-5-(methylsulfonyl)-phenyl]-thiocarbamic acid ethyl ester (R=SO₂Me)

This intermediate was prepared following the same procedure used for the preparation of [3-(8-isopropyl-5-methyl-6-oxo-5,6,7,8-tetrahydro-pteridin-2-ylamino)-5-trifluoromethyl-phenyl]-thiocarbamic acid ethyl ester and described in to Scheme 4. Starting from ethylchlorothioformate (0.640 ml; 6.147 mmol) and 2-(3-amino-5-(methylsulfonyl)-phenylamino)-8-isopropyl-5-methyl-7,8-dihydro-5H-pteridin-6-one (2 g; 5.122 mmol), 2.33 g (4.86 mmol; 95% yield) of a yellow powder were obtained.

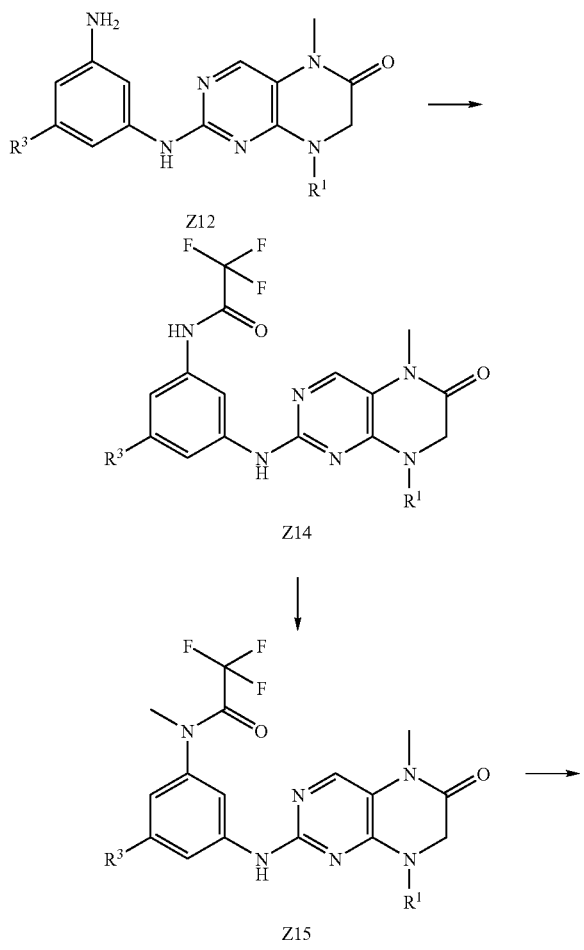

Scheme 5

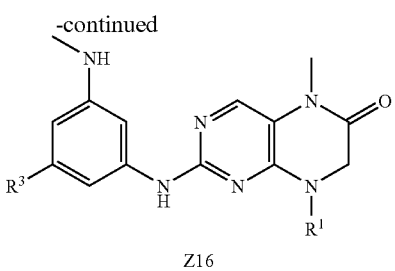

Z16

Preparation of 8-isopropyl-2-(3-methanesulfonyl-5-methylamino-phenylamino)-5-methyl-7,8-dihydro-5H-pteridin-6-one

Preparation of 2,2,2-trifluoro-N-[8-isopropyl-5-methyl-6-oxo-5,6,7,8-tetrahydro-pteridin-2-ylamino)-5-methanesulfonyl-phenyl]-acetamide 2-(3-Amino-5-(methylsulfonyl)-phenylamino)-8-isopropyl-5-methyl-7,8-dihydro-5H-pteridin-6-one (2 g; 5.122 mmol) was diluted in 50 ml of dichloromethane. Triethylamine (4.26 ml; 30.6 mmol) was added and the reaction mixture was cooled to 0° C. Trifluoroacetic anhydride (3.6 ml; 25.5 mmol) in 2 ml of dichloromethane were added drop-wise. The reaction mixture was allowed to reach room temperature and maintained at that temperature overnight. The reaction mixture was then diluted with dichloromethane and washed with to bicarbonate saturated solution. The organic phase was separated, dried on MgSO₄ and concentrated in vacuo. The crude was treated with ethyl ether and the solid obtained filtered and dried in vacuo. 1.65 g (3.93 mmol; 66% yield) of the desired compound were obtained.

Preparation of 2,2,2-trifluoro-N-[8-isopropyl-5-methyl-6-oxo-5,6,7,8-tetrahydro-pteridin-2-ylamino)-5-methanesulfonyl-phenyl]-N-methyl-acetamide 2,2,2-Trifluoro-N-[8-isopropyl-5-methyl-6-oxo-5,6,7,8-tetrahydro-pteridin-2-ylamino)-5-methanesulfonyl-phenyl]-acetamide (1.6 g; 3.289 mmol), iodomethane (0.265 ml; 4.26 mmol) and K₂CO₃ (906 mg; 6.560 mmol) were mixed in 80 mL of acetone and the reaction mixture was stirred at room temperature overnight.

The reaction mixture was then diluted with dichloromethane and washed with water and NaCl saturated solution. The organic phase was separated, dried on MgSO₄ and concentrated in vacuo. 1.6 g (3.2 mmol; 97% yield) of the desired compound were obtained as beige solid.

Preparation of 8-isopropyl-2-(3-methanesulfonyl-5-methylamino-phenylamino)-5-methyl-7,8-dihydro-5H-pteridin-6-one 2,2,2-Trifluoro-N-[8-isopropyl-5-methyl-6-oxo-5,6,7,8-tetrahydro-pteridin-2-ylamino)-5-methanesulfonyl-phenyl]-N-methyl-acetamide (1.6 g; 3.197 mmol) and 30 ml of a 2M water solution of Na₂CO₃ in 100 mL of methanol were stirred overnight at room temperature.

The reaction mixture was then diluted with dichloromethane and washed with water and NaCl saturated solution. The organic phase was separated, dried on MgSO₄ and concentrated in vacuo. 1.1 g (2.72 mmol; 85% yield) of the desired compound were obtained as yellow solid.

Example 150

Table 1

Preparation of 2-(3-(2-hydroxyethylsulfonyl)phenylamino)-8-isopropyl-5-methyl-7,8-dihydropteridin-6(5H)-one

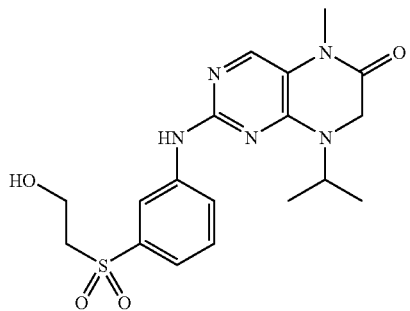 [SMILES: CC(C)N1CC(=O)N(C)c2cnc(Nc3cccc(S(=O)(=O)CCO)c3)nc21]

2-Chloro-8-isopropyl-5-methyl-7,8-dihydro-5H-pteridin-6-one (150 mg; 0.623 mmol) and 2-(3-Amino-phenylsulfonyl)-ethanol (120 mg; 0.600 mmol) were heated to 160° C. for 30 minutes. The reaction mixture was then suspended in dichloromethane and ethyl acetate then filtrated to yield 215 mg (0.530 mmol; 85% yield) as yellow solid.

Preparation of methanesulfonic acid 2-[3-(8-isopropyl-5-methyl-6-oxo-5,6,7,8-tetrahydro-pteridin-2-ylamino)-benzenesulfonyl]-ethyl ester

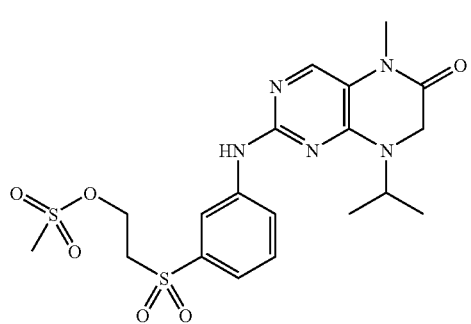 [SMILES: CC(C)N1CC(=O)N(C)c2cnc(Nc3cccc(S(=O)(=O)CCOS(C)(=O)=O)c3)nc21]

2-(3-(2-Hydroxyethylsulfonyl)phenylamino)-8-isopropyl-5-methyl-7,8-dihydropteridin-6(5H)-one (1.45 g; 3.576 mmol) was dissolved in 35 mL dichloromethane, ethyldiisopropylamine (0.92 mL; 5.360 mmol) and 4-dimethylaminopyridine (cat.) were added. Then the mixture was cooled to 0° C. and mesylchloride (0.332 ml; 4.290 mmol) was added slowly. The reaction mixture was allowed to get to room temperature and after 4 h water was added and the mixture was extracted with dichloromethane. Drying of the organic layer with sodium sulphate and removal of the solvents gave 1.1 g (2.275; 63% yield) of intermediate the desired product as foam.

Analytical Methods

| Method A | |
|---|---|
| Instrument: | LC/MS ThermoFinnigan. Hplc Surveyor DAD, LCQduo Ion trap |
| Column: | sunryse MS-C18, 5 um, 4.6 × 100 mm |
| Mobile phase: | A = $H_2O$ + 20 mM $HCOONH_4$ |
| | B = ACN + 20 mM $HCOONH_4$ |
| Flow rate: | 850 uL/min |
| Gradient: | A/B (95:5) for 1 minutes, then to A/B (5:95) in 7 minutes for 1.5 minutes |
| Detection: | UV @ 254 nm |
| Detection: | Finnigan LCQduo, Ion trap |
| | Ion source: ESI |
| | Scan range: 100-900 |

| Method B | |
|---|---|
| Instrument: | LC/MS ThermoFinnigan. Hplc Surveyor DAD, MSQ Quadrupole |
| Column: | sunryse MS-C8, 5 um, 4.6 × 100 mm |
| Mobile phase: | A = H2O + 20 mM HCOONH4 |
| | B = ACN + 20 mM HCOONH4 |
| Flow rate: | 1500 uL/min - |
| Gradient: | A/B (95:5) for 1.5 minutes, then to A/B (5:95) in 11 minutes for 1.5 minutes |
| Detection: | UV @ 254 nm |
| Detection: | Finnigan MSQ, quadrupole |
| | Ion source: APCI |
| | Scan range: 110-900 |

| Method C | |
|---|---|
| Instrument: | LC/MS ThermoFinnigan. Hplc Surveyor DAD, MSQ Quadrupole |
| Column: | sunryse MS-C8, 5 um, 4.6 × 100 mm |
| Mobile phase: | A = H2O + 20 mM HCOONH4 |
| | B = ACN + 20 mM HCOONH4 |
| Flow rate: | 1500 uL/min |
| Gradient: | A/B (95:5) for 1 minutes, then to A/B (5:95) in 7 minutes for 1 minutes |
| Detection: | UV @ 254 nm |
| Detection: | Finnigan MSQ, Quadrupole |
| | Ion source: APCI |
| | Scan range: 110-900 |

| Method D | |
|---|---|
| Instrument: | LC/MS ThermoFinnigan. Hplc Surveyor DAD, MSQ Quadrupole |
| Column: | sunryse MS-C18, 5 um, 4.6 × 100 mm |
| Mobile phase: | A = H2O + 0.1% HCOOH |
| | B = ACN + 0.1% HCOOH |
| Flow rate: | 1500 uL/min |
| Gradient: | A/B (95:5) for 1.5 minutes, then to A/B (5:95) in 11 minutes for 1.5 minutes |
| Detection: | UV @ 254 nm |
| Detection: | Finnigan MSQ, Quadrupole |
| | Ion source: APCI |
| | Scan range: 110-900 |

| Method E | |
|---|---|
| Instrument: | LC/MS ThermoFinnigan. Hplc Surveyor DAD, LCQduo Ion trap. |
| Column: | sunryse MS-C18, 5 um, 4.6 × 100 mm |
| Mobile phase: | A = H2O + 0.1% HCOOH<br>B = ACN + 0.1% HCOOH |
| Flow rate: | 850 uL/min |
| Gradient: | A/B (95:5) for 1 minutes, then to A/B (5:95) in 7 minutes for 1 minutes |
| Detection: | UV @ 254 nm |
| Detection: | Finnigan LCQduo, Ion trap<br>Ion source: ESI<br>Scan range: 110-900 |

| Method 1E | |
|---|---|
| Instrument: | LC/MS ThermoFinnigan. Hplc Surveyor DAD, MSQ Quadrupole. |
| Column: | Symmetry C8, 5 um, 3 × 150 mm |
| Mobile phase: | A = H2O + 10% acetonitrile + ammonium formate 10 mM<br>B = ACN 90% + 10% $H_2O$ + $NH_4COOH$ 10 mM |
| Flow rate: | 1.2 mL/min |
| Gradient: | A (100) for 1.5 min, then to B (100) in 10 min for 1.5 min |
| Detection: | UV @ 254 nm |
| Detection: | Finnigan LCQduo, Ion trap<br>Ion source: APCI |

| Method Open Access Grad_pos | |
|---|---|
| Instrument: | LC/MS Waters. Hplc Alliance 2695 DAD, ZQ Quadrupole. |
| Column: | synergi fusion MS-C18, 5 um, 4.6 × 100 mm |
| Mobile phase: | A = H2O + 0.1% HCOOH<br>B = ACN |
| Flow rate: | 1000 uL/min |
| Gradient: | A/B (90:10), then to A/B (10:90) in 5 minutes for 1 minutes |
| Detection: | UV @ 254 nm |
| Detection: | Waters ZQ, Quadrupole<br>Ion source: ESI<br>Scan range: 130-900 |

| Method Open Access Grad_long | |
|---|---|
| Instrument: | LC/MS Waters. Hplc Alliance 2695 DAD, ZQ Quadrupole. |
| Column: | synergi fusion MS-C18, 5 um, 4.6 × 100 mm |
| Mobile phase: | A = H2O + 0.1% HCOOH<br>B = ACN |
| Flow rate: | 1000 uL/min |
| Gradient: | A/B (90:10), then to A/B (10:90) in 8 minutes for 1.5 minutes |
| Detection: | UV @ 254 nm |
| Detection: | Waters ZQ, Quadrupole<br>Ion source: ESI<br>Scan range: 130-900 |

| Method Gradient | |
|---|---|
| Instrument: | LC/MS Waters. Hplc Alliance 2695 DAD, ZQ Quadrupole. |
| Column: | Xterra MS-C8, 5 um, 4.6 × 100 mm |
| Mobile phase: | A = H2O + 0.1% TFA<br>B = ACN |

| Method Gradient | |
|---|---|
| Flow rate: | 1000 uL/min |
| Gradient: | A/B (90:10), then to A/B (10:90) in 8 minutes for 1.5 minutes |
| Detection: | UV @ 254 nm |
| Detection: | Waters ZQ, Quadrupole<br>Ion source: ESI<br>Scan range: 130-900 |

| Method Gradient_2 | |
|---|---|
| Instrument: | LC/MS Waters. Hplc Alliance 2695 DAD, ZQ Quadrupole. |
| Column: | Xterra MS-C8, 5 um, 4.6 × 100 mm |
| Mobile phase: | A = H2O + 0.1% TFA<br>B = ACN |
| Flow rate: | 1000 uL/min |
| Gradient: | A/B (90:10), then to A/B (10:90) in 14 minutes for 1.5 minutes |
| Detection: | UV @ 254 nm |
| Detection: | Waters ZQ, Quadrupole<br>Ion source: ESI<br>Scan range: 130-900 |

| Method F | |
|---|---|
| Instrument: | LC/MS ThermoFinnigan. Hplc Surveyor DAD, MSQ Quadrupole |
| Column: | sunryse MS-C8, 5 um, 4.6 × 100 mm |
| Mobile phase: | A = H2O + TFA<br>B = ACN |
| Flow rate: | 100 uL/min - |
| Gradient: | A/B (90:10) then to A/B (10:90) in 20 minutes for 1.5 minutes |
| Detection: | UV @ 254 nm |
| Detection: | Finnigan MSQ, quadrupole<br>Ion source: APCI<br>Scan range: 110-900 |

| Method G | |
|---|---|
| Instrument: | LC/MS ThermoFinnigan. Hplc Surveyor DAD, äüMSQ Quadrupole |
| Column: | sunryse MS-C8, 5 um, 4.6 × 100 mm |
| Mobile phase: | A = H2O + TFA<br>B = ACN |
| Flow rate: | 1000 uL/min - |
| Gradient: | A/B (90:10) then to A/B (10:90) in 14 minutes |
| Detection: | UV @ 254 nm |
| Detection: | Finnigan MSQ, quadrupole<br>Ion source: APCI<br>Scan range: 130-900 |

| Method H | |
|---|---|
| Instrument: | LC/MS ThermoFinnigan. Hplc Surveyor DAD, LCQduo Ion trap. |
| Column: | sunryse MS-C18, 5 um, 4.6 × 100 mm |
| Mobile phase: | A = H2O + 0.1% TFA<br>B = ACN |
| Flow rate: | 1000 uL/min |
| Gradient: | A/B (90:10) then to A/B (10:90) in 14 minutes |

-continued

Method H

| | |
|---|---|
| Detection: | UV @ 254 nm |
| Detection: | Finnigan LCQduo, Ion trap |
| | Ion source: ESI |
| | Scan range: 130-900 |

Method H2

| | |
|---|---|
| Instrument: | LC/MS ThermoFinnigan. Hplc Surveyor DAD, LCQduo Ion trap. |
| Column: | sunryse MS-C18, 5 um, 4.6 × 100 mm |
| Mobile phase: | A = H2O + 0.1% HCOOH |
| | B = ACN + 0.1% HCCOH |
| Flow rate: | 1000 uL/min |
| Gradient: | A/B (90:10) then to A/B (10:90) in 14 minutes |
| Detection: | UV @ 254 nm |
| Detection: | Finnigan LCQduo, Ion trap |
| | Ion source: ESI |
| | Scan range: 130-900 |

Method I

| | |
|---|---|
| Instrument: | LC/MS ThermoFinnigan. Hplc Surveyor DAD, LCQduo Ion trap |
| Column: | sunryse MS-C18, 5 um, 4.6 × 100 mm |
| Mobile phase: | A = $H_2O$ + 20 mM $HCOONH_4$ |
| | B = ACN + 20 mM $HCOONH_4$ |
| Flow rate: | 1500 uL/min |
| Gradient: | A/B (95:5) for 1 minutes, then to A/B (5:95) in 7 minutes for 1.5 minutes |
| Detection: | UV @ 254 nm |
| Detection: | Finnigan LCQduo, Ion trap |
| | Ion source: APCI |
| | Scan range: 120-900 |

Method L

| | |
|---|---|
| Instrument: | LC/MS Waters. Hplc Alliance 2695 DAD, ZQ Quadrupole. |
| Column: | Xterra MS-C8, 3.5 um, 4.6 × 50 mm |
| Mobile phase: | A = H2O + $NH_4COOH$ 5 mM + 10 ACN |
| | B = ACN |
| Flow rate: | 1300 uL/min |
| Gradient: | A 100, then to A/B (10:90) in 3.25 minutes for 0.75 minutes |
| Detection: | UV @ 254 nm |
| Detection: | Waters ZQ, Quadrupole |
| | Ion source: ESI |
| | Scan range: 120-900 |

Method M

| | |
|---|---|
| Instrument: | LC/MS Waters. Hplc Alliance 2695/2690, DAD, ZMD. |
| Column: | Merck Chromolith Flash RP-18e, 3.5 um, 4.6 × 25 mm |
| Mobile phase: | A = H2O + 0.1% trifluoroacetic acid |
| | B = ACN + 0.1% trifluoroacetic acid |
| Flow rate: | 2500 uL/min |
| Gradient: | A = 95% for 0.2 min., then to A = 2% in 1.3 min., A = 2% for 0.2 min., then to A = 95% in 0.2 min |

Preparative HPLC-MS Methods

Preparative method A

| | |
|---|---|
| Instruments: | Waters 2525 Binary gradient module |
| | Waters 515 Make up pump |
| | Waters 2767 Sample manager injector and collector |
| | Waters CFO |
| | Waters Mass spectrometer ZQ |
| | Waters 996 DAD |
| Software: | MassLynx 4.0 |
| Column: | Sun Fire C18 5 μm 30 × 100 mm, Waters |
| Eluent: | A: 0.1% TFA in $H_2O$ |
| | B: ACN |
| | Gradient from 10% B to 90% B in 8 min. |
| Preparative flow: | 40 mL/min |
| Eluent make up: | 15% $H_2O$ 85% MeOH 0.1% HCOOH |
| Flow make up: | 1 mL/min |
| DAD detector: | 200-400 nm |
| MS detector: | positive ESI ionization |

Preparative method B

| | |
|---|---|
| Instruments: | Waters 2525 Binary gradient module |
| | Waters 515 Make up pump |
| | Waters 2767 Sample manager injector and collector |
| | Waters CFO |
| | Waters Mass spectrometer ZQ |
| | Waters 996 DAD |
| Software: | MassLynx 4.0 |
| Column: | Gemini C18 5 μm 30 × 100 mm, Phenomenex |
| Eluent: | A: 0.05% TFA in $H_2O$ |
| | B: ACN |
| | Gradient from 10% B to 90% B in 8 min. |
| Preparative flow: | 40 mL/min |
| Eluent make up: | 15% $H_2O$ 85% MeOH 0.1% HCOOH |
| Flow make up: | 1 mL/min |
| DAD detector: | 200-400 nm |
| MS detector: | positive ESI ionization |

Preparative method C

| | |
|---|---|
| Instruments: | Waters 2525 Binary gradient module |
| | Waters 515 Make up pump |
| | Waters 2767 Sample manager injector and collector |
| | Waters CFO |
| | Waters Mass spectrometer ZQ |
| | Waters 996 DAD |
| Software: | MassLynx 4.0 |
| Column: | Gemini C18 5 μm 30 × 100 mm, Phenomenex |
| Eluent: | A: 0.05% TFA in $H_2O$ |
| | B: ACN |
| | Gradient from 10% B to 90% B in 12 min. |
| Preparative flow: | 40 mL/min |
| Eluent make up: | 15% $H_2O$ 85% MeOH 0.1% HCOOH |
| Flow make up: | 1 mL/min |
| DAD detector: | 200-400 nm |
| MS detector: | positive ESI ionization |

| Preparative method D | |
|---|---|
| Instruments: | Waters 2525 Binary gradient module |
| | Waters 515 Make up pump |
| | Waters 2767 Sample manager injector and collector |
| | Waters CFO |
| | Waters Mass spectrometer ZQ |
| | Waters 996 DAD |
| Software: | MassLynx 4.0 |
| Column: | X Terra C8 MS 5 μm 30 × 100 mm, Waters |
| Eluent: | A: 0.1% TFA in H$_2$O |
| | B: ACN6 |
| | Gradient from 25% B to 60% B in 8 min. |
| Preparative flow: | 40 mL/min |
| Eluent make up: | 15% H$_2$0 85% MeOH 0.1% HCOOH |
| Flow make up: | 1 mL/min |
| DAD detector: | 200-400 nm |
| MS detector: | positive ESI ionization |

Settings ZQ MS Detector:

| | |
|---|---|
| Polarity: | ES positive |
| Mass range: | 150 to 1000 amu |
| Capillary: | 3.5 kV |
| Cone: | 25.0 V |
| Source: | 130° C. |
| Desolvation: | 300° C. |
| Cone Gas: | 100 L/hr |
| Desolv gas: | 600 L/hr |

Settings 2767 Sample Manager:

| | |
|---|---|
| Loop: | 1000 μL |
| Syringe size: | 1000 μL |
| Trigger: | Mass |

| Preparative method E | |
|---|---|
| Instruments: | Waters 2525 Binary gradient module |
| | Waters 515 Make up pump |
| | Waters 2767 Sample manager injector and collector |
| | Waters Column Fluidics Organizer |
| | Waters ZQ single quadrupole mass spectrometer |
| | Waters 996 DAD |
| Software: | MassLynx vers. 4.0 |
| Column: | X Terra C8 MS 5 μm 30 × 100 mm, Waters |
| Splitter: | 1/1000 Accurate by LC Packings |

Settings 2525 Preparative ump:

| | |
|---|---|
| Solvent A: | 0.1% TFA in H$_2$O |
| Solvent B: | ACN |
| Stop run: | 10 min |

| Time (min) | Flow (mL/min) | % A | % B | Curve |
|---|---|---|---|---|
| Initial (0) | 40 | 70 | 30 | 6 = Linear |
| 1.0 | 40 | 70 | 30 | 6 = Linear |
| 8.0 | 40 | 40 | 60 | 6 = Linear |
| 8.5 | 40 | 10 | 90 | 6 = Linear |
| 9.0 | 40 | 70 | 30 | 6 = Linear |

Settings 515 Make Up Pump:

| | |
|---|---|
| Solvent: | 10% H$_2$0 90% MeOH 0.1% HCOOH |
| Flow: | 1 mL/min |

Settings 996 DAD Detector:

| | |
|---|---|
| Start Wavelength: | 200 nm |
| End Wavelength: | 400 nm |
| Resolution: | 1.2 nm |
| Sampling rate: | 1 spectra/sec |

| Preparative method F | |
|---|---|
| Instruments: | Waters 2525 Binary gradient module |
| | Waters 515 Make up pump |
| | Waters 2767 Sample manager injector and collector |
| | Waters Column Fluidics Organizer |
| | Waters Quattro/micro triple quadropole mass spectrometer |
| | Waters 2996 DAD |
| Software: | MassLynx vers. 4.0 |
| Column: | Atlantis dC18, 5 μm, 19 × 100 mm, Waters |
| Splitter: | 1/1000 Accurate by LC Packings |

Settings 2525 Preparative Pump:

| | |
|---|---|
| Solvent A: | 0.05% TFA in H$_2$O |
| Solvent B: | ACN |
| Stop run: | 10 min |

| Time (min) | Flow (mL/min) | % A | % B | Curve |
|---|---|---|---|---|
| Initial (0) | 20 | 80 | 20 | 6 = Linear |
| 1.0 | 20 | 80 | 20 | 6 = Linear |
| 7.0 | 20 | 50 | 50 | 6 = Linear |
| 8.5 | 20 | 10 | 90 | 6 = Linear |
| 9.0 | 20 | 80 | 20 | 6 = Linear |

Settings 515 Make Up Pump:

| | |
|---|---|
| Solvent: | 10% H$_2$0 90% MeOH 0.1% HCOOH |
| Flow: | 1 mL/min |

Settings 996 DAD Detector:

| | |
|---|---|
| Start Wavelength: | 210 nm |
| End Wavelength: | 400 nm |
| Resolution: | 1.2 nm |
| Sampling rate: | 1 spectra/sec |

Settings ZQ MS Detector:

| | |
|---|---|
| Polarity: | ES positive |
| Mass range: | 150 to 1000 amu |
| Capillary: | 3.5 kV |
| Cone: | 25.0 V |
| Source: | 130° C. |
| Desolvation: | 250° C. |
| Cone Gas: | 100 L/hr |
| Desolv gas: | 650 L/hr |

Settings 2767 Sample Manager:

| | |
|---|---|
| Loop: | 1000 μL |
| Syringe size: | 1000 μL |
| Trigger: | Mass |

Preparative method G

| | |
|---|---|
| Instruments: | Waters 2525 Binary gradient module |
| | Waters 515 Make up pump |
| | Waters 2767 Sample manager injector and collector |
| | Waters Column Fluidics Organizer |
| | Waters Quattro/micro triple quadropole mass spectrometer |
| | Waters 2996 DAD |
| Software: | MassLynx vers. 4.0 |
| Column: | XTerra C8 MS, 5 μm, 19 × 100 mm, Waters |
| Splitter: | 1/1000 Accurate by LC Packings |

Settings 2525 Preparative Pump:

| | |
|---|---|
| Solvent A: | 0.05% TFA in $H_2O$ |
| Solvent B: | ACN |
| Stop run: | 10 min |

| Time (min) | Flow (mL/min) | % A | % B | Curve |
|---|---|---|---|---|
| Initial (0) | 20 | 70 | 30 | 6 = Linear |
| 1.0 | 20 | 70 | 30 | 6 = Linear |
| 7.0 | 20 | 40 | 60 | 6 = Linear |
| 7.5 | 20 | 10 | 90 | 6 = Linear |
| 8.5 | 20 | 10 | 90 | 6 = Linear |
| 9.0 | 20 | 70 | 30 | 6 = Linear |

Settings 515 Make Up Pump:

| | |
|---|---|
| Solvent: | 10% $H_2O$ 90% MeOH 0.1% HCOOH |
| Flow: | 1 mL/min |

Settings 996 DAD Detector:

| | |
|---|---|
| Start Wavelength: | 210 nm |
| End Wavelength: | 400 nm |
| Resolution: | 1.2 nm |
| Sampling rate: | 1 spectra/sec |

Settings ZQ MS Detector:

| | |
|---|---|
| Polarity: | ES positive |
| Mass range: | 150 to 1000 amu |
| Capillary: | 3.5 kV |
| Cone: | 25.0 V |
| Source: | 130° C. |
| Desolvation: | 250° C. |
| Cone Gas: | 100 L/hr |
| Desolv gas: | 650 L/hr |

Settings 2767 Sample Manager:

| | |
|---|---|
| Loop: | 1000 μL |
| Syringe size: | 1000 μL |
| Trigger: | Mass |

Preparative method H

| | |
|---|---|
| Instruments: | Waters 2525 Binary gradient module |
| | Waters 515 Make up pump |
| | Waters 2767 Sample manager injector and collector |
| | Waters Column Fluidics Organizer |
| | Waters Quattro/micro triple quadropole mass spectrometer |
| | Waters 2996 DAD |
| Software: | MassLynx vers. 4.0 |
| Column: | SunFire OBD C18, 5 μm, 19 × 100 mm, Waters |
| Splitter: | 1/1000 Accurate by LC Packings |

Settings 2525 Preparative Pump:

| | |
|---|---|
| Solvent A: | 0.1% TFA in $H_2O$ |
| Solvent B: | ACN |
| Stop run: | 10 min |

| Time (min) | Flow (mL/min) | % A | % B | Curve |
|---|---|---|---|---|
| Initial (0) | 20 | 65 | 35 | 6 = Linear |
| 7.0 | 20 | 35 | 65 | 6 = Linear |
| 7.5 | 20 | 10 | 90 | 6 = Linear |
| 8.5 | 20 | 10 | 90 | 6 = Linear |
| 9.0 | 20 | 65 | 35 | 6 = Linear |

Settings 515 Make Up Pump:

| | |
|---|---|
| Solvent: | 10% $H_2O$ 90% ACN 0.1% HCOOH |
| Flow: | 1 mL/min |

Settings 996 DAD detector:

| | |
|---|---|
| Start Wavelength: | 210 nm |
| End Wavelength: | 400 nm |
| Resolution: | 1.2 nm |
| Sampling rate: | 1 spectra/sec |

Settings ZQ MS Detector:

| | |
|---|---|
| Polarity: | ES positive |
| Mass range: | 150 to 1000 amu |
| Capillary: | 3.5 kV |
| Cone: | 25.0 V |
| Source: | 130° C. |
| Desolvation: | 250° C. |
| Cone Gas: | 100 L/hr |
| Desolv gas: | 650 L/hr |

Settings 2767 Sample Manager:

| | |
|---|---|
| Loop: | 1000 μL |
| Syringe size: | 1000 μL |
| Trigger: | Mass |

Synthesis of Compounds of Formula 1

Scheme 6

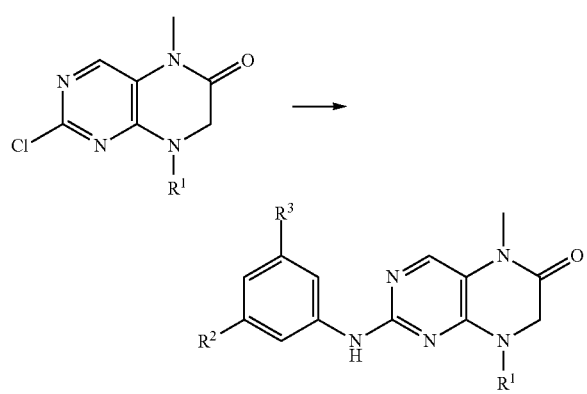

Ex.: 1; 2; 7; 22; 23; 24; 38; 39; 40; 141; 142; 143; 151; 152; 153; 154; 155.

Example 1

Table 1

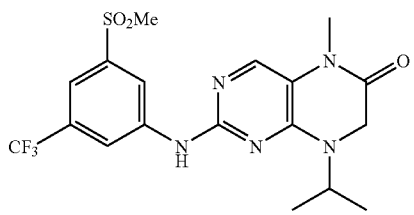 [SMILES: CC(C)N1CC(=O)N(C)c2cnc(Nc3cc(C(F)(F)F)cc(S(C)(=O)=O)c3)nc21]

2-Chloro-8-isopropyl-5-methyl-7,8-dihydro-5H-pteridin-6-one (20 mg; 0.083 mmol) and 3-(methylsulfonyl)-5-trifluoromethyl-phenylamine (19.8 mg; 0.083 mmol) were dissolved in 0.1 ml of 1,4-dioxane, 0.1 ml of water and 10 μl of HCl 37%. The reaction mixture was irradiated in a microwave reactor (OEM; 200 W, ramp 5 min.; hold 20 min.; 200° C.; 150 psi). The reaction mixture was diluted with dichloromethane and treated with scavenger resin PS-CHO in order to remove the un-reacted primary aniline. After 1 h, the organic phase was filtered and concentrated in vacuo. The crude was treated with isopropyl ether and the precipitate obtained was filtered and dried in vacuo. 10 mg (0.024 mmol; 28% yield) of the desired compound were obtained.

LC-MS method: Gradient_2

Retention time: 7.78 min

[M+H]=444

The following example was prepared with the same procedure described for the preparation of Example 1 and reported in Scheme 6.

Example 141

Table 1

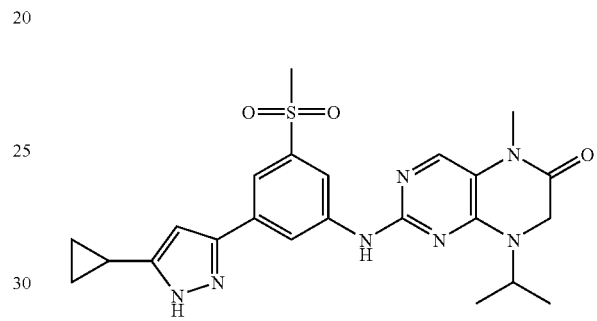

Starting from 2-chloro-8-isopropyl-5-methyl-7,8-dihydro-5H-pteridin-6-one (45 mg; 0.175 mmol) and 3-(5-cyclopropyl-1H-pyrazol-3-yl)-5-(methylsulfonyl)-aniline (49 mg; 0.158 mmol), 6 mg (0.012 mmol; 7% yield) of the desired compound were obtained.

LC-MS method: A

Retention time: 6.65 min

[M+H]=482

Scheme 7

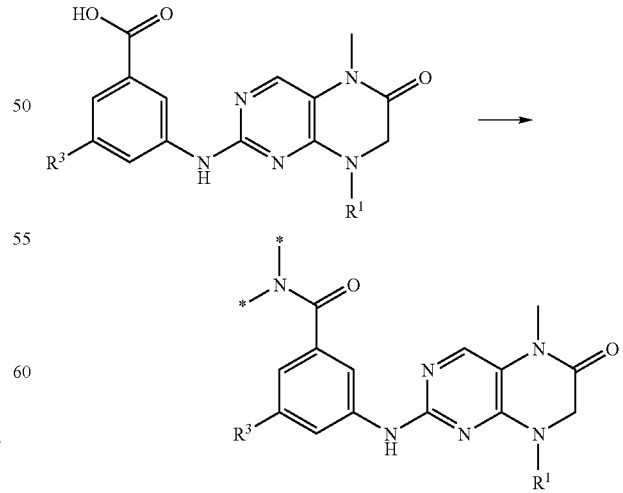

Ex.: 3; 4; 5; 6; 13; 14; 15; 16; 17; 18; 19; 20; 21; 25; 26; 27; 28; 29; 30; 31; 32; 33; 34; 35; 36.

Example 3

Table 1

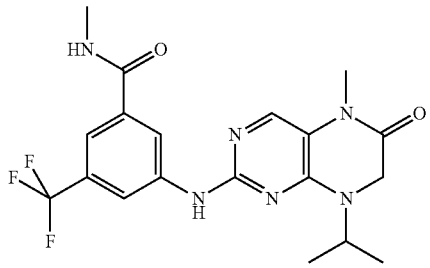 [SMILES: CNC(=O)c1cc(Nc2ncc3c(n2)N(C(C)C)CC(=O)N3C)cc(C(F)(F)F)c1]

1,1'-Carbonyldiimidazole (40 mg; 0.244 mmol) was added to a warmed (50° C.) suspension of 3-(8-isopropyl-5-methyl-6-oxo-5,6,7,8-tetrahydro-pteridin-2-ylamino)-5-trifluoromethyl-benzoic acid (50 mg; 0.122 mmol). The reaction mixture was maintained at that temperature for 6 h, then methylamine (2M solution in THF; 0.305 ml; 0.611 mmol) was added. The reaction mixture was maintained to 50° C. overnight. The reaction mixture was diluted with dichloromethane and washed with water. The organic phase was separated and dried on a phase separator and concentrated. The crude was treated with isopropyl ether/acetone and the precipitate obtained was filtered and dried in vacuo. 25 mg (0.059 mmol; 48% yield) of the desired compound were obtained.

LC-MS method: G

Retention time: 5.28 min

[M+H]=423

The following examples were prepared with the same procedure described for the preparation of Example 3 and reported in Scheme 7.

Example 13

Table 1

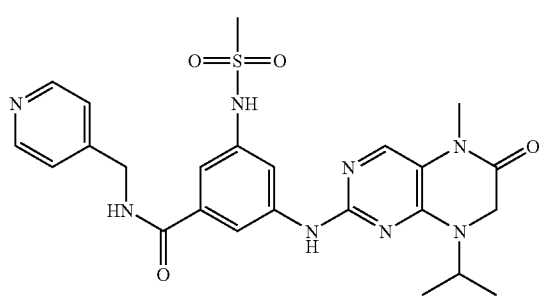 [SMILES: CC(C)N1CC(=O)N(C)c2cnc(Nc3cc(NS(C)(=O)=O)cc(C(=O)NCc4ccncc4)c3)nc21]

Starting from 3-(8-isopropyl-5-methyl-6-oxo-5,6,7,8-tetrahydro-pteridin-2-ylamino)-5-methanesulfonylamino-benzoic acid (40 mg; 0.0.092 mmol) and 4-(aminomethyl)-pyridine (0.05 ml; 0.46 mmol), 14 mg (0.027 mmol; 29% yield) of the desired compound were obtained.

LC-MS method: Gradient_2

Retention time: 5.03 min

[M+H]=525

Example 25

Table 1

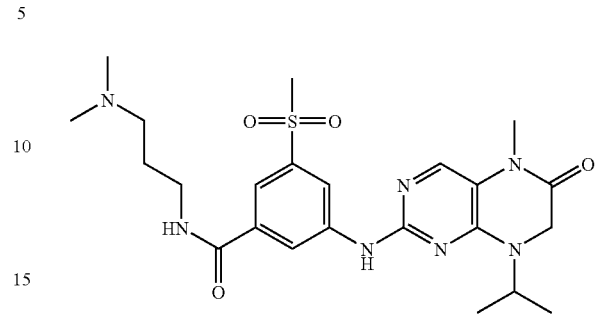

Starting from 3-(8-isopropyl-5-methyl-6-oxo-5,6,7,8-tetrahydro-pteridin-2-ylamino)-5-(methylsulfonyl)-benzoic acid (80 mg; 0.092 mmol) and N,N-dimethyl-1,3-propanediamine (0.120 ml; 0.954 mmol), 44 mg (0.087 mmol; 46% yield) of the desired compound were obtained.

LC-MS method: Gradient

Retention time: 3.11 min

[M+H]=504

Example 37

Table 1

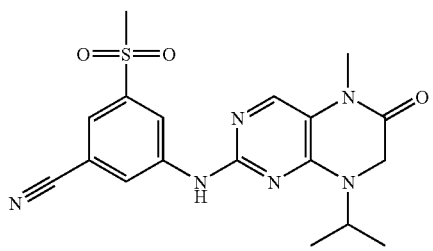 [SMILES: CC(C)N1CC(=O)N(C)c2cnc(Nc3cc(C#N)cc(S(C)(=O)=O)c3)nc21]

3-(8-Isopropyl-5-methyl-6-oxo-5,6,7,8-tetrahydro-pteridin-2-ylamino)-5-(methylsulfonyl)-benzamide (100 mg; 0.239 mmol) (prepared as described in Example 28) was diluted in 1 ml of dry DMF and, under nitrogen atmosphere, phosphorous oxychloride (0.55 ml; 0.597 mmol) was added. The reaction was warmed to 80° C. overnight. Then, it was cooled to room temperature, diluted with dichloromethane and washed with saturated bicarbonate solution. The organic phase was separated and dried on a phase separator and concentrated. The crude was treated with isopropyl ether/methanol. 74.5 mg (0.186 mmol; 78% yield) of the desired compound were obtained.

LC-MS method: E

Retention time: 4.21 min

[M+H]=401

Scheme 8

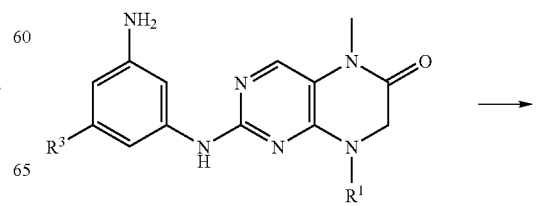

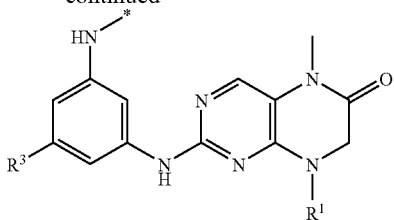

Ex: 41; 42.

Example 41

Table 1

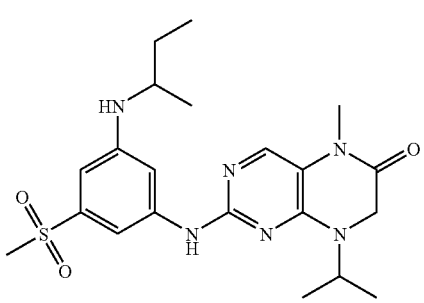 [SMILES: CCC(C)Nc1cc(Nc2ncc3c(n2)N(C(C)C)CC(=O)N3C)cc(S(C)(=O)=O)c1]

2-(3-Amino-5-(methylsulfonyl)-phenylamino)-8-isopropyl-5-methyl-7,8-dihydro-5H-pteridin-6-one (50 mg; 0.128 mmol), sodium triacetoxyborohydride (40 mg; 0.192 mmol) and methylethylketone (0.011 ml; 0.128 mmol) were dissolved in 2 ml of dichloromethane. The reaction mixture was stirred at room temperature overnight, it was then diluted with dichloromethane and washed with saturated sodium bicarbonate solution, filtered on phase separator and concentrated. The crude was purified with HPLC-MS preparative method D. 12.4 (0.072 mmol; 58% yield) of the desired compound were obtained.

LC-MS method: E
Retention time: 5.34 min
[M+H]=447

Example 42

Table 1

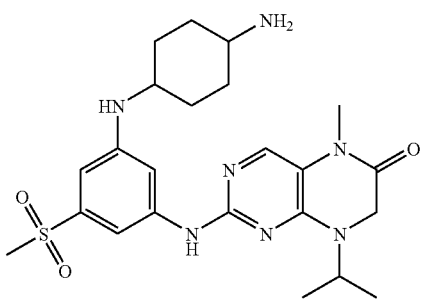 [SMILES: CC(C)N1CC(=O)N(C)c2cnc(Nc3cc(NC4CCC(N)CC4)cc(S(C)(=O)=O)c3)nc21]

Example 42 was prepared with the same procedure described for the preparation of Example 41 starting from 2-(3-amino-5-(methylsulfonyl)-phenylamino)-8-isopropyl-5-methyl-7,8-dihydro-5H-pteridin-6-one (45 mg; 0.115 mmol and (4-oxo-cyclohexyl)-carbamic acid tert-butyl ester (122 mg; 0.576 mmol). 6 mg (0.012 mmol; 11% yield) of the desired compound were obtained.

LC-MS method: L
Retention time: 2.1/min
[M+H]=488

Scheme 9

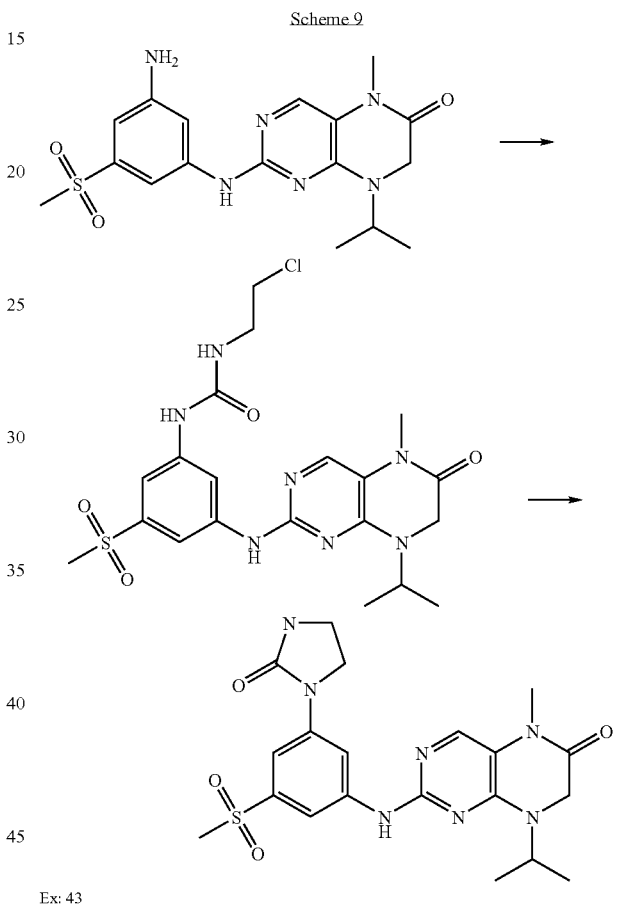

Ex: 43

Preparation of 1-(2-chloro-ethyl)-3-[3-(8-isopropyl-5-methyl-6-oxo-5,6,7,8-tetrahydro-pteridin-2-ylamino)-5-methylsulfonyl-phenyl]urea 2-(3-Amino-5-(methylsulfonyl)-phenylamino)-8-isopropyl-5-methyl-7,8-dihydro-5H-pteridin-6-one (300 mg; 0.768 mmol) was diluted under nitrogen atmosphere in 3 ml of dry 1,4-dioxane, then a solution of 2-chloroethyl-isocyanate (0.09 ml; 0.999 mmol) in 2 ml of dry 1,4-dioxane was added drop-wise. The reaction mixture was stirred at room temperature for 3 h, then warmed to 60° C. and maintained at that temperature for 3 h. The reaction mixture was then concentrated in vacuo. The crude obtained was treated with isopropyl ether. The solid obtained was filtered. 261 mg (0.001 mol; 68.5 yield) of the desired compound were obtained.

Example 43

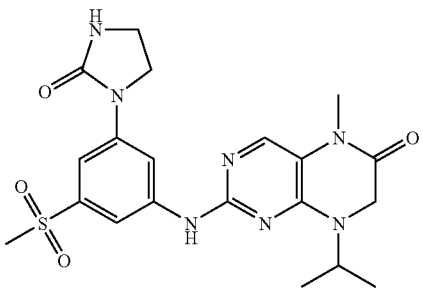 [SMILES: CC(C)N1CC(=O)N(C)c2cnc(Nc3cc(N4CCNC4=O)cc(S(C)(=O)=O)c3)nc21]

1-(2-Chloro-ethyl)-3-[3-(8-isopropyl-5-methyl-6-oxo-5,6,7,8-tetrahydro-pteridin-2-ylamino)-5-(methylsulfonyl)-phenyl]-urea (250 mg; 0.504 mmol) and Cesium carbonate (224 mg; 0.655 mmol) were diluted under nitrogen atmosphere in 15 ml of dry acetonitrile. The reaction mixture was warmed to 60° C. and stirred at that to temperature for 2 h. A formation of a solid was observed. It was filtered, washed with water and dried in vacuo. 75 mg (0.163 mmol; 32% yield) of the desired compound were obtained.

LC-MS method: A
Retention time: 4.3 min
[M+H]=460

Scheme 10

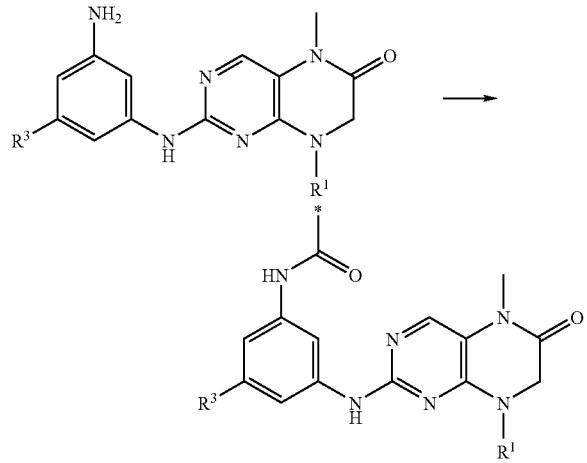

Ex.: 44; 58; 59; 45; 46; 47; 48; 49; 50; 51; 52; 53; 54; 55; 56; 57; 60; 61; 62, 63; 64; 65; 66; 67; 68; 69; 70; 71; 72.

Example 44

Table 1

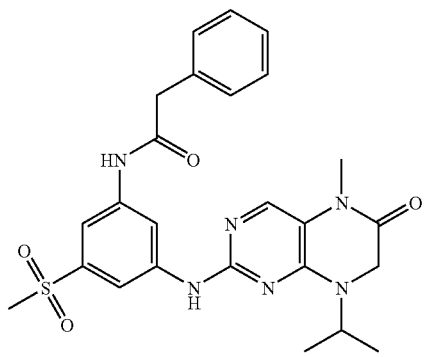 [SMILES: CC(C)N1CC(=O)N(C)c2cnc(Nc3cc(NC(=O)Cc4ccccc4)cc(S(C)(=O)=O)c3)nc21]

2-(3-Amino-5-methanesulfonyl-phenylamino)-8-isopropyl-5-methyl-7,8-dihydro-5H-pteridin-6-one (40 mg; 0.102 mmol) was dissolved in 1 ml of dry dichloromethane. Triethylamine (0.027 ml; 0.205 mmol) was added and the reaction mixture was cooled to 0° C. Phenylacetylchloride (0.016 ml; 0.123 mmol) in 0.5 ml of dry dichloromethane was added drop-wise. The reaction mixture was allowed to reach room temperature and then warmed to 40° C. 1 ml of dry DMF was added in order to increase solubilization and the reaction mixture was stirred at 40° C. for 2 h. The reaction mixture was then diluted with dichloromethane and washed with saturated sodium bicarbonate solution, the organic phase was filtered on a phase separator and concentrated. The crude was purified with HPLC-MS preparative method E. 7.1 mg (0.014 mmol; 14% yield) of the desired compound were obtained.

LC-MS method: G
Retention time: 6.23 min
[M+H]=509

Example 45

Table 1

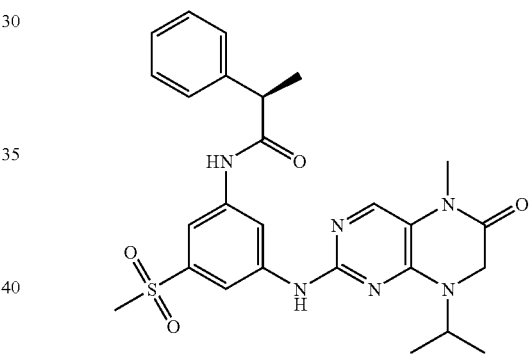

(R)-2-phenylpropionic acid (0.026 ml; 0.192 mmol), TBTU (65.7 mg; 0.205 mmol) DIPEA (65 ul; 0.384 mmol) in 1 ml of DMF were stirred at room temperature for 30 min. 2-(3-Amino-5-(methylsulfonyl)-phenylamino)-8-isopropyl-5-methyl-7,8-dihydro-5H-pteridin-6-one (50 mg; 0.128) was added and the reaction mixture was warmed to 50° C. overnight. The reaction mixture was diluted with dichloromethane and washed with water. The organic phase was filtered on a phase separator, and 50 mg of a PS-CHO scavenger resin were added. The organic phase was stirred overnight, then the resin was filtered and the organic phase concentrated. The crude obtained was purified with HPLC-MS preparative method B. 32 mg (0.063 mmol; 49% yield) of the desired compound were obtained.

LC-MS method: I
Retention time: 5.97 min
[M+H]=523

The following examples were prepared with the same procedure described for the preparation of Example 45 and reported in Scheme 10.

Example 51

Table 1

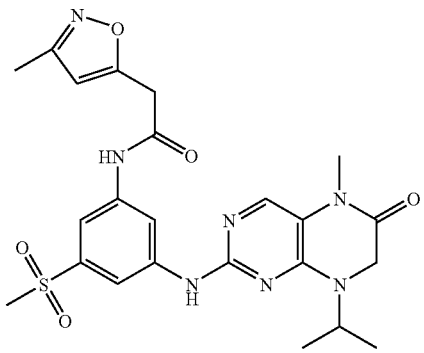 [SMILES: Cc1cc(CC(=O)Nc2cc(Nc3ncc4c(n3)N(C(C)C)CC(=O)N4C)cc(S(C)(=O)=O)c2)on1]

Starting from 3-methyl-5-isoxazole-acetic acid 21.6 mg; 0.154 mmol) and 2-(3-amino-5-(methylsulfonyl)-phenylamino)-8-isopropyl-5-methyl-7,8-dihydro-5H-pteridin-6-one (40 mg; 0.102), 40.6 mg (0.079 mmol; 77% yield) of the desired compound were obtained.

LC-MS method: A

Retention time: 4.7 min

[M+H]=514

Example 57

Table 1

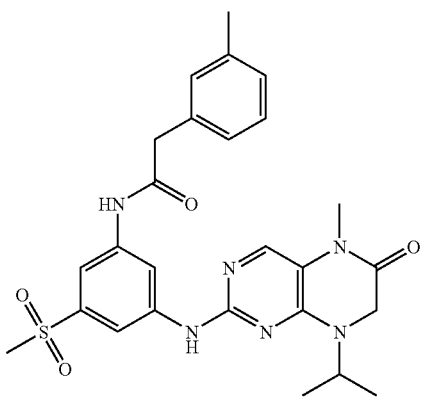 [SMILES: Cc1cccc(CC(=O)Nc2cc(Nc3ncc4c(n3)N(C(C)C)CC(=O)N4C)cc(S(C)(=O)=O)c2)c1]

Starting from m-tolyl-acetic acid (23.08 mg; 0.154 mmol) and 2-(3-amino-5-(methylsulfonyl)-phenylamino)-8-isopropyl-5-methyl-7,8-dihydro-5H-pteridin-6-one (40 mg; 0.102), 51.6 mg (0.099 mmol; 96% yield) of the desired compound were obtained.

LC-MS method: A

Retention time: 6.93 min

[M+H]=523

Scheme 11

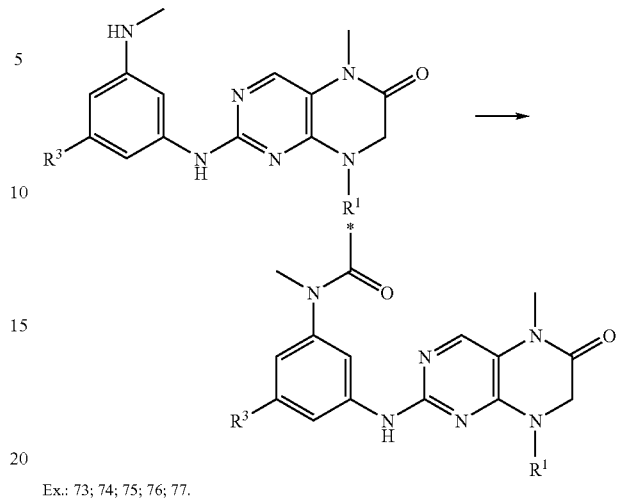

Ex.: 73; 74; 75; 76; 77.

Example 73

Table 1

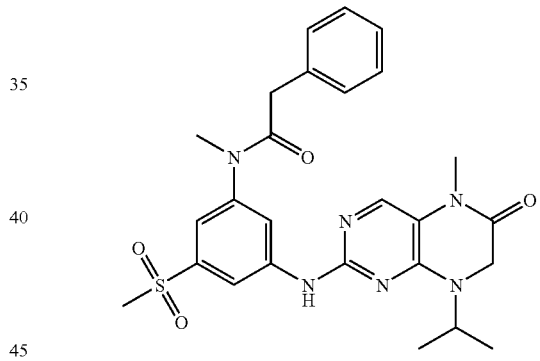

8-Isopropyl-2-(3-(methylsulfonyl)-5-methylamino-phenylamino)-5-methyl-7,8-dihydro-5H-pteridin-6-one (30 mg; 0.074 mmol) was dissolved in 1 ml of dry 1,4-dioxane. Triethylamine (0.04 ml; 0.304 mmol) was added and the reaction mixture was cooled to 0° C. Phenylacetylchloride (0.014 ml; 0.111 mmol) in 0.5 ml of dry 1,4-dioxane was added dropwise. The reaction mixture was allowed to reach room temperature and then warmed to 40° C. for 2 h. Phenylacetylchloride (0.014 ml; 0.111 mmol) in 0.5 ml of dry 1,4-dioxane was added drop-wise again and the reaction mixture stirred at 40° C. for overnight. The reaction mixture was then to diluted with dichloromethane and washed with saturated sodium bicarbonate solution. The organic phase was filtered on a phase separator and concentrated. The crude was purified with HPLC-MS preparative method A. 13 mg (0.025 mmol; 33.5% yield) of the desired compound were obtained.

LC-MS method: E

Retention time: 5.54 min

[M+H]=523

Example 77

Table 1

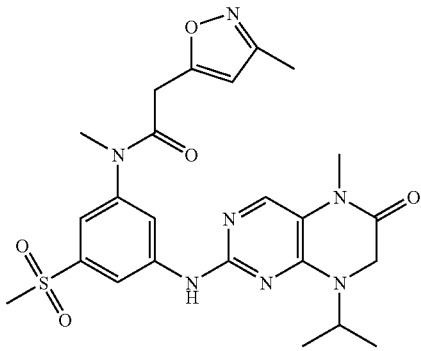 [SMILES: Cc1cc(CC(=O)N(C)c2cc(Nc3ncc4c(n3)N(C(C)C)CC(=O)N4C)cc(S(C)(=O)=O)c2)on1]

8-Isopropyl-2-(3-(methylsulfonyl)-5-methylamino-phenylamino)-5-methyl-7,8-dihydro-5H-pteridin-6-one (30 mg; 0.074 mmol) and 3-methyl-5-isoxazoleacetic acid (10.4 mg; 0.074 mmol), were dissolved in 1 ml of dry dichloromethane. The reaction mixture was cooled to 0° C. and N,N'-dicyclohexylcarbodiimide (37.18; 0.185 mmol) in 1 ml of dry dichloromethane was added drop-wise. The reaction mixture was allowed to reach room temperature and maintained at room temperature for 48 h. The precipitated formed was filtered and the solution concentrated in vacuo. The crude was treated with hexane/isopropyl ether and the solid filtered and dried in vacuo. 39 mg (0.074 mmol; 99% yield) of the desired compound were obtained.

LC-MS method: Purification method B

Retention time: 5.9 min

[M+H]=528

Scheme 12

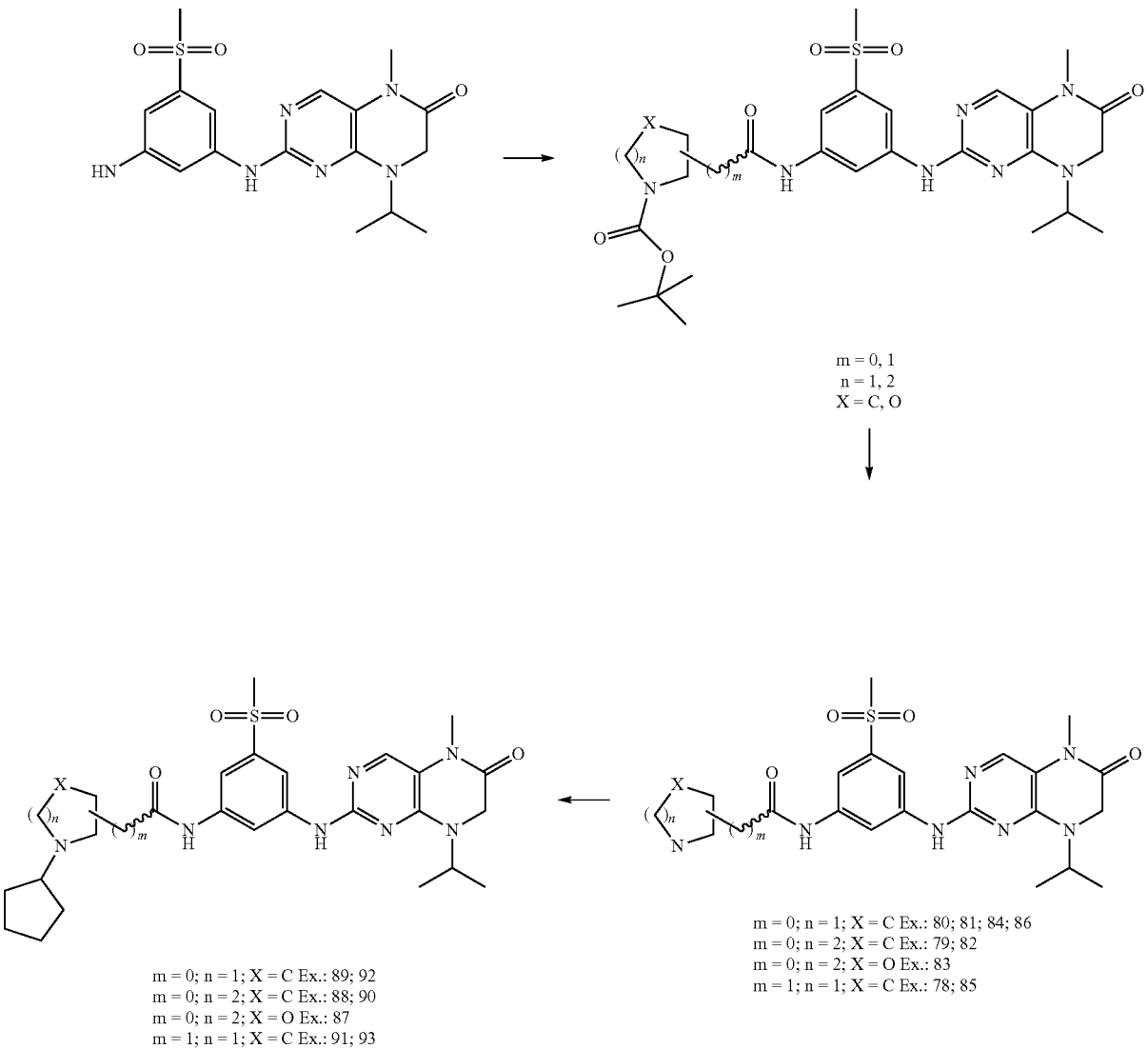

Preparation of (R)-3-[3-(8-isopropyl-5-methyl-6-oxo-5,6,7,8-tetrahydro-pteridin-2-ylamino)-5-(methylsulfonyl)-phenylcarbamoyl]-methyl]-pyrrolidine-1-carboxylic acid tert-butyl ester (R)-3-carboxymethyl-pyrrolidine-1-carboxylic acid tert butyl ester (132 mg; 0.576 mmol), TBTU (197 mg; 0.615 mmol) DIPEA (197 ul 1.15 mmol) in 5 ml of DMF were stirred at room temperature for 30 min. 2-(3-Amino-5-methanesulfonyl-phenylamino)-8-isopropyl-5-methyl-7,8-dihydro-5H-pteridin-6-one (150 mg; 0.384 mmol) was added and the reaction mixture was warmed to 50° C. overnight. The reaction mixture was diluted with dichloromethane and washed with water. The to organic phase was dried on MgSO$_4$, concentrated in vacuo and the crude obtained treated with (iPr)$_2$O and acetone. The solid obtained was filtered and dried in vacuo. 195 mg (0.324 mmol; 84% yield) of the desired compound were obtained.

Preparation of (S)-3-[[3-(8-isopropyl-5-methyl-6-oxo-5,6,7,8-tetrahydro-pteridin-2-ylamino)-5-(methylsulfonyl)-phenylcarbamoyl]-methyl]-pyrrolidine-1-carboxylic acid tert-butyl ester The (S)-enantiomer was prepared with the same procedure used for the (R)-enantiomer and described in Scheme 12 starting from (S)-3-carboxymethyl-pyrrolidine-1-carboxylic acid tert butyl ester (132 mg; 0.576 mmol) and 2-(3-Amino-5-(methylsulfonyl)-phenylamino)-8-isopropyl-5-methyl-7,8-dihydro-5H-pteridin-6-one (150 mg; 0.384 mmol), 190 mg (0.316 mmol; 82% yield) of product were obtained.

The following carboxylic acid tert-butyl esters were prepared with the same procedure described for the preparation of (R) and (S)-3-[[3-(8-isopropyl-5-methyl-6-oxo-5,6,7,8-tetrahydro-pteridin-2-ylamino)-5-(methylsulfonyl)-phenylcarbamoyl]-methyl]-pyrrolidine-1-carboxylic acid tert-butyl esters and reported in Scheme 12.

Preparation of (R)-3-[3-(8-isopropyl-5-methyl-6-oxo-5,6,7,8-tetrahydro-pteridin-2-ylamino)-5-(methylsulfonyl)-phenylcarbamoyl]-pyrrolidine-1-carboxylic acid tert-butyl ester Starting from (R)-Pyrrolidine-1,3-dicarboxylic acid tert butyl ester (165 mg; 0.768 mmol) and 2-(3-amino-5-(methylsulfonyl)-phenylamino)-8-isopropyl-5-methyl-7,8-dihydro-5H-pteridin-6-one (150 mg; 0.384 mmol), 27 mg (0.046 mmol; 12% yield) of the desired compound were obtained.

Preparation of (S)-3-[3-(8-isopropyl-5-methyl-6-oxo-5,6,7,8-tetrahydro-pteridin-2-ylamino)-5-(methylsulfonyl)-phenylcarbamoyl]-pyrrolidine-1-carboxylic acid tert-butyl ester The (S)-enantiomer was prepared with the same procedure used for the (R)-enantiomer and described in Scheme 12 starting from (S)pyrrolidine-1,3-dicarboxylic acid tert butyl ester (33 mg; 0.154 mmol) and 2-(3-amino-5-(methylsulfonyl)-phenylamino)-8-isopropyl-5-methyl-7,8-dihydro-5H-pteridin-6-one (40 mg; 0.102 mmol), 19 mg (0.032 mmol; 32% yield) of the desired compound were obtained.

Preparation of (R)-2-[3-(8-isopropyl-5-methyl-6-oxo-5,6,7,8-tetrahydro-pteridin-2-ylamino)-5-(methylsulfonyl)-phenylcarbamoyl]-pyrrolidine-1-carboxylic acid tert-butyl ester Starting from (R)pyrrolidine-1,2-dicarboxylic acid tert butyl ester (74 mg; 0.346 mmol) and 2-(3-amino-5-(methylsulfonyl)-phenylamino)-8-isopropyl-5-methyl-7,8-dihydro-5H-pteridin-6-one (90 mg; 0.230), 40 mg (0.068 mmol; 29.5% yield) of the desired compound were obtained.

Preparation of (S)-2-[3-(8-isopropyl-5-methyl-6-oxo-5,6,7,8-tetrahydro-pteridin-2-ylamino)-5-(methylsulfonyl)-phenylcarbamoyl]-pyrrolidine-1-carboxylic acid tert-butyl ester The (S)-enantiomer was prepared with the same procedure used for the (R)-enantiomer and described in Scheme 12 starting from (S)pyrrolidine-1,2-dicarboxylic acid tert butyl ester (44 mg; 0.204 mmol) and 2-(3-amino-5-(methylsulfonyl)-phenylamino)-8-isopropyl-5-methyl-7,8-dihydro-5H-pteridin-6-one (40 mg; 0.102), 15.2 mg (0.026 mmol; 25.2% yield) of the desired compound were obtained.

Preparation of (R)-3-[3-(8-isopropyl-5-methyl-6-oxo-5,6,7,8-tetrahydro-pteridin-2-ylamino)-5-(methylsulfonyl)-phenylcarbamoyl]-piperidine-1-carboxylic acid tert-butyl ester Starting from (R)-piperidine-1-3-dicarboxylic acids 1-tert-butyl ester (70 mg; 0.307 mmol) and 2-(3-amino-5-(methylsulfonyl)-phenylamino)-8-isopropyl-5-methyl-7,8-dihydro-5H-pteridin-6-one (80 mg; 0.205 mmol), 46 mg (0.076 mmol; 37% yield) of the desired compound were obtained.

Preparation of (S)-3-[3-(8-isopropyl-5-methyl-6-oxo-5,6,7,8-tetrahydro-pteridin-2-ylamino)-5-(methylsulfonyl)-phenylcarbamoyl]-piperidine-1-carboxylic acid tert-butyl ester The (S)-enantiomer was prepared with the same procedure used for the (R)-enantiomer and described in Scheme 12 starting from (S)-piperidine-1-3-dicarboxylic acids 1-tert-butyl ester (70 mg; 0.307 mmol) and 2-(3-amino-5-(methylsulfonyl)-phenylamino)-8-isopropyl-5-methyl-7,8-dihydro-5H-pteridin-6-one (80 md; 0.205 mmol), 100 mg (0.166 mmol; 81% yield) of the desired compound were obtained.

Preparation of 2-[3-(8-isopropyl-5-methyl-6-oxo-5,6,7,8-tetrahydro-pteridin-2-ylamino)-5-(methylsulfonyl)-phenylcarbamoyl]-piperidine-1-carboxylic acid tert-butyl ester Starting from piperidine-1,2-dicarboxylic acid 1-tert-butyl ester (176 mg; 0.768 mmol) and 2-(3-amino-5-(methylsulfonyl)-phenylamino)-8-isopropyl-5-methyl-7,8-dihydro-5H-pteridin-6-one (200 mg; 0.512 mmol), 45 mg (0.074 mmol; 15% yield) of the desired compound were obtained.

Preparation of 2-[3-(8-isopropyl-5-methyl-6-oxo-5,6,7,8-tetrahydro-pteridin-2-ylamino)-5-(methylsulfonyl)-phenylcarbamoyl]-morpholine-4-carboxylic acid tert-butyl ester Starting from morpholine-2,4-dicarboxylic acid 4-tert-butyl ester (70 mg; 0.307 mmol) and 2-(3-amino-5-(methylsulfonyl)-phenylamino)-8-isopropyl-5-methyl-7,8-dihydro-5H-pteridin-6-one (80 md; 0.205 mmol), 70 mg (0.116 mmol; 57% yield) of the desired compound were obtained.

Example 78

Table 1

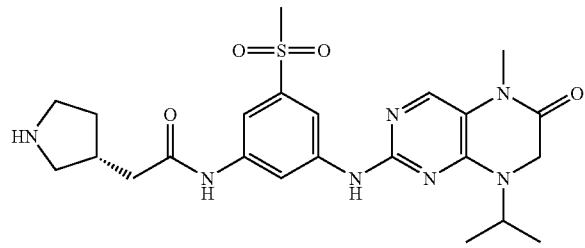 [SMILES: CC(C)N1CC(=O)N(C)c2cnc(Nc3cc(NC(=O)C[C@H]4CCNC4)cc(S(C)(=O)=O)c3)nc21]

(R)-3-[[3-(8-isopropyl-5-methyl-6-oxo-5,6,7,8-tetrahydro-pteridin-2-ylamino)-5-(methylsulfonyl)-phenylcarbamoyl]-methyl]-pyrrolidine-1-carboxylic acid tert-butyl ester (180 mg; 0.299 mmol) was diluted in 4 ml of 4M HCl in 1,4-dioxane and to stirred for 6 h. The reaction mixture was concentrated in vacuo. The free amine was obtained after loading the corresponding hydrochloride on a SCX-cartridge and recovering with MeOH/ammonia solution. 130 mg (0.259 mmol; 87% yield) of the desired compound were obtained.

LC-MS method: C

Retention time: 4.23 min

[M+H]=502

The following example was prepared with the same procedure described for the preparation of example 78 and reported in Scheme 12.

Example 80

Table 1

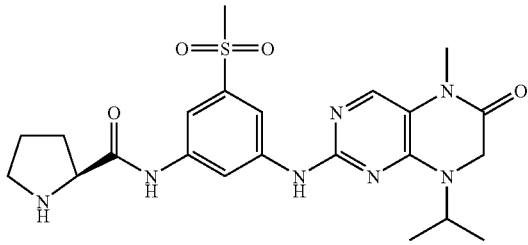 [SMILES: CC(C)N1CC(=O)N(C)c2cnc(Nc3cc(NC(=O)[C@@H]4CCCN4)cc(S(C)(=O)=O)c3)nc21]

Starting from (S)-2-[3-(8-isopropyl-5-methyl-6-oxo-5,6,7,8-tetrahydro-pteridin-2-ylamino)-5-(methylsulfonyl)-phenylcarbamoyl]-pyrrolidine-1-carboxylic acid tert-butyl ester (10 mg; 0.017 mmol), 8 mg (0.015 mmol; 90% yield) of the desired compound were obtained.

LC-MS method: A

Retention time: 5.18 min

[M+H]=488

Example 91

Table 1

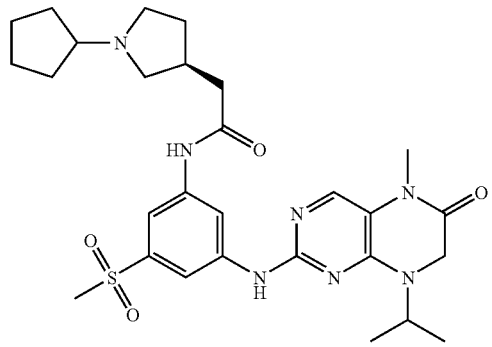 [SMILES: CC(C)N1CC(=O)N(C)c2cnc(Nc3cc(NC(=O)C[C@@H]4CCN(C5CCCC5)C4)cc(S(C)(=O)=O)c3)nc21]

N-[3-(8-isopropyl-5-methyl-6-oxo-5,6,7,8-tetrahydro-pteridin-2-ylamino)-5-(methylsulfonyl)-phenyl]-2-(S)-pyrrolidin-3-yl-acetamide (40 mg; 0.080 mmol), sodium triacetoxyborohydride (34 mg; 0.159 mmol) and cyclopentanone (0.035 ml; 0.399 mmol) were mixed in 5 ml of dichloromethane. The reaction mixture was stirred at 40° C. overnight.

The reaction mixture was diluted in dichloromethane/methanol. The solid obtained after loading the reaction mixture on a SCX-cartridge and recovering with MeOH/ammonia solution was treated with methanol/isopropyl ether. The precipitate was filtered and dried in vacuo. 32 mg (0.056 mmol; 70% yield) of the desired compound were obtained.

LC-MS method: A

Retention time: 6.48 min

[M+H]=570

The following examples were prepared with the same procedure described for the preparation of example 91 and reported in Scheme 12.

Example 93

Table 1

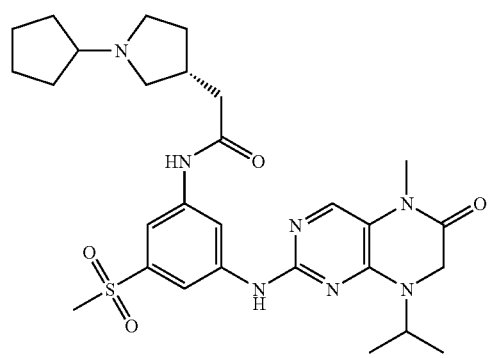 [SMILES: CC(C)N1CC(=O)N(C)c2cnc(Nc3cc(NC(=O)C[C@H]4CCN(C5CCCC5)C4)cc(S(C)(=O)=O)c3)nc21]

Starting from N-[3-(8-isopropyl-5-methyl-6-oxo-5,6,7,8-tetrahydro-pteridin-2-ylamino)-5-(methylsulfonyl)-phenyl]-2-(S)-pyrrolidin-3-yl-acetamide (45 mg; 0.090 mmol), 32.8 mg (0.057 mmol; 64% yield) of the desired compound were obtained.

LC-MS method: A

Retention time: 6.69 min

[M+H]=570

Example 89

Table 1

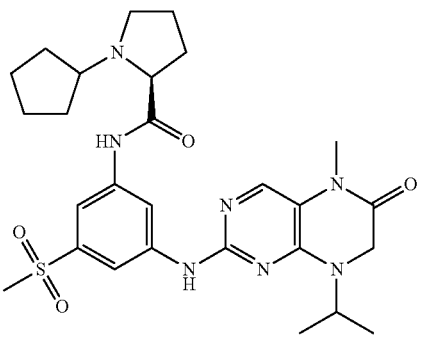 [SMILES: CC(C)N1CC(=O)N(C)c2cnc(Nc3cc(NC(=O)[C@@H]4CCCN4C4CCCC4)cc(S(C)(=O)=O)c3)nc21]

Starting from (S)-pyrrolidine-2-carboxylic acid [3-(8-isopropyl-5-methyl-6-oxo-5,6,7,8-tetrahydro-pteridin-2-ylamino)-5-(methylsulfonyl)-phenyl]-amide (33 mg; 0.063 mmol). 16.8 mg (0.030 mmol; 48% yield) of the desired compound were obtained.
LC-MS method: A
Retention time: 5.1 min
[M+H]=556

Scheme 13

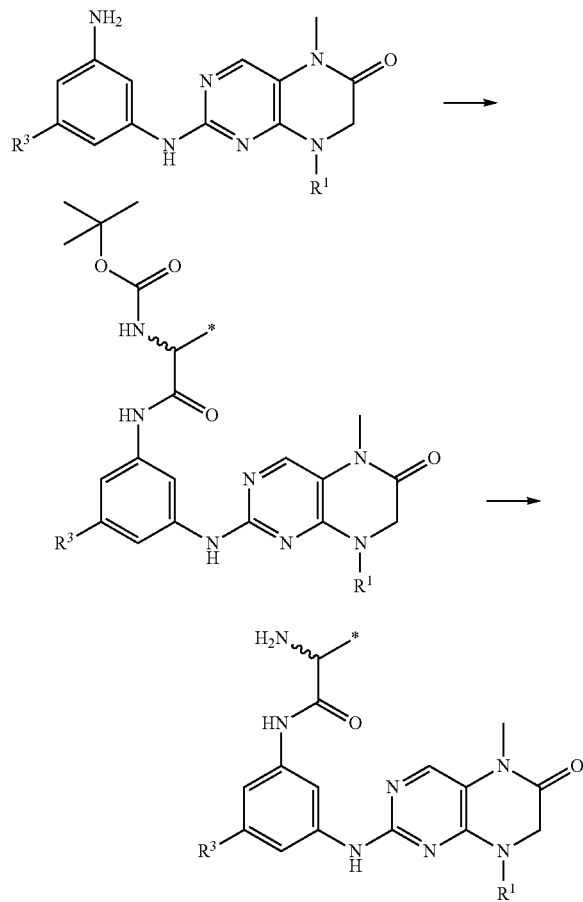

Ex.: 94; 95; 96.

Preparation of [(R)-[3-isopropyl-5-methyl-6-oxo-5,6,7,8-tetrahydro-pteridin-2-ylamino)-5-(methylsulfonyl)-phenylcarbamoyl]-phenyl-methyl]-carbamic acid tert-butyl ester (R)-Tert-butoxycarbonylamino-phenyl-acetic acid (36 mg; 0.154 mmol), TBTU (53 to mg; 0.164 mmol) DIPEA (52 ul; 0.307 mmol)) in 1 ml of DMF were stirred at room temperature for 30 min. 2-(3-Amino-5-(methylsulfonyl)-phenylamino)-8-isopropyl-5-methyl-7,8-dihydro-5H-pteridin-6-one (40 mg; 0.102) was added and the reaction mixture was warmed to 50° C. overnight. The reaction mixture was diluted with dichloromethane and washed with water. The organic phase was filtered on a phase separator and, concentrated. The crude obtained treated with (iPr)₂O and acetone. The solid obtained was filtered and dried in vacuo. 18 mg (0.029 mmol; 28% yield) of the desired compound were obtained.

Preparation of [(R)-cyclohexyl-[3-(8-isopropyl-5-methyl-6-oxo-5,6,7,8-tetrahydro-pteridin-2-ylamino)-5-(methylsulfonyl)-phenylcarbamoyl]-methyl]-carbamic acid tert-butyl ester Starting from (R)-tert-butoxycarbonylamino-cyclohexyl-acetic acid (31.6 mg; 0.123 mmol) and 2-(3-amino-5-(methylsulfonyl)-phenylamino)-8-isopropyl-5-methyl-7,8-dihydro-5H-pteridin-6-one (40 mg; 0.102), 11.3 mg (0.018 mmol; 17.5% yield) of the desired compound were obtained.

Example 94

Table 1

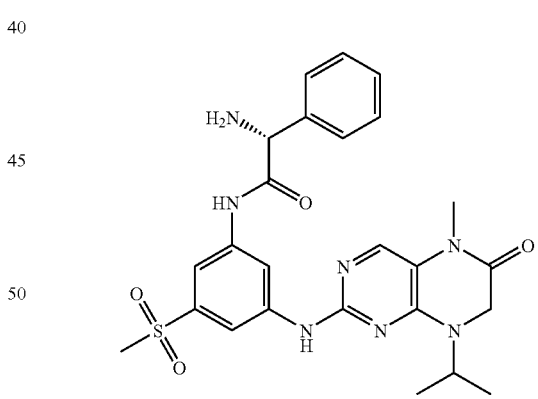

[(R)-[3-Isopropyl-5-methyl-6-oxo-5,6,7,8-tetrahydro-pteridin-2-ylamino)-5-(methylsulfonyl)-phenylcarbamoyl]-phenyl-methyl]-carbamic acid tert-butyl ester (18 mg; 0.029 mmol) was diluted in 1 ml of 4M HCl in 1,4-dioxane and stirred for 6 h. The organic phase was concentrated and the solid dried in vacuo. 14.2 mg (0.027 mmol; 94% yield) of the desired compound were obtained.
LC-MS method: A
Retention time: 5.59 min
[M+H]=524

Example 96

Table 1

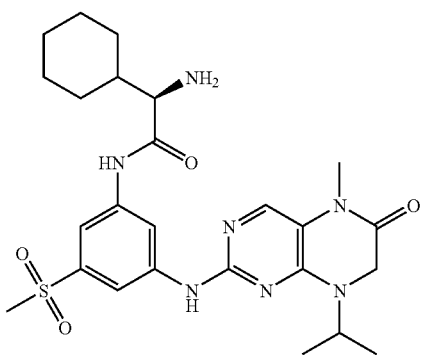 [SMILES: CC(C)N1CC(=O)N(C)c2cnc(Nc3cc(NC(=O)[C@H](N)C4CCCCC4)cc(S(C)(=O)=O)c3)nc21]

[(R)-Cyclohexyl-[3-(8-isopropyl-5-methyl-6-oxo-5,6,7,8-tetrahydro-pteridin-2-ylamino)-5-methylsulfonyl-phenyl-carbamoyl]-methyl]-carbamic acid tert-butyl ester (11 mg; 0.018 mmol) was diluted in 1 ml of 4M HCl in 1,4-dioxane and stirred for 6 h. The organic phase was concentrated and the solid dried in vacuo. 9 mg (0.017 mmol; 95% yield) of the desired compound were obtained.

LC-MS method: C
Retention time: 4.93 min
[M+H]=530

Scheme 14

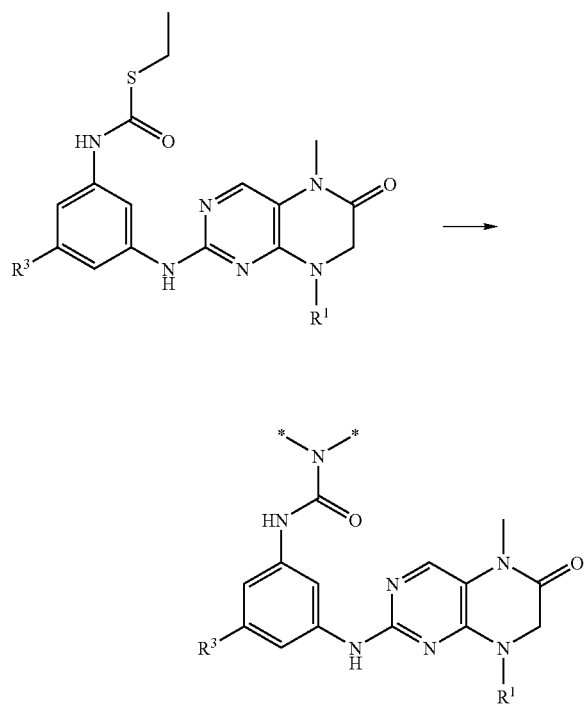

Ex.: 97; 98; 99; 100; 101; 102; 103; 104; 105; 106; 107; 108; 109; 112; 116; 123; 124; 130; 131; 132; 134; 133; 11; 12.

Example 97

Table 1

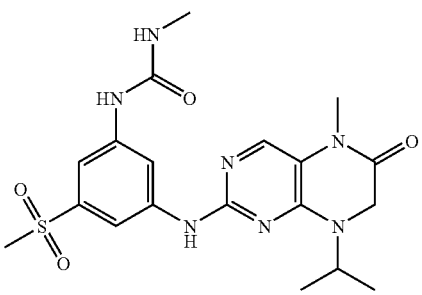 [SMILES: CNC(=O)Nc1cc(Nc2ncc3c(n2)N(C(C)C)CC(=O)N3C)cc(S(C)(=O)=O)c1]

[3-(8-Isopropyl-5-methyl-6-oxo-5,6,7,8-tetrahydro-pteridin-2-ylamino)-5-(methylsulfonyl)-phenyl]-thiocarbamic acid ethyl ester (50 mg; 0.104 mmol) was dissolved in 1 ml of dry DMF. A solution of methylamine (2M in THF; 0.104 ml; 0.209 mmol) was added. The reaction mixture was stirred at 70° C. overnight, then it was diluted with dichloromethane and washed with water. The organic phase was filtered on a phase separator and concentrated. The crude was treated with isopropyl ether/ethanol. The precipitated formed was filtered and dried in vacuo. 12 mg (0.017 mmol; 95% yield) of the desired compound were obtained.

LC-MS method: G
Retention time: 3.57 min
[M+H]=448

The following examples were prepared with the same procedure described for the preparation of example 97 and reported in Scheme 14.

Example 109

Table 1

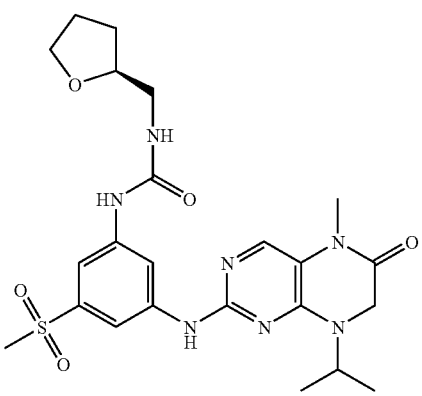 [SMILES: CC(C)N1CC(=O)N(C)c2cnc(Nc3cc(NC(=O)NC[C@@H]4CCCO4)cc(S(C)(=O)=O)c3)nc21]

Starting from [3-(8-isopropyl-5-methyl-6-oxo-5,6,7,8-tetrahydro-pteridin-2-ylamino)-5-(methylsulfonyl)-phenyl]-thiocarbamic acid ethyl ester (40 mg; 0.084 mmol) and (S)-tetrahydrofurfurylamine (16.9 mg; 0.167 mmol), 22.2 mg (0.043 mmol; 51% yield) of the desired compound were obtained.

LC-MS method: B
Retention time: 5.77 min
[M+H]=518

Example 116

Table 1

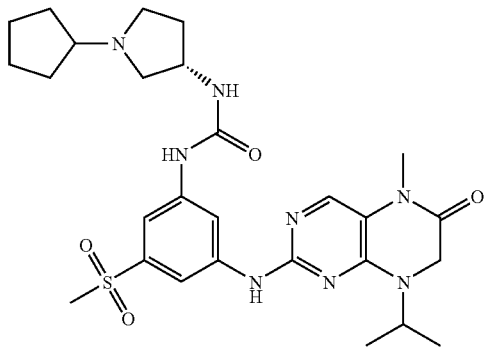 [SMILES: CC(C)N1CC(=O)N(C)c2cnc(Nc3cc(NC(=O)N[C@H]4CCN(C5CCCC5)C4)cc(S(C)(=O)=O)c3)nc21]

Starting from [3-(8-isopropyl-5-methyl-6-oxo-5,6,7,8-tetrahydro-pteridin-2-ylamino)-5-(methylsulfonyl)-phenyl]-thiocarbamic acid ethyl ester (40 mg; 0.084 mmol), (S)-cyclopentyl-pyrrolidin-3-ylamine di-hydrochloride (38 mg; 0.167 mmol) and triethylamine (0.023; 0.176 mmol), 11.2 mg (0.020 mmol; 23.5% yield) of the desired compound were obtained.

LC-MS method: E
Retention time: 4.87 min
[M+H]=571

Example 123

Table 1

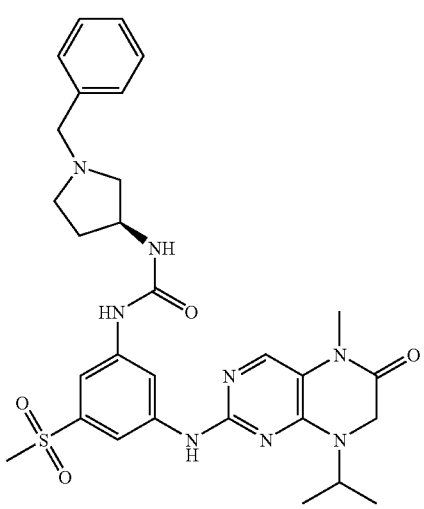 [SMILES: CC(C)N1CC(=O)N(C)c2cnc(Nc3cc(NC(=O)N[C@H]4CCN(Cc5ccccc5)C4)cc(S(C)(=O)=O)c3)nc21]

Starting from [3-(8-isopropyl-5-methyl-6-oxo-5,6,7,8-tetrahydro-pteridin-2-ylamino)-5-(methylsulfonyl)-phenyl]-thiocarbamic acid ethyl ester (40 mg; 0.084 mmol) and (S)-1-benzyl-3-aminopyrrolidine (0.029 ml; 0.167 mmol), 35.9 mg (0.061 mmol; 72.5% yield) of the desired compound were obtained.

LC-MS method: B
Retention time: 4.66 min
[M+H]=593

Scheme 15

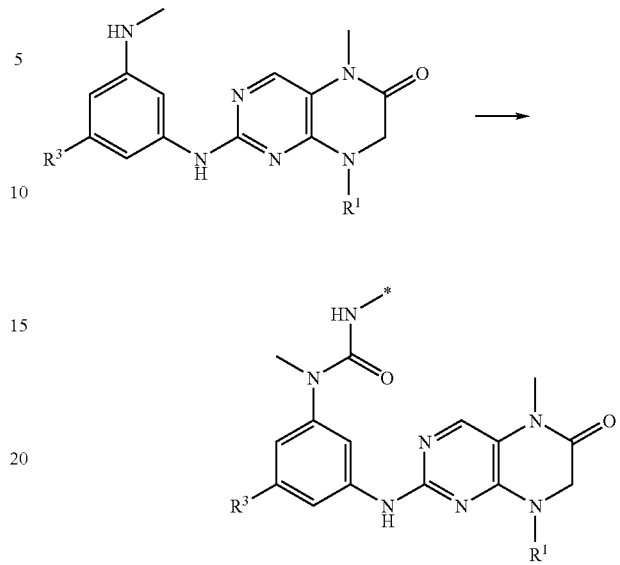

Ex.: 110; 111; 115.

Example 128

Table 1

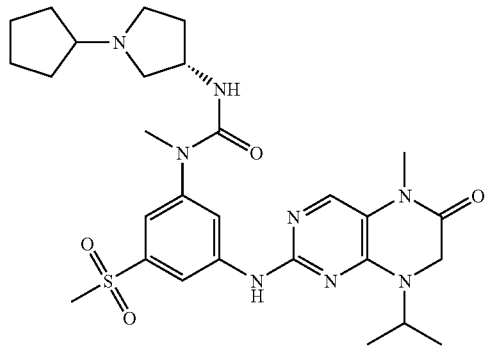 [SMILES: CC(C)N1CC(=O)N(C)c2cnc(Nc3cc(N(C)C(=O)N[C@H]4CCN(C5CCCC5)C4)cc(S(C)(=O)=O)c3)nc21]

(S)-1-Cyclopentyl-pyrrolidin-3-ylamine (53 mg; 0.237 mmol) was dissolved in 1 ml of dry DMF. 1,1'-Carbonyldiimidazole (70 mg; 0.436 mmol) and diisopropylethylamine (0.044 ml; 0.257 mmol) were added. The reaction mixture was warmed to 70° C., then, 8-isopropyl-2-(3-(methylsulfonyl)-5-methylamino-phenylamino)-5-methyl-7,8-dihydro-5H-pteridin-6-one (80 mg; 0.198 mmol) was added. The reaction mixture was stirred at 70° C. overnight. The reaction mixture was concentrated and the crude was purified with HPLC_MS preparative method C. 16 mg (0.027 mmol; 14% yield) of the desired compound were obtained.

LC-MS method: A
Retention time: 4.21 min
[M+H]=585

Example 129

Table 1

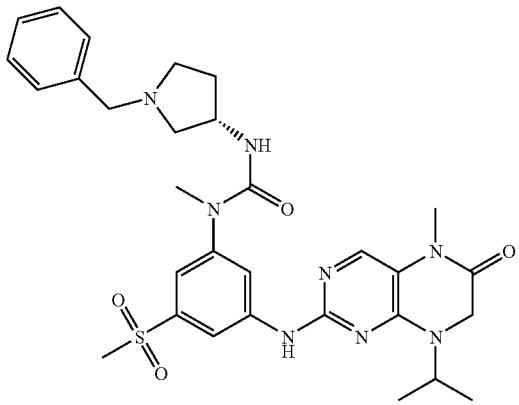 [SMILES: CC(C)N1CC(=O)N(C)c2cnc(Nc3cc(N(C)C(=O)N[C@H]4CCN(Cc5ccccc5)C4)cc(S(C)(=O)=O)c3)nc21]

Following the same procedure used for ex. 128, starting from (S)-1-benzyl-3-amino-pyrrolidine (41 mg; 0.237 mmol) and 8-isopropyl-2-(3-(methylsulfonyl)-5-methylamino-phenylamino)-5-methyl-7,8-dihydro-5H-pteridin-6-one (80 mg; 0.198 mmol), 2 mg (0.003 mmol; 2% yield) of the desired compound were obtained.

LC-MS method: A
Retention time: 4.33 min
[M+H]=607 acid ethyl ester (150 mg; 0.313 mmol) was dissolved in 1 ml of dry DMF, tert-butyl-cis-4-aminocyclohexylcarbamate (201 mg; 0.940 mmol) was added. The reaction mixture was stirred at 70° C., overnight, then, it was diluted with water. The precipitated formed was filtered, washed with water and dried in vacuo. 196 mg (0.311 mmol; 99% yield) of the desired compound to were obtained.

Example 114

Table 1

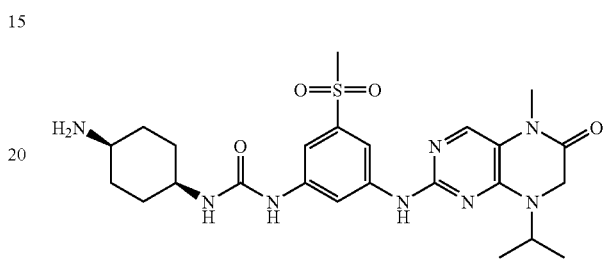

4-[3-[3-(8-Isopropyl-5-methyl-6-oxo-5,6,7,8-tetrahydro-pteridin-2-ylamino)-5-(methylsulfonyl)-phenyl]-ureido]-cyclohexyl)-carbamic acid tert butyl ester (25 mg; 0.040 mmol) was diluted in 1 ml of 1,4-dioxane (4M HCl) and stirred for 6 h.

The organic phase was concentrated. The free amine was obtained after loading the corresponding hydrochloride on a Scheme 16

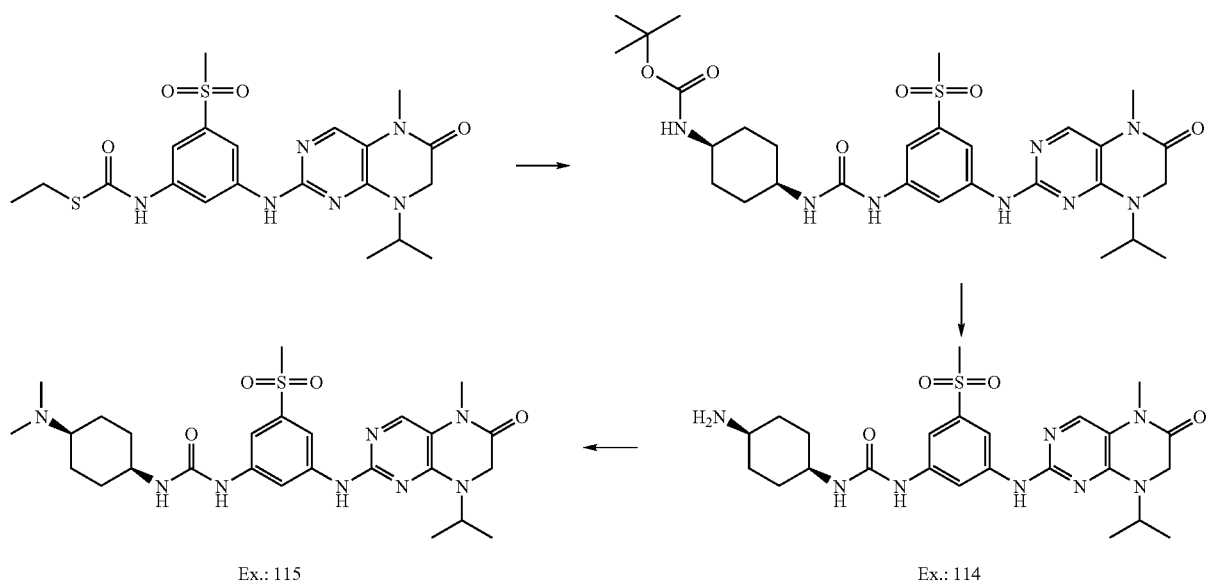

Preparation of (4-[3-[3-(8-isopropyl-5-methyl-6-oxo-5,6,7,8-tetrahydro-pteridin-2-ylamino)-5-(methylsulfonyl)-phenyl]-ureido]-cyclohexyl)-carbamic acid tert butyl ester

[3-(8-Isopropyl-5-methyl-6-oxo-5,6,7,8-tetrahydro-pteridin-2-ylamino)-5-(methylsulfonyl)-phenyl]-thiocarbamic SCX-cartridge and recovering with MeOH/ammonia solution. The crude obtained was treated with isopropyl ether, filtered and dried in vacuo. 19 mg (0.036 mmol; 90% yield) of the desired compound were obtained.

LC-MS method: A
Retention time: 4.14 min
[M+H]=531

Example 115

Table 1

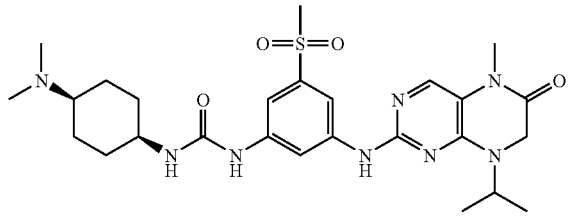 [SMILES: CC(C)N1CC(=O)N(C)c2cnc(Nc3cc(NC(=O)N[C@H]4CC[C@@H](N(C)C)CC4)cc(S(C)(=O)=O)c3)nc21]

1-(4-Amino-cyclohexyl)-3-[3-(8-isopropyl-5-methyl-6-oxo-5,6,7,8-tetrahydro-pteridin-2-ylamino)-5-(methylsulfonyl)-phenyl]-urea (40 mg; 0.075 mmol), sodium triacetoxyborohydride (31 mg; 0.150 mmol) and formaldehyde (0.030 ml; 0.375 mmol) were dissolved in 5 ml of dry dichloromethane and the reaction mixture was stirred at 40'° C. overnight. Sodium triacetoxyborohydride (31 mg; 0.150 mmol) and formaldehyde (0.030 ml; 0.375 mmol) were added again to increase the conversion and the reaction mixture was stirred at 40° C. overnight. The reaction mixture was cooled to room temperature, diluted with dichloromethane/methanol to and loaded on a SCX-cartridge. The free amine was obtained after loading the corresponding hydrochloride on a SCX-cartridge and recovering with MeOH/ammonia solution. The crude obtained was treated with isopropyl ether/acetone, the precipitate filtered and dried in vacuo. 31.4 mg (0.056 mmol; 75% yield) of the desired compound were obtained.

LC-MS method: A
Retention time: 5.5 min
[M+H]=559

Preparation of (R)-2-[3-[3-8-isopropyl-5-methyl-6-oxo-5,6,7,8-tetrahydro-pteridin-2-ylamino)-5-(methylsulfonyl)-phenyl]-ureidomethyl]-pyrrolidine-1-carboxylic acid tert butyl ester

[3-(8-Isopropyl-5-methyl-6-oxo-5,6,7,8-tetrahydro-pteridin-2-ylamino)-5-(methylsulfonyl)-phenyl]-thiocarbamic acid ethyl ester (500 mg; 1.045 mmol) was dissolved in 2 ml of dry DMF. (R)-2-(aminomethyl)-pyrrolidine-1-carboxylic acid to tert-butyl ester (418 mg; 2.089 mmol) was added. The reaction mixture was stirred at 70° C., overnight, then, it was diluted with water/methanol. The precipitated formed was dried in vacuo. 570 mg (0.924 mmol; 88.5% yield) of the desired compound were obtained.

Preparation of (S)-2-[3-[3-8-isopropyl-5-methyl-6-oxo-5,6,7,8-tetrahydro-pteridin-2-ylamino)-5-(methylsulfonyl)-phenyl]-ureidomethyl]-pyrrolidine-1-carboxylic acid tert butyl ester The (S)-enantiomer was prepared following the same procedure used for the (R)-enantiomer and described in scheme 17 starting from [3-(8-isopropyl-5-methyl-6-oxo-5,6,7,8-tetrahydro-pteridin-2-ylamino)-5-(methylsulfonyl)-phenyl]-thiocarbamic acid ethyl ester (500 mg; 1.045 mmol) and (S)-2-(aminomethyl)-pyrrolidine-1-carboxylic acid tert-butyl ester (418 mg; 2.089 mmol). 500 mg (0.783 mmol; 75% yield) of the desired compound were obtained.

Scheme 17

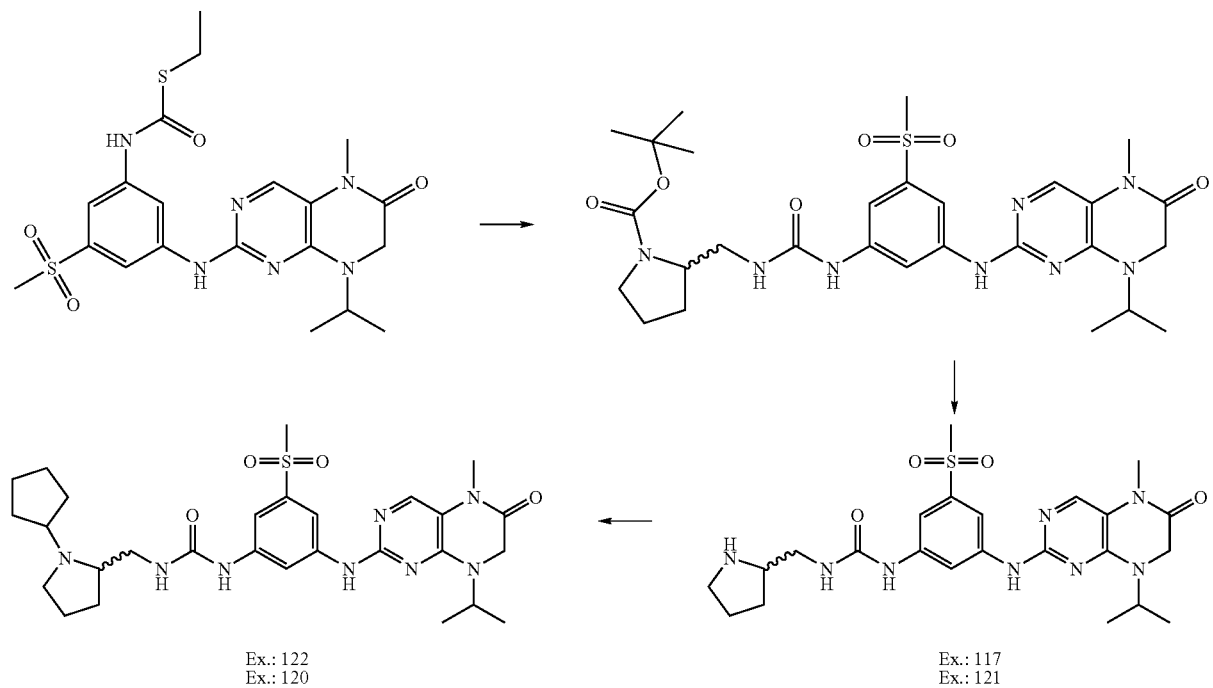

Ex.: 122
Ex.: 120

Ex.: 117
Ex.: 121

Example 117

Table 1

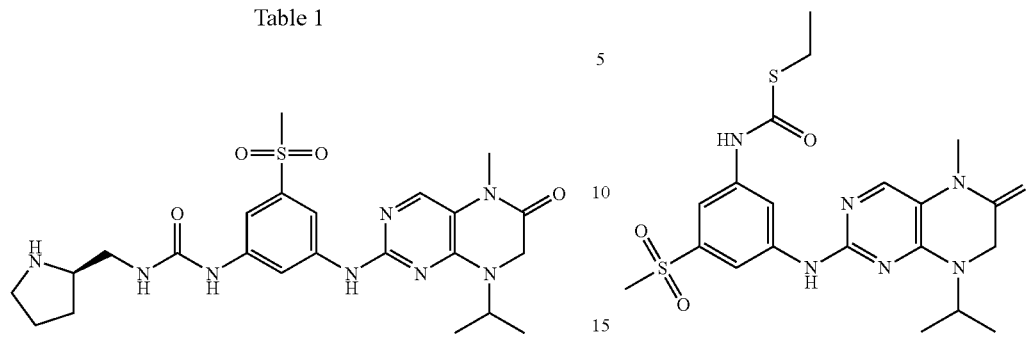

(R)-2-[3-[3-8-Isopropyl-5-methyl-6-oxo-5,6,7,8-tetrahydro-pteridin-2-ylamino)-5-(methylsulfonyl)-phenyl]-ureidomethyl]-pyrrolidine-1-carboxylic acid tert butyl ester (570 mg; 0.939 mmol) was dissolved in 10 ml of methanol and 1 ml of HCl 37% were added. The reaction mixture was stirred at room temperature overnight, then it was concentrated in vacuo. The crude was diluted in dichloromethane and washed with saturated sodium bicarbonate solution. The organic phase was filtered on a phase separator, concentrated in vacuo. The crude was treated with isopropyl ether/methanol, filtered and dried in vacuo. 200 mg (0.387 mmol; 37% yield) of the desired compound were obtained.

LC-MS method: E
Retention time: 3.1 min
[M+H]=517

Example 122

Table 1

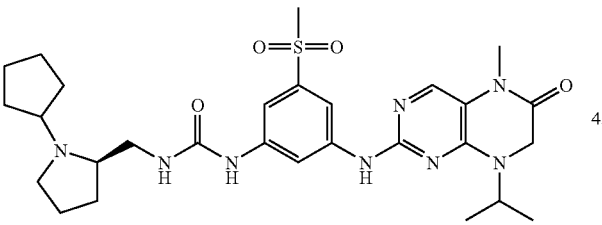

1-[3-[3-8-Isopropyl-5-methyl-6-oxo-5,6,7,8-tetrahydro-pteridin-2-ylamino)-5-(methylsulfonyl)-phenyl]-3-(R)-1-pyrrolidin-2-ylmethyl-urea (50; 0.097 mol) was dissolved in 1 ml of dichloromethane and sodium triacetoxyborohydride (41 mg; 0.194 mmol) was added. Cyclopentanone (0.042 ml; 0.484 mmol) was added to the reaction mixture. The reaction mixture was maintained at room temperature overnight, then it was diluted with dichloromethane and washed with saturated sodium bicarbonate solution. The organic phase was filtered on a phase separator and concentrated. The crude was purified with HPLC-MS preparative method B. 15.5 mg (0.027 mmol; 27% yield) of the desired compound were obtained.

LC-MS method: I
Retention time: 4.84 min
[M+H]=585

Scheme 18

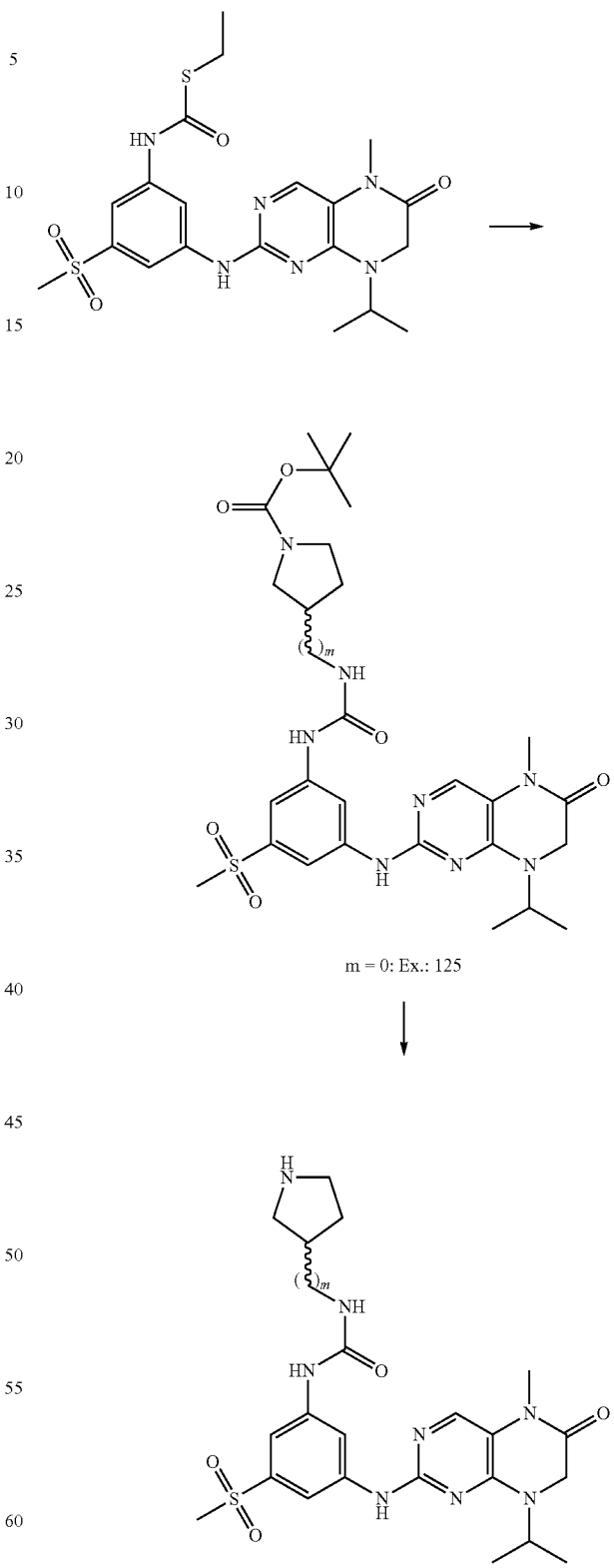

Preparation of (R)-3-[3-[3-8-isopropyl-5-methyl-6-oxo-5,6,7,8-tetrahydro-pteridin-2-ylamino)-5-(methylsulfonyl)-phenyl]-ureidomethyl]-pyrrolidine-1-carboxylic acid tert butyl ester

[3-(8-Isopropyl-5-methyl-6-oxo-5,6,7,8-tetrahydro-pteridin-2-ylamino)-5-(methylsulfonyl)-phenyl]-thiocarbamic acid ethyl ester (500 mg; 1.045 mmol) was dissolved in 2 ml of dry DMF. (R)-3-(Aminomethyl)-pyrrolidine-1-carboxylic acid tert-butyl ester (418 mg; 2.089 mmol) was added. The reaction mixture was stirred at 70° C., overnight, then, it was diluted with water/methanol. The precipitated formed was dried in vacuo. 600 mg (0.973 mmol; 93% yield) of the desired compound were obtained.

Preparation of (S)-3-[3-[3-8-isopropyl-5-methyl-6-oxo-5,6,7,8-tetrahydro-pteridin-2-ylamino)-5-(methylsulfonyl)-phenyl]-ureidomethyl]-pyrrolidine-1-carboxylic acid tert butyl ester The (S)-enantiomer was prepared following the same procedure used for the (R)-enantiomer and described in scheme 18 starting from [3-(8-isopropyl-5-methyl-6-oxo-5,6,7,8-tetrahydro-pteridin-2-ylamino)-5-(methylsulfonyl)-phenyl]-thiocarbamic acid ethyl ester (500 mg; 1.045 mmol) and (S)-3-(aminomethyl)-pyrrolidine-1-carboxylic acid tert-butyl ester (418 mg; 2.089 mmol). 600 mg (0.973 mmol; 93% yield) of the desired compound were obtained.

The carboxylic acid tert butyl esters reported in Scheme 18 were prepared following the same procedure described for the preparation of (R)- and (S)-3-[3-[3-8-isopropyl-5-methyl-6-oxo-5,6,7,8-tetrahydro-pteridin-2-ylamino)-5-(methylsulfonyl)-phenyl]-ureidomethyl]-pyrrolidine-1-carboxylic acid tert butyl esters.

Example 118

Table 1

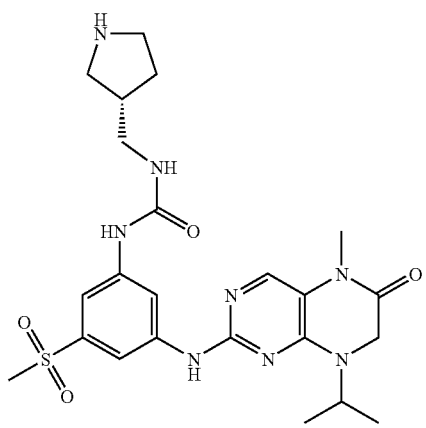 [SMILES: CC(C)N1CC(=O)N(C)c2cnc(Nc3cc(NC(=O)NC[C@H]4CCNC4)cc(S(C)(=O)=O)c3)nc21]

(R)-3-[3-[3-8-Isopropyl-5-methyl-6-oxo-5,6,7,8-tetrahydro-pteridin-2-ylamino)-5-(methylsulfonyl)-phenyl]-ureidomethyl]-pyrrolidine-1-carboxylic acid tert butyl ester (900 mg; 1.459 mmol) was diluted in 10 ml of methanol and 1 ml of HCl 37% were added. The reaction mixture was stirred at room temperature overnight, then it was concentrated in vacuo. The crude was diluted in dichloromethane and washed with saturated sodium bicarbonate solution. The organic phase was filtered on a phase separator, concentrated in vacuo. The crude was treated with isopropyl ether/methanol, filtered and dried in vacuo. 300 mg (0.581 mmol; 40% yield) of the desired compound were obtained.

LC-MS method: E
Retention time: 3.05 min
[M+H]=517

Scheme 19

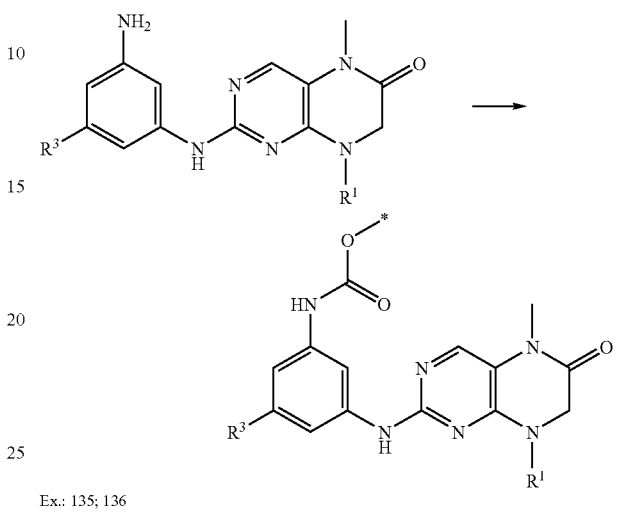

Ex.: 135; 136

Example 135

Table 1

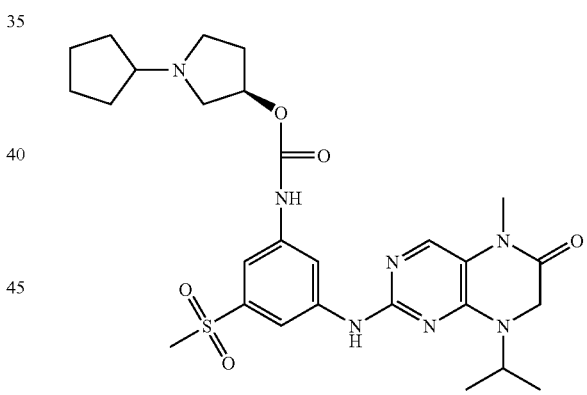

(R)-1-Cyclopentyl-pyrrolidin-3-ol hydrochloride (39 mg; 0.251 mmol) was suspended in 3 ml of NMP, and NaH (10 mg; 0.263 mmol) was added. The reaction mixture was stirred at room temperature for 15 min, then, [3-(8-isopropyl-5-methyl-6-oxo-5,6,7,8-tetrahydro-pteridin-2-yl-amino)-5-(methylsulfonyl)-phenyl]-thiocarbamic acid ethyl ester (60 mg; 0.125 mmol) was added. The reaction mixture was stirred at 70° C. for 5 min. The reaction mixture was diluted with dichloromethane and washed with water. The organic phase was filtered on a Phase separator, treated with a PS-CHO scavenger resin, filtered again and concentrated. The crude obtained was treated with isopropanol and the precipitate formed was filtered and dried in vacuo. 22.5 mg (0.039 mmol; 31% yield) of the desired compound were obtained.

LC-MS method: C
Retention time: 5 min
[M+H]=572

EXAMPLE 136

Table 1

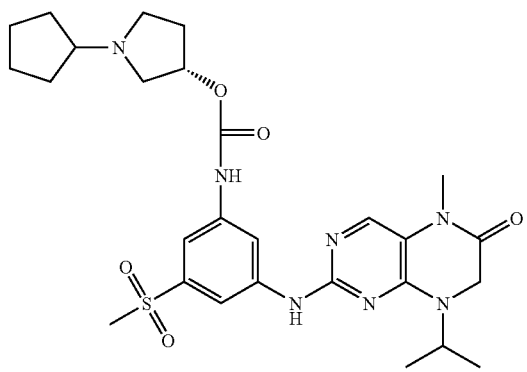 [SMILES: CC(C)N1CC(=O)N(C)c2cnc(Nc3cc(NC(=O)O[C@H]4CCN(C5CCCC5)C4)cc(S(C)(=O)=O)c3)nc21]

Following the same procedure described for ex. 135, starting from (S)-1-cyclopentyl-pyrrolidin-3-ol hydrochloride (39 mg; 0.251 mmol) and [3-(8-isopropyl-5-methyl-6-oxo-5,6,7,8-tetrahydro-pteridin-2-ylamino)-5-(methylsulfonyl)-phenyl]-thiocarbamic acid ethyl ester (60 mg; 0.125 mmol), 24 mg (0.042 mmol; 33.5% yield) of the desired compound were obtained.

LC-MS method: A
Retention time: 3.41 min
[M+H]=572

Scheme 20

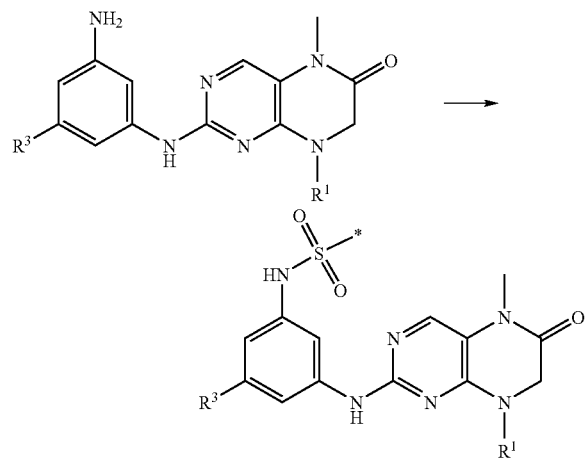

Ex: 8; 9; 10; 137; 138; 139; 140.

EXAMPLE 8

Table 1

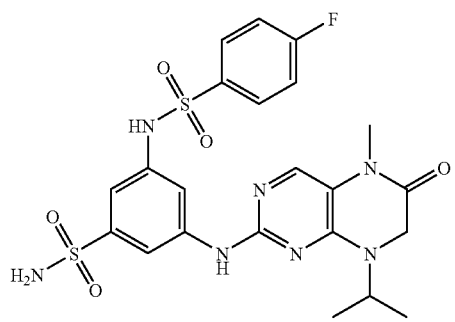 [SMILES: CC(C)N1CC(=O)N(C)c2cnc(Nc3cc(NS(=O)(=O)c4ccc(F)cc4)cc(S(N)(=O)=O)c3)nc21]

3-Amino-5-(8-isopropyl-5-methyl-6-oxo-5,6,7,8-tetrahydro-pteridin-2-ylamino)-benzenesulfonamide (40 mg; 0.104 mmol) was suspended in 0.5 ml of dry to pyridine. The reaction mixture was cooled to 0° C. and 4-fluorobenzenesulfonylchloride (29.8 mg; 0.153 mmol) was added. The reaction mixture was allowed to reach room temperature and maintained at this temperature overnight. The reaction mixture was diluted with dichloromethane and washed with water. The organic phase was separated and dried on a phase separator and concentrated. The crude was purified with HPLC-MS preparative method B. 7.6 mg (0.014 mmol; 52% yield) of the desired compound were obtained.

LC-MS method: A
Retention time: 4.93 min
[M+H]=550

Scheme 21

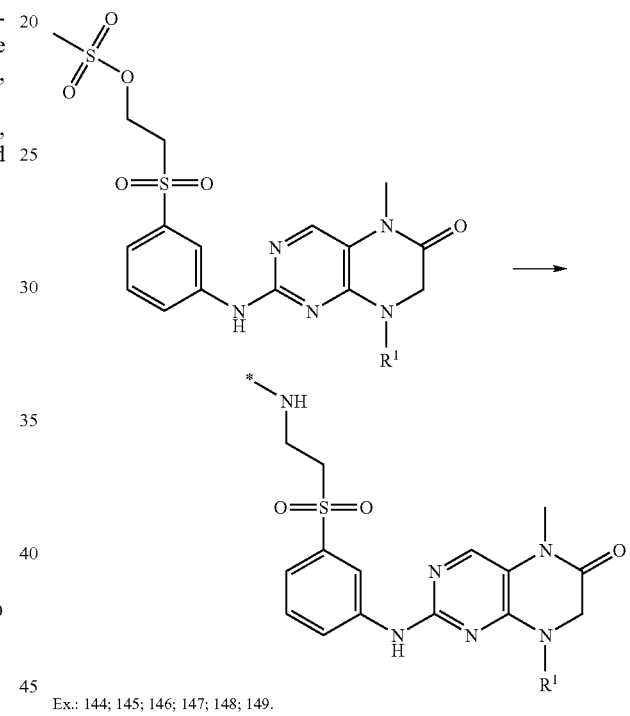

Ex.: 144; 145; 146; 147; 148; 149.

EXAMPLE 144

Table 1

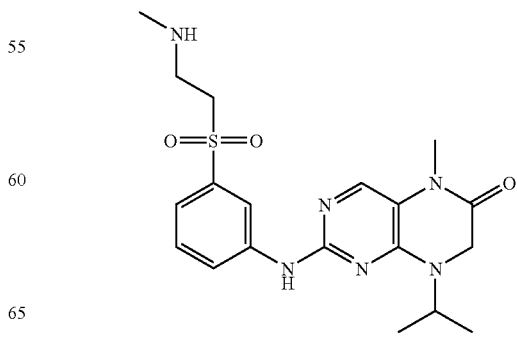

Methanesulfonic acid 2-[3-(8-isopropyl-5-methyl-6-oxo-5,6,7,8-tetrahydro-pteridin-2-ylamino)-benzenesulfonyl]-ethyl ester (130 mg; 0.269 mmol) was dissolved in 2.5 mL dimethylformamide and methylamine hydrochloride (54 mg; 0.807 mmol) was added. The reaction mixture was stirred at room temperature for 4 h. Then, the mixture was concentrated and dissolved in water and dichloromethane. The organic layer was dried with sodium sulphate then concentrated and crystallized from ether to yield 69 mg (0.165 mmol; 61% yield) of the desired product as a yellow solid.

LC-MS method: M
Retention time: 0.79 min
[M+H]=419

Some compounds which may be prepared by one of the methods of synthesis described above are hereinafter listed by way of example. All the melting points ($m_p$) are given in ° C.:.

In order to determine the inhibitory activity of the compounds on PI3Kγ, an in-vitro kinase assay is set up which is based on the transfer of the terminal γ-phosphate of ATP to phosphatidylinositol-4,5-bisphosphate ($PIP_2$). The enzyme activity used is the $G\beta_1\gamma_2$-His stimulated PI3Kγ. The expression and purification of $G\beta_1\gamma_2$-His and p101-GST/p110γ from Sf9-cells (*Spodoptera frugiperda* 9) has already been described (Maier et al., J. Biol. Chem. 1999 (274) 29311-29317).

The kinase assay is carried out in 96-well plates. Each well contains 10 μl of the compound to be tested which is dissolved in assay buffer (40 mM Hepes, pH 7.5, 100 mM NaCl, 1 mM EGTA, 1 mM β-glycerophosphate, 1 mM DTT, 7 mM $MgCl_2$ and 0.1% BSA; 6% DMSO). 30 μl of lipid vesicles containing 2 ng of PI3Kγ and 24 ng of $G\beta_1\gamma_2$-His is added in each case. The lipid vesicles in turn are generated by suspending a mixture of $PIP_2$ (0.7 μg/well), phosphatidylethanolamine (7.5 μg/well), phosphatidyl serine (7 μg/well), sphingomyelin (0.7 μg/well) and phosphatidyl choline (3.2 μg/well) in lipid buffer (assay buffer without DMSO) by ultrasound treatment. After the addition of the lipid vesicles the reaction is started by the addition of 20 μl reaction buffer (40 mM Hepes, pH 7.5, 100 mM NaCl, 1 mM EGTA, 1 mM β-glycerophosphate, 1 mM DTT, 7 mM $MgCl_2$ and 0.1% BSA; 1 μM ATP and 0.2 μCi [γ-$^{33}$P]-ATP). The reaction mixture is incubated in this way for 2 h and then stopped by the addition of 60 μl of Stop-buffer (40 mM Hepes, pH 7.5, 100 mM NaCl, 1 mM EGTA, 16 mM EDTA, 1 mM β-glycerophosphate, 1 mM DTT). 110 μl of the assay solution is then transferred to Multiscreen filter plates (Millipore, MAIPNOB). The plates are filtered by the application of vacuum and subsequently washed twice with 200 μl/well PBS. The plates are dried at 50° C., allowed to cool, supplemented with 50 μl/well Microscint 20 and counted using a TopCount (Perkin Elmer).

All the compounds shown have an $IC_{50}$ value of less than 800 nM in the test.

TABLE 1

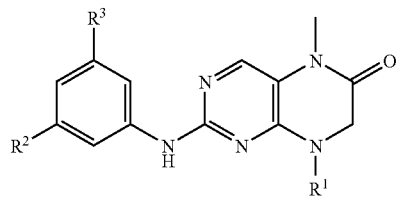

| Ex. | $R^1$ | $R^2$ | $R^3$ | HPLC-MS: Ret. Time; Method |
|---|---|---|---|---|
| 1 | iPr | O=S(=O)(CH₃)* | $CF_3$ | 7.78 (min); Gradient_2 |
| 2 | iPr | H₃C-S(=O)(=O)-N(H)-* | $CF_3$ | 6.44 (min); G |
| 3 | iPr | HN(CH₃)-C(=O)-* | $CF_3$ | 5.28 (min); G |
| 4 | iPr | H₂N-C(=O)-* | $CF_3$ | 5.97 (min); H |

TABLE 1-continued

| Ex. | R¹ | R² | R³ | HPLC-MS: Ret. Time; Method |
|---|---|---|---|---|
| 5 | iPr | (1-(2-oxoimidazolidin-1-yl)ethyl)carbamoyl | CF₃ | 6.42 (min); H2 |
| 6 | iPr | (2-(1-methylpyrrolidin-2-yl)ethyl)carbamoyl | CF₃ | 5.49 (min); I |
| 7 | iPr | (methylsulfonyl)methyl | CF₃ | 5.82 (min); I |
| 8 | iPr | 4-fluorophenylsulfonamido | SO₂NH₂ | 4.93 (min); A |
| 9 | iPr | pyridin-3-ylsulfonamido | SO₂NH₂ | 4.53 (min); A |
| 10 | iPr | (6-morpholinopyridin-3-yl)sulfonamido | SO₂NH₂ | 4.53 (min); C |

TABLE 1-continued

| Ex. | R¹ | R² | R³ | HPLC-MS: Ret. Time; Method |
|---|---|---|---|---|
| 11 | iPr | (cyclopentyl-pyrrolidinyl urea) | SO₂NH₂ | 3.87 (min); A |
| 12 | iPr | (cyclopentyl-pyrrolidinyl urea) | SO₂NH₂ | 3.95 (min); A |
| 13 | iPr | (pyridin-4-ylmethyl amide) | NHSO₂Me | 5.03 (min); Gradient_2 |
| 14 | iPr | (2-(pyridin-2-yl)ethyl amide) | NHSO₂Me | 5.18 (min); Gradient_2 |
| 15 | iPr | (cyclopentyl-pyrrolidinyl urea) | NHSO₂Me | 4.96 (min); Gradient_2 |
| 16 | iPr | (2-(dimethylamino)ethyl amide) | NHSO₂Me | 5.31 (min); Gradient_2 |
| 17 | iPr | (1-ethylpyrrolidin-2-ylmethyl amide) | NHSO₂Me | 5.04 (min); Gradient_2 |

TABLE 1-continued

[Structure: 3,5-disubstituted phenyl-NH group attached to a pteridinone core with N-methyl and N-R¹ substituents; phenyl bears R² and R³]

| Ex. | R¹ | R² | R³ | HPLC-MS: Ret. Time; Method |
|---|---|---|---|---|
| 18 | iPr | [1-methylpyrrolidin-3-yl-NH-C(=O)-*] | NHSO₂Me | 5.13 (min); Gradient_2 |
| 19 | iPr | [(CH₃)₂N-(CH₂)₄-NH-C(=O)-*] | NHSO₂Me | 2.68 (min); F |
| 20 | iPr | [(1-methylpyrrolidin-2-yl)-CH₂CH₂-NH-C(=O)-*] | NHSO₂Me | 3.69 (min); D |
| 21 | iPr | [(4-methyl-1H-imidazol-2-yl)-CH₂CH₂-NH-C(=O)-*] | NHSO₂Me | 4.31 (min); E |
| 22 | iPr | [(2-oxoimidazolidin-1-yl)-CH₂CH₂-NH-C(=O)-*] | NHSO₂Me | 4.53 (min); G |
| 23 | iPr | [H₃C-S(=O)₂-*] | SO₂Me | 7.07 (min); Gradient_2 |
| 24 | iPr | Cl | SO₂Me | 7.08 (min); Gradient_2 |
| 25 | iPr | Br | SO₂Me | 3.11 (min); Gradient |

TABLE 1-continued
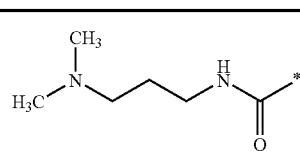
| Ex. | R¹ | R² | R³ | HPLC-MS: Ret. Time; Method |
|---|---|---|---|---|
| 26 | iPr | 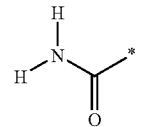 | SO$_2$Me | 3.12 (min); Gradient |
| 27 | iPr | 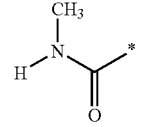 | SO$_2$Me | 3.23 (min); Gradient |
| 28 | iPr | 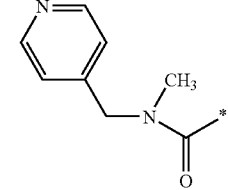 | SO$_2$Me | 5.08 (min); Gradient_2 |
| 29 | iPr | 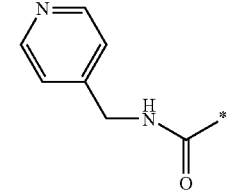 | SO$_2$Me | 5.15 (min); Gradient_2 |
| 30 | iPr | 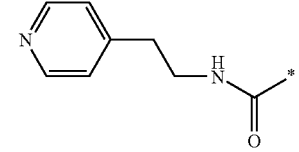 | SO$_2$Me | 5.23 (min); Gradient_2 |
| 31 | iPr | 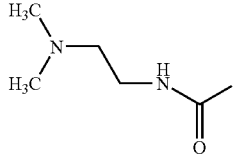 | SO$_2$Me | 5.1 (min); Gradient_2 |
| 32 | iPr |  | SO$_2$Me | 5.14 (min); Gradient_2 |

TABLE 1-continued

| Ex. | R¹ | R² | R³ | HPLC-MS: Ret. Time; Method |
|---|---|---|---|---|
| 33 | iPr | 4-(N-methylpiperidinyl)-NHC(O)-* | SO₂Me | 5.4 (min); Gradient_2 |
| 34 | iPr | (1-ethylpyrrolidin-2-yl)methyl-NHC(O)-* | SO₂Me | 5.11 (min); Gradient_2 |
| 35 | iPr | (1-methylpyrrolidin-3-yl)-NHC(O)-* | SO₂Me | 5.36 (min); Gradient_2 |
| 36 | iPr | 4-((4-methylpiperazin-1-yl)methyl)phenyl-NH- | SO₂Me | 3.52 (min); E |
| 37 | iPr | 2-(2-oxoimidazolidin-1-yl)ethyl-NHC(O)-* | SO₂Me | 4.21 (min); E |
| 38 | iPr | N≡C-* | SO₂Me | |
| 39 | iPr | CH₃S(O)₂-* | SO₂Me | 4.11 (min); H |

TABLE 1-continued
| Ex. | R¹ | R² | R³ | HPLC-MS: Ret. Time; Method |
|---|---|---|---|---|
| 40 | iPr |  | SO$_2$Me | 5.26 (min); Gradient |
| 41 | iPr | 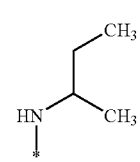 | SO$_2$Me | 5.34 (min); E |
| 42 | iPr | 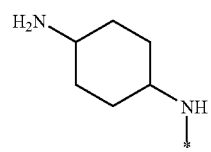 | SO$_2$Me | 2.18 (min); L |
| 43 | iPr | 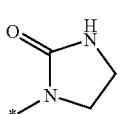 | SO$_2$Me | 4.3 (min); A |
| 44 | iPr | 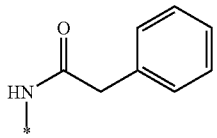 | SO$_2$Me | 6.23 (min); G |
| 45 | iPr | 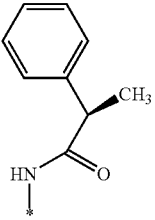 | SO$_2$Me | 5.97 (min); I |
| 46 | iPr | 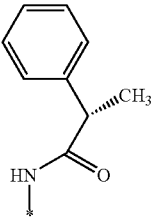 | SO$_2$Me | 5.97 (min); I |
| 47 | iPr |  | SO$_2$Me | 4.07 (min); C |

TABLE 1-continued
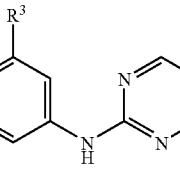
| Ex. | R[1] | R[2] | R[3] | HPLC-MS: Ret. Time; Method |
|---|---|---|---|---|
| 48 | iPr | 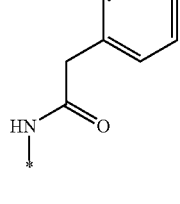 | SO$_2$Me | 5.03 (min); A |
| 49 | iPr | 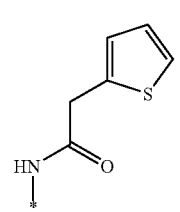 | SO$_2$Me | 5.03 (min); A |
| 50 | iPr | 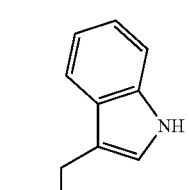 | SO$_2$Me | 5.11 (min); A |
| 51 | iPr | 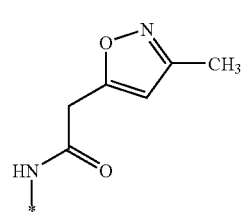 | SO$_2$Me | 4.7 (min); A |
| 52 | iPr | | SO$_2$Me | 5.23 (min); C |
| 53 | iPr | 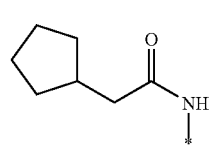 | SO$_2$Me | 3.7 (min); C |

TABLE 1-continued

[Structure 1: R³-substituted and R²-substituted phenyl connected via NH to a pteridinone core with N-methyl and N-R¹ groups]

| Ex. | R¹ | R² | R³ | HPLC-MS: Ret. Time; Method |
|---|---|---|---|---|
| 54 | iPr | [tetrazolyl-CH₂-C(O)NH-*] | SO₂Me | 6.9 (min); A |
| 55 | iPr | [2-methylphenyl-CH₂-C(O)NH-*] | SO₂Me | 6.43 (min); A |
| 56 | iPr | [6-chloropyridin-3-yl-CH₂-C(O)NH-*] | SO₂Me | 7 (min); A |
| 57 | iPr | [3-chlorophenyl-CH₂-C(O)NH-*] | SO₂Me | 6.93 (min); A |
| 58 | iPr | [3-methylphenyl-CH₂-C(O)NH-*] | SO₂Me | 7.21 (min); A |
| 59 | iPr | [cyclopentyl-CH₂CH₂-C(O)NH-*] | SO₂Me | 7.13 (min); A |

TABLE 1-continued
| Ex. | R¹ | R² | R³ | HPLC-MS: Ret. Time; Method |
|---|---|---|---|---|
| 60 | iPr | 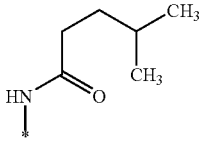 | SO₂Me | 6.9 (min); A |
| 61 | iPr | 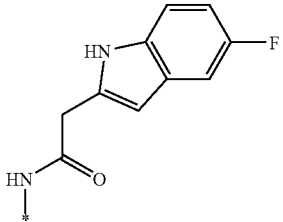 | SO₂Me | 6.6 (min); A |
| 62 | iPr | 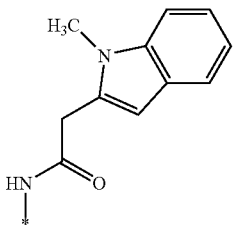 | SO₂Me | 6.83 (min); A |
| 63 | iPr | 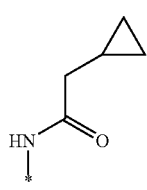 | SO₂Me | 6.32 (min); A |
| 64 | iPr | 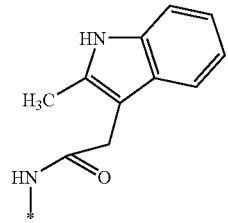 | SO₂Me | 6.63 (min); A |
| 65 | iPr |  | SO₂Me | 5.05 (min); C |

TABLE 1-continued
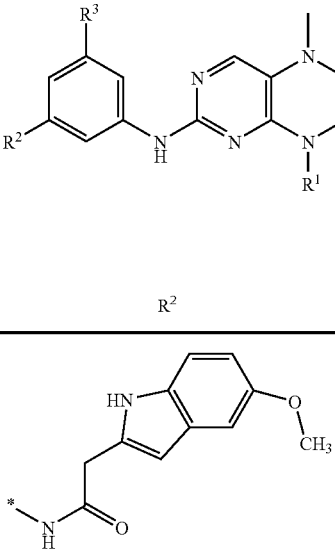
| Ex. | R¹ | R² | R³ | HPLC-MS: Ret. Time; Method |
|---|---|---|---|---|
| 66 | iPr | 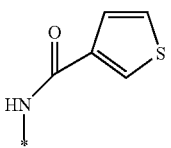 | SO₂Me | 6.48 (min); A |
| 67 | iPr | 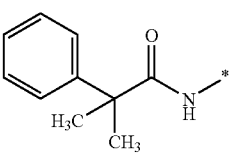 | SO₂Me | 7 (min); A |
| 68 | iPr | 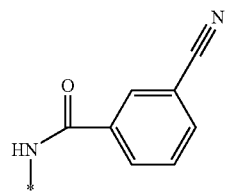 | SO₂Me | 6.52 (min); A |
| 69 | iPr | 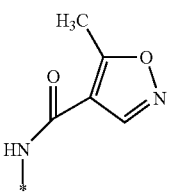 | SO₂Me | 4.13 (min); A |
| 70 | iPr | 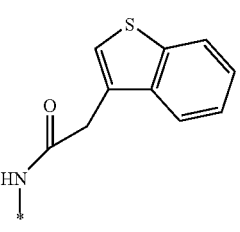 | SO₂Me | 5.76 (min); A |
| 71 | iPr |  | SO₂Me | 5.40 (min); M |

TABLE 1-continued
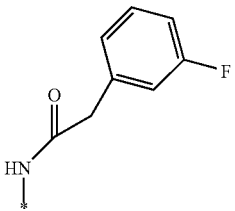
| Ex. | R¹ | R² | R³ | HPLC-MS: Ret. Time; Method |
|---|---|---|---|---|
| 72 | iPr | 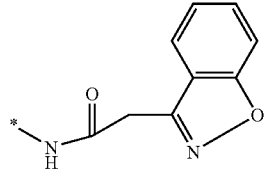 | SO₂Me | 5.41 (min); M |
| 73 | iPr | 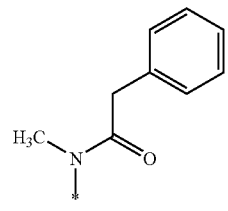 | SO₂Me | 5.54 (min); E |
| 74 | iPr | 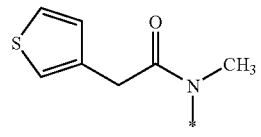 | SO₂Me | 6.42 (min); A |
| 75 | iPr | 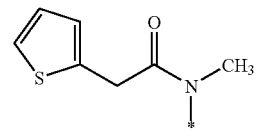 | SO₂Me | 6.45 (min); A |
| 76 | iPr | 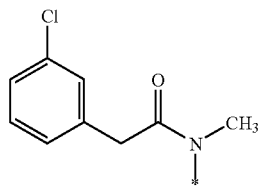 | SO₂Me | 5.6 (min); Purification Met. B |
| 77 | iPr | 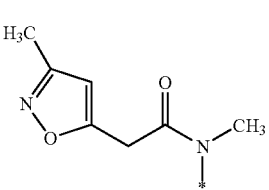 | SO₂Me | 5.9 (min); Purification Met. B |
| 78 | iPr |  | SO₂Me | 4.23 (min); C |

TABLE 1-continued
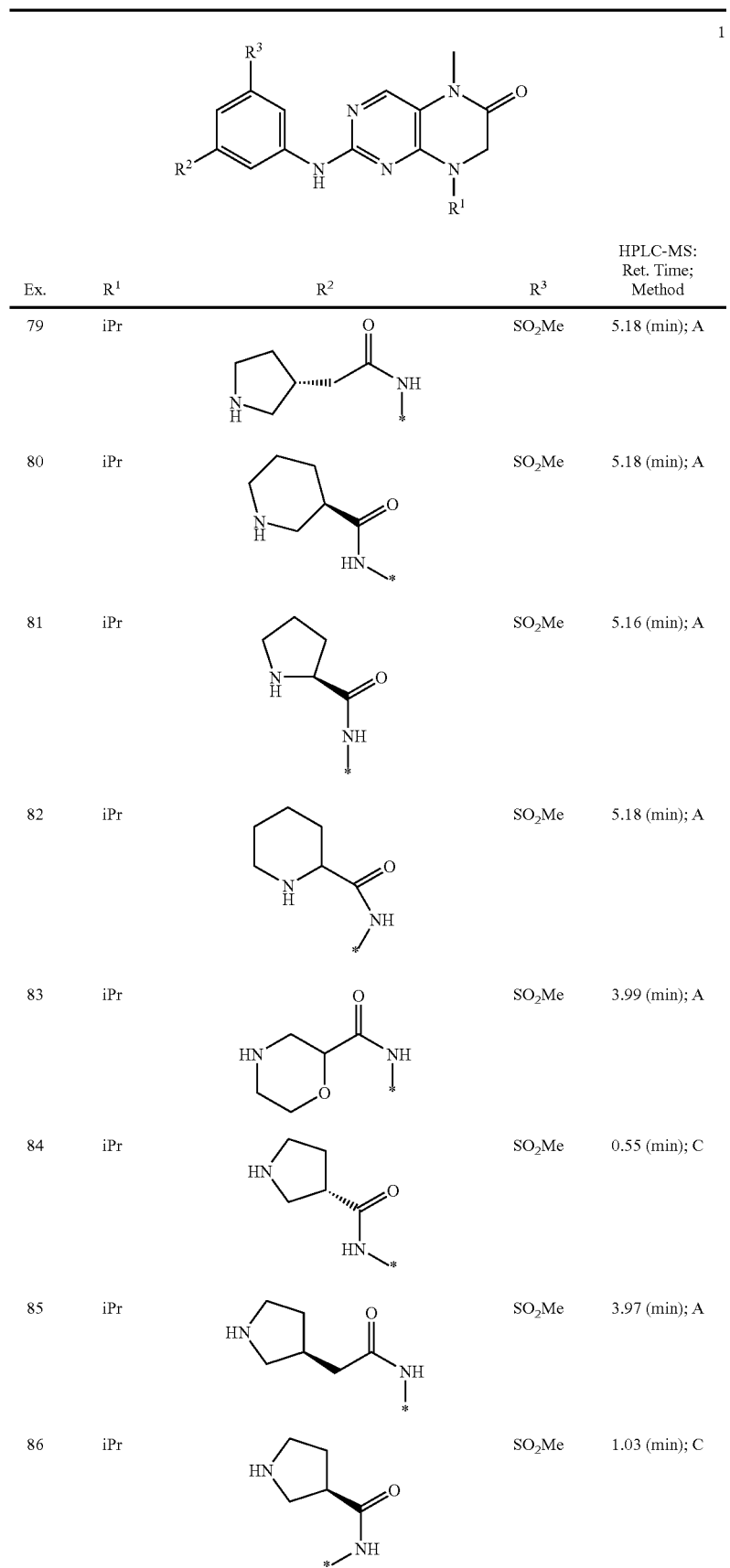
| Ex. | R¹ | R² | R³ | HPLC-MS: Ret. Time; Method |
|---|---|---|---|---|
| 79 | iPr | | SO$_2$Me | 5.18 (min); A |
| 80 | iPr | | SO$_2$Me | 5.18 (min); A |
| 81 | iPr | | SO$_2$Me | 5.16 (min); A |
| 82 | iPr | | SO$_2$Me | 5.18 (min); A |
| 83 | iPr | | SO$_2$Me | 3.99 (min); A |
| 84 | iPr | | SO$_2$Me | 0.55 (min); C |
| 85 | iPr | | SO$_2$Me | 3.97 (min); A |
| 86 | iPr | | SO$_2$Me | 1.03 (min); C |

TABLE 1-continued

| Ex. | R¹ | R² | R³ | HPLC-MS: Ret. Time; Method |
|---|---|---|---|---|
| 87 | iPr | (4-cyclopentyl-morpholine-2-carboxamide) | SO$_2$Me | 4.95 (min); A |
| 88 | iPr | (1-cyclopentyl-piperidine-3-carboxamide) | SO$_2$Me | 4.48 (min); A |
| 89 | iPr | (1-cyclopentyl-pyrrolidine-2-carboxamide) | SO$_2$Me | 5.1 (min); A |
| 90 | iPr | (1-cyclopentyl-piperidine-3-carboxamide) | SO$_2$Me | 4.44 (min); A |
| 91 | iPr | (1-cyclopentyl-pyrrolidin-3-yl-acetamide) | SO$_2$Me | 6.48 (min); A |
| 92 | iPr | (1-cyclopentyl-pyrrolidine-3-carboxamide) | SO$_2$Me | 5.58 (min); A |

TABLE 1-continued

| Ex. | R¹ | R² | R³ | HPLC-MS: Ret. Time; Method |
|---|---|---|---|---|
| 93 | iPr | 1-cyclopentylpyrrolidin-3-yl acetamide | SO₂Me | 5.69 (min); A |
| 94 | iPr | (phenyl)(amino)acetamide | SO₂Me | 5.59 (min); A |
| 95 | iPr | (phenyl)(amino)acetamide | SO₂Me | 4.77 (min); C |
| 96 | iPr | (cyclohexyl)(amino)acetamide | SO₂Me | 4.93 (min); C |
| 97 | iPr | methylaminocarbonylamino | SO₂Me | 3.57 (min); G |
| 98 | iPr | morpholine-4-carboxamide | SO₂Me | 4.83 (min); H |

TABLE 1-continued

[Structure 1: Core scaffold with R¹, R², R³ substituents on a pteridinone-aniline]

| Ex. | R¹ | R² | R³ | HPLC-MS: Ret. Time; Method |
|---|---|---|---|---|
| 99 | iPr | *-NH-C(O)-NH-CH₂CH₂CH₂-N(CH₃)₂ | SO₂Me | 3.45 (min); H |
| 100 | iPr | *-NH-C(O)-NH₂ | SO₂Me | 4.02 (min); H |
| 101 | iPr | *-NH-C(O)-NH-CH₂-cyclopropyl | SO₂Me | 8.41 (min); D |
| 102 | iPr | *-NH-C(O)-NH-CH₂-phenyl | SO₂Me | 9.02 (min); D |
| 103 | iPr | *-NH-C(O)-NH-CH₂CH₂-(2-oxoimidazolidin-1-yl) | SO₂Me | 6.13 (min); H |

TABLE 1-continued

|   |   |   |   | HPLC-MS: Ret. Time; |
|---|---|---|---|---|
| Ex. | R¹ | R² | R³ | Method |
| 104 | iPr | *-NH-C(O)-NH-(1-methylpiperidin-4-yl) | SO$_2$Me | 6.81 (min); D |
| 105 | iPr | *-NH-C(O)-NH-CH$_2$-(pyridin-4-yl) | SO$_2$Me | 7.75 (min); D |
| 106 | iPr | *-NH-C(O)-N(CH$_3$)-CH$_2$-(pyridin-4-yl) | SO$_2$Me | 8.01 (min); D |
| 107 | iPr | *-NH-C(O)-NH-CH$_2$CH$_2$-(5-ethyloxazol-2-yl) | SO$_2$Me | 6.06 (min); H2 |
| 108 | iPr | *-NH-C(O)-NH-CH$_2$CH$_2$-(pyrimidin-5-yl) | SO$_2$Me | 5.38 (min); B |
| 109 | iPr | *-NH-C(O)-NH-CH$_2$-((S)-tetrahydrofuran-2-yl) | SO$_2$Me | 5.77 (min); B |

TABLE 1-continued

[Structure 1: Core scaffold with R¹, R², R³ substituents on pteridinone system]

| Ex. | R¹ | R² | R³ | HPLC-MS: Ret. Time; Method |
|---|---|---|---|---|
| 110 | iPr | *-N(CH₃)-C(=O)-NH-phenyl | SO₂Me | 5.59 (min); I |
| 111 | iPr | *-N(CH₃)-C(=O)-NH-CH(CH₃)-phenyl (S) | SO₂Me | 5.65 (min); I |
| 112 | iPr | *-NH-C(=O)-NH-CH₂-(5-methyl-1H-pyrazol-3-yl) | SO₂Me | 5.78 (min); A |
| 113 | iPr | *-N(CH₃)-C(=O)-NH-CH₂-phenyl | SO₂Me | 5.2 min; Purification Met. B |
| 114 | iPr | *-NH-C(=O)-NH-(4-aminocyclohexyl) trans | SO₂Me | 4.14 (min); A |

TABLE 1-continued

| Ex. | R¹ | R² | R³ | HPLC-MS: Ret. Time; Method |
|---|---|---|---|---|
| 115 | iPr | (trans-4-dimethylamino-cyclohexyl)-NH-C(O)-NH-* | SO$_2$Me | 5.5 (min); A |
| 116 | iPr | (1-cyclopentylpyrrolidin-3-yl)-NH-C(O)-NH-* | SO$_2$Me | 4.87 (min); E |
| 117 | iPr | (pyrrolidin-2-yl)methyl-NH-C(O)-NH-* | SO$_2$Me | 3.1 (min); E |
| 118 | iPr | (pyrrolidin-3-yl)methyl-NH-C(O)-NH-* | SO$_2$Me | 3.05 (min); E |
| 119 | iPr | (pyrrolidin-3-yl)methyl-NH-C(O)-NH-* | SO$_2$Me | 3.05 (min); E |
| 120 | iPr | (1-cyclopentylpyrrolidin-2-yl)methyl-NH-C(O)-NH-* | SO$_2$Me | 4.89 (min); I |
| 121 | iPr | (pyrrolidin-2-yl)methyl-NH-C(O)-NH-* | SO$_2$Me | 4.28 (min); I |

TABLE 1-continued
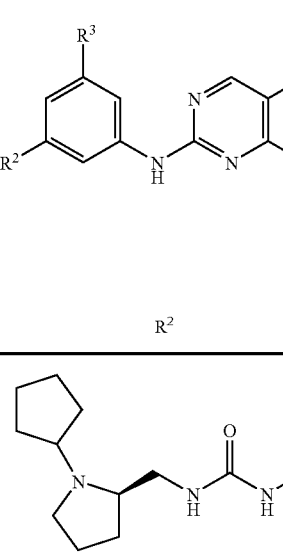
| Ex. | R¹ | R² | R³ | HPLC-MS: Ret. Time; Method |
|---|---|---|---|---|
| 122 | iPr | 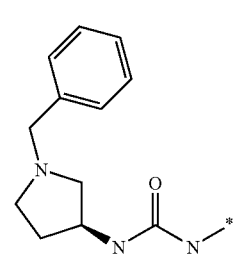 | SO$_2$Me | 4.84 (min); I |
| 123 | iPr | 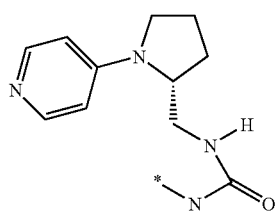 | SO$_2$Me | 4.66 (min); B |
| 124 | iPr | 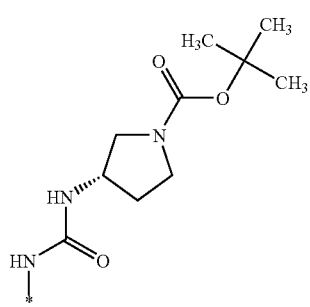 | SO$_2$Me | 6.85 (min); I |
| 125 | iPr | 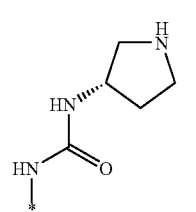 | SO$_2$Me | 7.17 (min); B |
| 126 | iPr |  | SO$_2$Me | 5.12 (min); B |

TABLE 1-continued
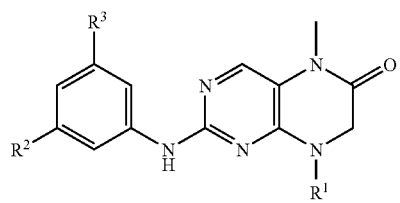
| Ex. | R¹ | R² | R³ | HPLC-MS: Ret. Time; Method |
|---|---|---|---|---|
| 127 | iPr | 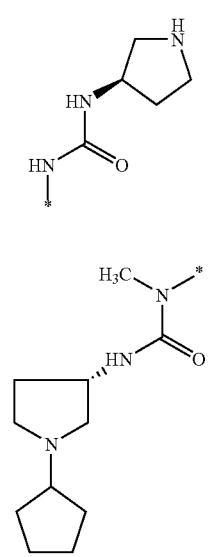 | SO₂Me | 5.12 (min); B |
| 128 | iPr | 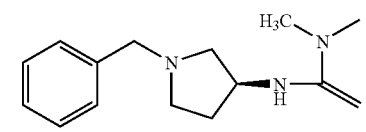 | SO₂Me | 4.21 (min); A |
| 129 | iPr | 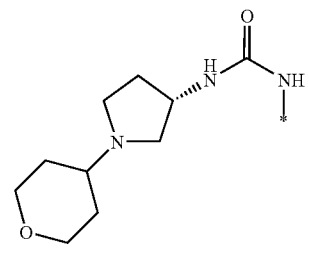 | SO₂Me | 4.33 (min); A |
| 130 | iPr | 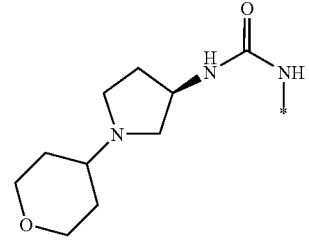 | SO₂Me | 5.31 (min); A |
| 131 | iPr |  | SO₂Me | 5.3 (min); A |

TABLE 1-continued
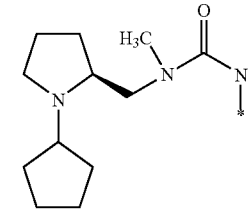
| Ex. | R¹ | R² | R³ | HPLC-MS: Ret. Time; Method |
|---|---|---|---|---|
| 132 | iPr | 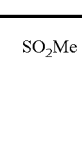 | SO₂Me | 5.85 (min); A |
| 133 | iPr | 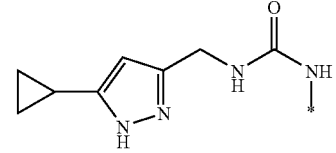 | SO₂Me | 6.02 (min); A |
| 134 | iPr |  | SO₂Me | 5.82 (min); A |
| 135 | iPr | 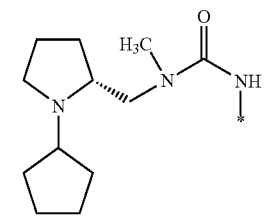 | SO₂Me | 5 (min); C |
| 136 | iPr | 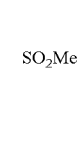 | SO₂Me | 3.41 (min); A |
| 137 | iPr | 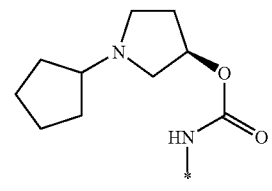 | SO₂Me | 6 (min); H |

TABLE 1-continued
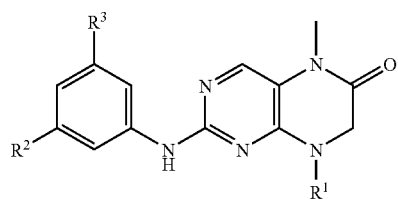
| Ex. | R¹ | R² | R³ | HPLC-MS: Ret. Time; Method |
|---|---|---|---|---|
| 138 | iPr | 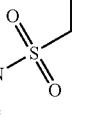 | SO₂Me | 7.88 (min); H2 |
| 139 | iPr | 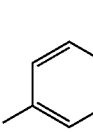 | SO₂Me | 6.73 (min); E |
| 140 | iPr | 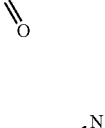 | SO₂Me | 3.88 (min); A |
| 141 | iPr | 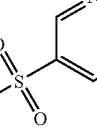 | SO₂Me | 6.65 (min); A |
| 142 | iPr | 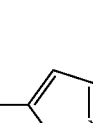 | H | |
| 143 | iPr | 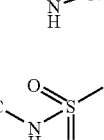 | H | |
| 144 | iPr | 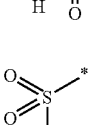 | H | 0.79 (min); M |

TABLE 1-continued

[Structure 1: Pteridinone core with R³ and R² on phenyl ring attached via NH to pyrimidine, N-methyl lactam, and R¹ on ring nitrogen]

| Ex. | R¹ | R² | R³ | HPLC-MS: Ret. Time; Method |
|---|---|---|---|---|
| 145 | iPr | *-S(O)₂-CH₂CH₂-NH-cyclobutyl | H | 0.92 (min); M |
| 146 | iPr | *-S(O)₂-CH₂CH₂-NH-CH(CH₃)₂ | H | 0.90 (min); M |
| 147 | Ph | *-S(O)₂-CH₂CH₂-piperidin-1-yl | H | 0.98 (min); M |
| 148 | Ph | *-S(O)₂-CH₂CH₂-NH-cyclopropyl | H | 0.96 (min); M |
| 149 | iPr | *-S(O)₂-CH₂CH₂-(4-methylpiperazin-1-yl) | H | 0.86 (min); M |

TABLE 1-continued

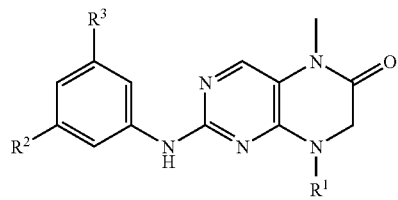

| Ex. | R¹ | R² | R³ | HPLC-MS: Ret. Time; Method |
|---|---|---|---|---|
| 150 | iPr | *-S(=O)₂-CH₂CH₂-OH | H | 0.83 (min); M |
| 151 | iPr | *-S(=O)₂-CH₂CH₂-morpholine | H | 0.85 (min); M |
| 152 | iPr | *-S(=O)₂-CH₂CH₂-N(CH₃)₂ | H | |
| 153 | Cyclohexyl | *-S(=O)₂-CH₂CH₃ | H | |
| 154 | iPr | *-S(=O)(=N-CH₃)- | H | |
| 155 | iPr | (piperazinone substituent) | H | 6.18 (min); 1E |

*point of attachment

Indications

It has been found that the compounds of formula 1 are characterised by a variety of possible applications in the therapeutic field. Particular mention should be made of those applications for which the compounds of formula 1 according to the invention are preferably used by virtue of their pharmaceutical activity as PI3-kinase modulators.

Generally speaking, these are diseases in whose pathology PI3-kinases are implicated, particularly inflammatory and allergic diseases. Particular mention should be made of inflammatory and allergic respiratory complaints, inflammatory diseases of the gastrointestinal tract, inflammatory diseases of the motor apparatus, inflammatory and allergic skin diseases, inflammatory eye diseases, diseases of the nasal mucosa, inflammatory or allergic ailments which involve autoimmune reactions or inflammation of the kidneys. The treatment may be symptomatic, adaptive, curative or preventative.

Respiratory complaints deserving special mention would be chronic and/or obstructive respiratory complaints. The compounds of formula 1 according to the invention may, by virtue of their pharmacological properties, bring about a reduction in Tissue damage
Inflammation of the airways
bronchial hyperreactivity
the process of reconstruction of the lung as a result of inflammation
worsening of the disease (progression).

The compounds according to the invention are particularly preferred for preparing a medicament for the treatment of chronic bronchitis, acute bronchitis, bronchitis caused by bacterial or viral infection or fungi or helminths, allergic bronchitis, toxic bronchitis, chronic obstructive bronchitis (COPD), asthma (intrinsic or allergic), pediatric asthma, bronchiectasis, allergic alveolitis, allergic or non-allergic rhinitis, chronic sinusitis, cystic fibrosis or mucoviscidosis, alpha-1-antitrypsin deficiency, cough, pulmonary emphysema, interstitial lung diseases such as e.g. pulmonary fibrosis, asbestosis and silicosis and alveolitis; hyperreactive airways, nasal polyps, pulmonary oedema such as e.g. toxic pulmonary oedema and ARDS/IRDS, pneumonitis of different origins, e.g. radiation-induced or by caused by aspiration or infectious pneumonitis, collagenoses such as lupus eryth, systemic sclerodermy, sarcoidosis or Boeck's disease.

The compounds of formula 1 are also suitable for the treatment of diseases of the skin, such as e.g. psoriasis, contact dermatitis, atopic dermatitis, alopecia greata (circular hair loss), erythema exsudativum multiforme (Stevens-Johnson Syndrome), dermatitis herpetiformis, sclerodermy, vitiligo, nettle rash (urticaria), lupus erythematodes, follicular and surface pyodermy, endogenous and exogenous acne, acne rosacea and other inflammatory or allergic or proliferative skin diseases.

Moreover, the compounds of formula 1 are suitable for therapeutic use in cases of inflammatory or allergic complaints which involve autoimmune reactions, such as e.g. inflammatory bowel diseases, e.g. Crohn's disease or ulcerative colitis; diseases of the arthritis type, such as e.g. rheumatoid or psoriatic arthritis, osteoarthritis, rheumatoid spondylitis and other arthritic conditions or multiple sclerosis.

The following general inflammatory or allergic diseases may also be mentioned, which can be treated with medicaments containing compounds of formula 1:

inflammation of the eye, such as e.g. conjunctivitis of various kinds, e.g. caused by infections with fungi or bacteria, allergic conjunctivitis, irritable conjunctivitis, drug-induced conjunctivitis, keratitis, uveitis diseases of the nasal mucosa, such as e.g. allergic rhinitis/sinusitis or nasal polyps inflammatory or allergic conditions, such as e.g. systemic lupus erythematodes, chronic hepatitis, kidney inflammations such as glomerulonephritis, interstitial nephritis or idiopathic nephrotic syndrome.

Other diseases which may be treated with a drug containing compounds of formula 1 on the basis of their pharmacological activity include toxic or septic shock syndrome, atherosclerosis, middle ear infections (otitis media), hypertrophy of the heart, cardiac insufficiency, stroke, ischaemic reperfusion injury or neurodegenerative diseases such as Parkinson's disease or Alzheimer's.

Combinations

The compounds of general formula 1 may be used on their own or combined with other active substances of formula 1 according to the invention. The compounds of general formula 1 may optionally also be combined with other pharmaceutically active substances. These include, in particular, betamimetics, anticholinergics, corticosteroids, PDE4-inhibitors, LTD4-antagonists, EGFR-inhibitors, dopamin-agonists, antiallergic agents, PAF-antagonists and PI3-kinase inhibitors, but also combinations of two or three active substances, i.e.:

Betamimetics with corticosteroids, PDE4-inhibitors, EGFR-inhibitors or LTD4-antagonists,
Anticholinergics with betamimetics, corticosteroids, PDE4-inhibitors, EGFR-inhibitors or LTD4-antagonists,
Corticosteroids with PDE4-inhibitors, EGFR-inhibitors or LTD4-antagonists
PDE4-inhibitors with EGFR-inhibitors or LTD4-antagonists
EGFR-inhibitors with LTD4-antagonists.

Examples of preferred betamimetics which may be mentioned include Albuterole, Arformoterole, Bambuterole, Bitolterole, Broxaterole, Carbuterole, Clenbuterole, Fenoterole, Formoterole, Hexoprenaline, Ibuterole, Isoetharine, Isoprenaline, Levosalbutamole, Mabuterole, Meluadrine, Metaproterenole, Orciprenaline, Pirbuterole, Procaterole, Reproterole, Rimiterole, Ritodrine, Salmefamole, Salmeterole, Soterenole, Sulphonterole, Terbutaline, Tiaramide, Tolubuterole, Zinterole, CHF-1035, HOKU-81, KUL-1248 and 3-(4-{6-[2-Hydroxy-2-(4-hydroxy-3-hydroxymethyl-phenyl)-ethylamino]-hexyloxy}-butyl)-benzyl-sulfonamide 5-[2-(5,6-Diethyl-indan-2-ylamino)-1-hydroxy-ethyl]-8-hydroxy-1H-quinolin-2-one 4-Hydroxy-7-[2-{[2-{[3-(2-phenylethoxy)propyl] sulphonyl}ethyl]-amino}ethyl]-2(3H)-benzothiazolone 1-(2-Fluoro-4-hydroxyphenyl)-2-[4-(1-benzimidazolyl)-2-methyl-2-butylamino]ethanole 1-[3-(4-Methoxybenzyl-amino)-4-hydroxyphenyl]-2-[4-(1-benzimidazolyl)-2-methyl-2-butylamino]ethanole 1-[2H-5-hydroxy-3-oxo-4H-1,4-benzoxazin-8-yl]-2-[3-(4-N,N-dimethylaminophenyl)-2-methyl-2-propylamino] ethanole 1-[2H-5-hydroxy-3-oxo-4H-1,4-benzoxazin-8-yl]-2-[3-(4-methoxyphenyl)-2-methyl-2-propylamino]ethanole 1-[2H-5-hydroxy-3-oxo-4H-1,4-benzoxazin-8-yl]-2-[3-(4-n-butyloxyphenyl)-2-methyl-2-propylamino]ethanole 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol 5-Hydroxy-8-(1-hydroxy-2-isopropylaminobutyl)-2H-1,4-benzoxazin-3-(4H)-one 1-(4-Amino-3-chloro-5-trifluormethylphenyl)-2-tert.-butylamino)ethanol 6-Hydroxy-8-{1-hydroxy-2-[2-(4-methoxy-phenyl)-1,1-dimethyl-ethylamino]-ethyl}-4H-benzo[1,4]oxazin-3-one 6-Hydroxy-8-{1-hydroxy-2-[2-(4-phenoxy-acetic acid ethylester)-1,1-dimethyl-ethylamino]-ethyl}-4H-benzo[1,4] oxazin-3-one 6-Hydroxy-8-{1-hydroxy-2-[2-(4-phenoxy-acetic acid)-1,1-dimethyl-ethylamino]-ethyl}-4H-benzo[1,4]oxazin-3-one 8-{2-[1,1-Dimethyl-2-(2,4,6-trimethylphenyl)-ethylamino]-1-hydroxy-ethyl}-6-hydroxy-4H-benzo[1,4]oxazin-3-one
6-Hydroxy-8-{1-hydroxy-2-[2-(4-hydroxy-phenyl)-1,1-dimethyl-ethylamino]-ethyl}-4H-benzo[1,4]oxazin-3-one
6-Hydroxy-8-{1-hydroxy-2-[2-(4-isopropyl-phenyl)-1,1-dimethyl-ethylamino]-ethyl}-4H-benzo[1,4]oxazin-3-one
8-{2-[2-(4-Ethyl-phenyl)-1,1-dimethyl-ethylamino]-1-hydroxy-ethyl}-6-hydroxy-4H-benzo[1,4]oxazin-3-one
8-{2-[2-(4-Ethoxy-phenyl)-1,1-dimethyl-ethylamino]-1-hydroxy-ethyl}-6-hydroxy-4H-benzo[1,4]oxazin-3-one
4-(4-{2-[2-Hydroxy-2-(6-hydroxy-3-oxo-3,4-dihydro-2H-benzo[1,4]oxazin-8-yl)-ethylamino]-2-methyl-propyl}-phenoxy)-butyric acid
8-{2-[2-(3,4-Difluor-phenyl)-1,1-dimethyl-ethylamino]-1-hydroxy-ethyl}-6-hydroxy-4H-benzo[1,4]oxazin-3-on
1-(4-Ethoxy-carbonylamino-3-cyano-5-fluorophenyl)-2-(tert.-butylamino)ethanol
2-Hydroxy-5-(1-hydroxy-2-{2-[4-(2-hydroxy-2-phenyl-ethylamino)-phenyl]-ethylamino}-ethyl)-benzaldehyde
N-[2-Hydroxy-5-(1-hydroxy-2-{2-[4-(2-hydroxy-2-phenyl-ethylamino)-phenyl]-ethylamino}-ethyl)-phenyl]-formamide
8-Hydroxy-5-(1-hydroxy-2-{2-[4-(6-methoxy-biphenyl-3-ylamino)-phenyl]-ethylamino}-ethyl)-1H-quinolin-2-one
8-Hydroxy-5-[1-hydroxy-2-(6-phenethylamino-hexylamino)-ethyl]-1H-quinolin-2-one
5-[2-(2-{4-[4-(2-Amino-2-methyl-propoxy)-phenylamino]-phenyl}-ethylamino)-1-hydroxy-ethyl]-8-hydroxy-1H-quinolin-2-one
[3-(4-{6-[2-Hydroxy-2-(4-hydroxy-3-hydroxymethyl-phenyl)-ethylamino]-hexyloxy}-butyl)-5-methyl-phenyl]-urea
4-(2-{6-[2-(2,6-Dichloro-benzyloxy)-ethoxy]-hexylamino}-1-hydroxy-ethyl)-2-hydroxymethyl-phenol
3-(4-{6-[2-Hydroxy-2-(4-hydroxy-3-hydroxymethyl-phenyl)-ethylamino]-hexyloxy}-butyl)-benzenesulfonamide
3-(3-{7-[2-Hydroxy-2-(4-hydroxy-3-hydroxymethyl-phenyl)-ethylamino]-heptyloxy}-propyl)-benzenesulfonamide
4-(2-{6-[4-(3-Cyclopentanesulfonyl-phenyl)-butoxy]-hexylamino}-1-hydroxy-ethyl)-2-hydroxymethyl-phenol
N-Adamantan-2-yl-2-(3-{2-[2-hydroxy-2-(4-hydroxy-3-hydroxymethyl-phenyl)-ethylamino]-propyl}-phenyl)-acetamide
(R,S)-4-(2-{[6-(2,2-Difluoro-4-phenylbutoxy)hexyl]amino}-1-hydroxy-ethyl)-2-(hydroxymethyl)phenol
(R,S)-4-(2-{[6-(2,2-Difluoro-2-phenylethoxy)hexyl]amino}-1-hydroxy-ethyl)-2-(hydroxymethyl)phenol
(R,S)-4-(2-{[4,4-Difluoro-6-(4-phenylbutoxy)hexyl]amino}-1-hydroxy-ethyl)-2-(hydroxymethyl)phenol
(R,S)-4-(2-{[6-(4,4-Difluoro-4-phenylbutoxy)hexyl]amino}-1-hydroxy-ethyl)-2-(hydroxymethyl)phenol
(R,S)-5-(2-{[6-(2,2-Difluoro-2-phenylethoxy)hexyl]amino}-1-hydroxy-ethyl)-8-hydroxyquinolin-2(1H)-one
(R,S)-[2-({6-[2,2-Difluoro-2-(3-methylphenyl)ethoxy]hexyl}amino)-1-hydroxyethyl]-2-(hydroxymethyl)phenol
4-(1R)-2-{[6-(2,2-Difluoro-2-phenylethoxy)hexyl]amino}-1-hydroxyethyl)-2-(hydroxymethyl)phenol
(R,S)-2-(Hydroxymethyl)-4-(1-hydroxy-2-{[4,4,5l5-tetrafluoro-6-(3-phenylpropoxy)hexyl]amino}ethyl)phenol
(R,S)-[5-(2-{[6-(2,2-Difluoro-2-phenylethoxy)hexyl]amino}-1-hydroxy-ethyl)-2-hydroxyphenyl]formamide
(R,S)-4-[2-({6-[2-(3-Bromophenyl)-2,2-difluoroethoxy]hexyl}amino)-1-hydroxyethyl]-2-(hydroxymethyl)phenol
(R,S)-N-[3-(1,1-Difluoro-2-{[6-({2-hydroxy-2-[4-hydroxy-3-(hydroxymethyl)-phenyl]ethyl}amino)hexyl]oxy}ethyl)phenyl]urea
3-[3-(1,1-difluoro-2-{[6-({2-hydroxy-2-[4-hydroxy-3-(hydroxymethyl)phenyl]ethyl}amino)hexyl]oxy}ethyl)phenyl]imidazolidine-2,4-dione
(R,S)-4-[2-({6-[2,2-difluoro-2-(3-methoxyphenyl)ethoxy]hexyl}amino)-1-hydroxyethyl]-2-(hydroxymethyl)phenol
5-((1R)-2-{[6-(2,2-difluoro-2-phenylethoxy)hexyl]amino}-1-hydroxyethyl)-8-hydroxyquinolin-2(1H)-one
4-((1R)-2-{[4,4-Difluoro-6-(4-phenylbutoxy)hexyl]amino}-1-hydroxy-ethyl)-2-(hydroxymethyl)phenol
(R,S)-4-(2-{[6-(3,3-Difluoro-3-phenylpropoxy)hexyl]amino}-1-hydroxy-ethyl)-2-(hydroxymethyl)phenol
(R,S)-(2-{[6-(2,2-Difluoro-2-phenylethoxy)-4,4-difluorohexyl]amino}-1-hydroxyethyl)-2-(hydroxymethyl)phenol
(R,S)-4-(2-{[6-(2,2-difluoro-3-phenylpropoxy)hexyl]amino}-1-hydroxy ethyl)-2-(hydroxymethyl)phenol optionally in racemic form, as enantiomers, diastereomeres or as pharmaceutically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

Examples of preferred anticholinergics which may be mentioned include Tiotropium salts, preferred the bromide salt, Oxitropium salts, preferred the bromide salt, Flutropium salts, preferred the bromide salt, Ipratropium salts, preferred the bromide salt, Glycopyrronium salts, preferred the bromide salt, Trospium salts, preferred the chloride salt, Tolterodin. From the above mentioned salts the pharmaceutically active part is the cation, possible anions are chloride, bromide, iodide, sulfate, phosphate, methansulfonate, nitrate, maleate, acetate, citrate, fumarate, tartrate, oxalate, succinate, benzoate or p-toluenesulfonate.

Furthermore
2,2-Diphenylpropion acid tropenolester-methobromide
2,2-Diphenylpropion acid scopinester-methobromide
2-Fluor-2,2-Diphenylacetic acid scopinester-methobromide
2-Fluor-2,2-Diphenylacetic acid tropenolester-methobromide
3,3',4,4'-Tetrafluorbenzil acid tropenolester-Methobromide
3,3',4,4'-Tetrafluorbenzil acid scopinester-Methobromide
4,4'-Difluorbenzil acid tropenolester-Methobromide
4,4'-Difluorbenzil acid scopinester-Methobromide
3,3'-Difluorbenzil acid tropenolester-Methobromide
3,3'-Difluorbenzil acid scopinester-Methobromide
9-Hydroxy-fluoren-9-carbon acid tropenolester-Methobromide
9-Fluor-fluoren-9-carbon acid tropenolester-Methobromide
9-Hydroxy-fluoren-9-carbon acid scopinester-Methobromide
9-Fluor-fluoren-9-carbon acid scopinester Methobromide
9-Methyl-fluoren-9-carbon acid tropenolesterMethobromide
9-Methyl-fluoren-9-carbon acid scopinesterMethobromide
Benzil acid cyclopropyltropinester-Methobromide
2,2-Diphenylpropion acid cyclopropyltropinester-Methobromide
9-Hydroxy-xanthen-9-carbon acid cyclopropyltropinester-Methobromide
9-Methyl-fluoren-9-carbon acid cyclopropyltropinester-Methobromide
9-Methyl-xanthen-9-carbon acid cyclopropyltropinester-Methobromide
9-Hydroxy-fluoren-9-carbon acid cyclopropyltropinester-Methobromide
4,4'-Difluorbenzil acid methylestercyclopropyltropinester-Methobromide 9-Hydroxy-xanthen-9-carbon acid tropenolester-Methobromide
9-Hydroxy-xanthen-9-carbon acid scopinester Methobromide
9-Methyl-xanthen-9-carbon acid tropenolester-Methobromide
9-Methyl-xanthen-9-carbon acid scopinesterMethobromide
9-Ethyl-xanthen-9-carbon acid tropenolester Methobromide
9-Difluormethyl-xanthen-9-carbon acid tropenolester-Methobromide
9-Hydroxymethyl-xanthen-9-carbon acid scopinester-Methobromide Examples of preferred corticosteroids which may be mentioned include Beclomethasone, Betamethasone, Budesonide, Butixocorte, Ciclesonide, Deflazacorte, Dexamethasone, Etiprednole, Flunisolide, Fluticasone, Loteprednole, Mometasone, Prednisolone, Prednisone, Rofleponide, Triamcinolone, RPR-106541, NS-126 and 6,9-Difluoro-17-[(2-furanylcarbonyl)oxy]-11-hydroxy-16-methyl-3-oxo-androsta-1,4-dien-17-carbothion acid (S)-fluoromethylester
6,9-Difluoro-11-hydroxy-16-methyl-3-oxo-17-propionyloxy-androsta-1,4-dien-17-carbothion acid (S)-(2-oxo-tetrahydro-furan-3S-yl)ester,
6α,9α-difluoro-11β-hydroxy-16α-methyl-3-oxo-17α-(2,2,3,3-tertamethylcyclopropylcarbonyl)oxy-androsta-1,4-diene-17β-carboxylic acid cyanomethyl ester optionally in racemic form, as enantiomers, diastereomeres or as pharmaceutically acceptable salts, solvates or hydrates. Examples for preferred salts and derivatives are alkali salts, i.e. sodium or potassium salts, sulfobenzoates, phosphates, isonicotinates, acetates, dichloroacetates, propionates, dihydrogenphosphates, palmitates, pivalates or furoates.

Examples of preferred PDE4-inhibitors which may be mentioned include Enprofylline, Theophylline, Roflumilaste, Ariflo (Cilomilast), Tofimilaste, Pumafentrine, Lirimilaste, Arofylline, Atizorame, Oglemilastum, D-4418, Bay-198004, BY343, CP-325,366, D-4396 (Sch-351591), AWD-12-281 (GW-842470), NCS-613, CDP-840, D-4418, PD-168787, T-440, T-2585, V-11294A, CI-1018, CDC-801, CDC-3052, D-22888, YM-58997, Z-15370 and N-(3,5-Dichloro-1-oxo-pyridin-4-yl)-4-difluoromethoxy-3-cyclopropylmethoxybenzamide
(−)p-[(4aR*,10bS*)-9-Ethoxy-1,2,3,4,4a,10b-hexahydro-8-methoxy-2-methylbenzo[s][1,6]naphthyridin-6-yl]-N,N-diisopropylbenzamide
(R)-(+)-1-(4-Bromobenzyl)-4-[(3-cyclopentyloxy)-4-methoxyphenyl]-2-pyrrolidon
3-(Cyclopentyloxy-4-methoxyphenyl)-1-(4-N'-[N-2-cyano-5-methyl-isothioureido]benzyl)-2-pyrrolidone
cis[4-Cyano-4-(3-cyclopentyloxy-4-methoxyphenyl)cyclohexan-1-carbon acid]
2-carbomethoxy-4-cyano-4-(3-cyclopropylmethoxy-4-difluoromethoxyphenyl)cyclohexan-1-one
cis[4-Cyano-4-(3-cyclopropylmethoxy-4-difluoromethoxyphenyl)cyclohexan-1-ol]
R)-(+)-Ethyl[4-(3-cyclopentyloxy-4-methoxyphenyl)pyrrolidin-2-yliden]acetate
(S)-(−)-Ethyl[4-(3-cyclopentyloxy-4-methoxyphenyl)pyrrolidin-2-yliden]acetate
9-Cyclopentyl-5,6-dihydro-7-ethyl-3-(2-thienyl)-9H-pyrazolo[3,4-c]-1,2,4-triazolo[4,3-a]pyridine
9-Cyclopentyl-5,6-dihydro-7-ethyl-3-(tert-butyl)-9H-pyrazolo[3,4-c]-1,2,4-triazolo[4,3-a]pyridine optionally in racemic form, as enantiomers, diastereomeres or as pharmaceutically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

Examples of preferred LTD4-antagonists which may be mentioned include Montelukaste, Pranlukaste, Zafirlukaste, MCC-847 (ZD-3523), MN-001, MEN-91507 (LM-1507), VUF-5078, VUF-K-8707, L-733321 and 1-(((R)-(3-(2-(6,7-Difluoro-2-quinolinyl)ethenyl)phenyl)-3-(2-(2-hydroxy-2-propyl)phenyl)thio)methylcyclopropane-acetic acid,
1-(((1(R)-3-(2-(2,3-Dichlorothieno[3,2-b]pyridin-5-yl)-(E)-ethenyl)phenyl)-3-(2-(1-hydroxy-1-methylethyl)phenyl)propyl)thio)methyl)cyclopropane acetic acid
[2-[[2-(4-tert-Butyl-2-thiazolyl)-5-benzofuranyl]oxymethyl]phenyl]acetic acid optionally in racemic form, as enantiomers, diastereomeres or as pharmaceutically to acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate. Further examples for optionally preferred salts and derivatives are alkali salts, i.e. sodium or potassium salts, sulfobenzoates, phosphates, isonicotinates, acetates, propionates, dihydrogenphosphates, palmitates, pivalates or furoates.

Examples of preferred EGFR-inhibitors which may be mentioned include Cetuximabe, Trastuzumabe, ABX-EGF, Mab ICR-62 and 4-[(3-Chlor-4-fluorphenyl)amino]-6-{[4-(morpholin-4-yl)-1-oxo-2-buten-1-yl]amino}-7-cyclopropylmethoxy-chinazoline
4-[(3-Chlor-4-fluorphenyl)amino]-6-{[4-(N,N-diethylamino)-1-oxo-2-buten-1-yl]amino}-7-cyclopropylmethoxy-chinazoline
4-[(3-Chlor-4-fluorphenyl)amino]-6-{[4-(N,N-dimethylamino)-1-oxo-2-buten-1-yl]amino}-7-cyclopropylmethoxy-chinazoline
4-[(R)-(1-Phenyl-ethyl)amino]-6-{[4-(morpholin-4-yl)-1-oxo-2-buten-1-yl]amino}-7-cyclopentyloxy-chinazoline
4-[(3-Chlor-4-fluor-phenyl)amino]-6-{[4-((R)-6-methyl-2-oxo-morpholin-4-yl)-1-oxo-2-buten-1-yl]amino}-7-cyclopropylmethoxy-chinazoline
4-[(3-Chlor-4-fluor-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-chinazoline
4-[(3-Chlor-4-fluor-phenyl)amino]-6-{[4-((R)-2-methoxymethyl-6-oxo-morpholin-4-yl)-1-oxo-2-buten-1-yl]amino}-7-cyclopropylmethoxy-chinazoline
4-[(3-Chlor-4-fluor-phenyl)amino]-6-[2-((S)-6-methyl-2-oxo-morpholin-4-yl)-ethoxy]-7-methoxy-chinazoline
4-[(3-Chlor-4-fluorphenyl)amino]-6-({4-[N-(2-methoxyethyl)-N-methyl-amino]-1-oxo-2-buten-1-yl}amino)-7-cyclopropylmethoxy-chinazoline
4-[(3-Chlor-4-fluorphenyl)amino]-6-{[4-(N,N-dimethylamino)-1-oxo-2-buten-1-yl]amino}-7-cyclopentyloxy-chinazoline
4-[(R)-(1-Phenyl-ethyl)amino]-6-{[4-(N,N-bis-(2-methoxyethyl)-amino)-1-oxo-2-buten-1-yl]amino}-7-cyclopropylmethoxy-chinazoline
4-[(R)-(1-Phenyl-ethyl)amino]-6-({4-[N-(2-methoxyethyl)-N-ethyl-amino]-1-oxo-2-buten-1-yl}amino)-7-cyclopropylmethoxy-chinazoline 4-[(R)-(1-Phenyl-ethyl)amino]-6-({4-[N-(2-methoxy-ethyl)-N-methyl-amino]-1-oxo-2-buten-1-yl}amino)-7-cyclopropylmethoxy-chinazoline 4-[(R)-(1-Phenyl-ethyl)amino]-6-({4-[N-(tetrahydropyran-4-yl)-N-methyl-amino]-1-oxo-2-buten-1-yl}amino)-7-cyclopropylmethoxy-chinazoline 4-[(3-Chlor-4-fluorphenyl)amino]-6-{[4-(N,N-dimethylamino)-1-oxo-2-buten-1-yl]amino}-7-((R)-tetrahydrofuran-3-yloxy)-chinazoline 4-[(3-Chlor-4-fluorphenyl)amino]-6-{[4-(N,N-dimethylamino)-1-oxo-2-buten-1-yl]amino}-7-((S)-tetrahydrofuran-3-yloxy)-chinazoline 4-[(3-Chlor-4-fluorphenyl)amino]-6-({4-[N-(2-methoxy-ethyl)-N-methyl-amino]-1-oxo-2-buten-1-yl}amino)-7-cyclopentyloxy-chinazoline 4-[(3-Chlor-4-fluorphenyl)amino]-6-{[4-(N-cyclopropyl-N-methyl-amino)-1-oxo-2-buten-1-yl]amino}-7-cyclopentyloxy-chinazoline 4-[(3-Chlor-4-fluorphenyl)amino]-6-{[4-(N,N-dimethylamino)-1-oxo-2-buten-1-yl]amino}-7-[(R)-(tetrahydrofuran-2-yl)methoxy]-chinazoline 4-[(3-Chlor-4-fluorphenyl)amino]-6-{[4-(N,N-dimethylamino)-1-oxo-2-buten-1-yl]amino}-7-[(S)-(tetrahydrofuran-2-yl)methoxy]-chinazoline 4-[(3-Ethinyl-phenyl)amino]-6,7-bis-(2-methoxy-ethoxy)-chinazoline 4-[(3-Chlor-4-fluorphenyl)amino]-7-[3-(morpholin-4-yl)-propyloxy]-6-[(vinylcarbonyl)amino]-chinazoline 4-[(R)-(1-Phenyl-ethyl)amino]-6-(4-hydroxy-phenyl)-7H-pyrrolo[2,3-d]pyrimidine 3-Cyano-4-[(3-chlor-4-fluorphenyl)amino]-6-{[4-(N,N-dimethylamino)-1-oxo-2-buten-1-yl]amino}-7-ethoxy-chinoline 4-{[3-Chlor-4-(3-fluor-benzyloxy)-phenyl]amino}-6-(5-{[(2-methansulfonyl-ethyl)amino]methyl}-furan-2-yl)chinazoline 4-[(R)-(1-Phenyl-ethyl)amino]-6-{[4-((R)-6-methyl-2-oxo-morpholin-4-yl)-1-oxo-2-buten-1-yl]amino}-7-methoxy-chinazoline 4-[(3-Chlor-4-fluorphenyl)amino]-6-{[4-(morpholin-4-yl)-1-oxo-2-buten-1-yl]amino}-7-[(tetrahydrofuran-2-yl)methoxy]-chinazoline 4-[(3-Chlor-4-fluorphenyl)amino]-6-({4-[N,N-bis-(2-methoxy-ethyl)-amino]-1-oxo-2-buten-1-yl}amino)-7-[(tetrahydrofuran-2-yl)methoxy]-chinazoline 4-[(3-Ethinyl-phenyl)amino]-6-{[4-(5,5-dimethyl-2-oxo-morpholin-4-yl)-1-oxo-2-buten-1-yl]amino}-chinazoline 4-[(3-Chlor-4-fluor-phenyl)amino]-6-[2-(2,2-dimethyl-6-oxo-morpholin-4-yl)-ethoxy]-7-methoxy-chinazoline 4-[(3-Chlor-4-fluor-phenyl)amino]-6-[2-(2,2-dimethyl-6-oxo-morpholin-4-yl)-ethoxy]-7-[(R)-(tetrahydrofuran-2-yl)methoxy]-chinazoline 4-[(3-Chlor-4-fluor-phenyl)amino]-7-[2-(2,2-dimethyl-6-oxo-morpholin-4-yl)-ethoxy]-6-[(S)-(tetrahydrofuran-2-yl)methoxy]-chinazoline 4-[(3-Chlor-4-fluor-phenyl)amino]-6-{2-[4-(2-oxo-morpholin-4-yl)-piperidin-1-yl]-ethoxy}-7-methoxy-chinazoline 4-[(3-Chlor-4-fluor-phenyl)amino]-6-[1-(tert.-butyloxycarbonyl)-piperidin-4-yloxy]-7-methoxy-chinazoline 4-[(3-Chlor-4-fluor-phenyl)amino]-6-(trans-4-amino-cyclohexan-1-yloxy)-7-methoxy-chinazoline 4-[(3-Chlor-4-fluor-phenyl)amino]-6-(trans-4-methansulfonylamino-cyclohexan-1-yloxy)-7-methoxy-chinazoline 4-[(3-Chlor-4-fluor-phenyl)amino]-6-(tetrahydropyran-3-yloxy)-7-methoxy-chinazoline 4-[(3-Chlor-4-fluor-phenyl)amino]-6-(1-methyl-piperidin-4-yloxy)-7-methoxy-chinazoline 4-[(3-Chlor-4-fluor-phenyl)amino]-6-{1-[(morpholin-4-yl)carbonyl]-piperidin-4-yloxy}-7-methoxy-chinazoline 4-[(3-Chlor-4-fluor-phenyl)amino]-6-{1-[(methoxymethyl)carbonyl]-piperidin-4-yloxy}-7-methoxy-chinazoline 4-[(3-Chlor-4-fluor-phenyl)amino]-6-(piperidin-3-yloxy)-7-methoxy-chinazoline 4-[(3-Chlor-4-fluor-phenyl)amino]-6-[1-(2-acetylamino-ethyl)-piperidin-4-yloxy]-7-methoxy-chinazoline 4-[(3-Chlor-4-fluor-phenyl)amino]-6-(tetrahydropyran-4-yloxy)-7-ethoxy-chinazoline 4-[(3-Chlor-4-fluor-phenyl)amino]-6-((S)-tetrahydrofuran-3-yloxy)-7-hydroxy-chinazoline 4-[(3-Chlor-4-fluor-phenyl)amino]-6-(tetrahydropyran-4-yloxy)-7-(2-methoxy-ethoxy)-chinazoline 4-[(3-Chlor-4-fluor-phenyl)amino]-6-{trans-4-[(dimethylamino)sulfonylamino]-cyclohexan-1-yloxy}-7-methoxy-chinazoline 4-[(3-Chlor-4-fluor-phenyl)amino]-6-{trans-4-[(morpholin-4-yl)carbonylamino]-cyclohexan-1-yloxy}-7-methoxy-chinazoline 4-[(3-Chlor-4-fluor-phenyl)amino]-6-{trans-4-[(morpholin-4-yl)sulfonylamino]-cyclohexan-1-yloxy}-7-methoxy-chinazoline 4-[(3-Chlor-4-fluor-phenyl)amino]-6-(tetrahydropyran-4-yloxy)-7-(2-acetylamino-ethoxy)-chinazoline 4-[(3-Chlor-4-fluor-phenyl)amino]-6-(tetrahydropyran-4-yloxy)-7-(2-methansulfonylamino-ethoxy)-chinazoline 4-[(3-Chlor-4-fluor-phenyl)amino]-6-{1-[(piperidin-1-yl)carbonyl]-piperidin-4-yloxy}-7-methoxy-chinazoline 4-[(3-Chlor-4-fluor-phenyl)amino]-6-(1-aminocarbonylmethyl-piperidin-4-yloxy)-7-methoxy-chinazoline 4-[(3-Chlor-4-fluor-phenyl)amino]-6-(cis-4-{N-[(tetrahydropyran-4-yl)carbonyl]-N-methyl-amino}-cyclohexan-1-yloxy)-7-methoxy-chinazoline 4-[(3-Chlor-4-fluor-phenyl)amino]-6-(cis-4-{N-[(morpholin-4-yl)carbonyl]-N-methyl-amino}-cyclohexan-1-yloxy)-7-methoxy-chinazoline 4-[(3-Chlor-4-fluor-phenyl)amino]-6-(cis-4-{N-[(morpholin-4-yl)sulfonyl]-N-methyl-amino}-cyclohexan-1-yloxy)-7-methoxy-chinazoline 4-[(3-Chlor-4-fluor-phenyl)amino]-6-(trans-4-ethansulfonylamino-cyclohexan-1-yloxy)-7-methoxy-chinazoline 4-[(3-Chlor-4-fluor-phenyl)amino]-6-(1-methansulfonyl-piperidin-4-yloxy)-7-ethoxy-chinazoline 4-[(3-Chlor-4-fluor-phenyl)amino]-6-(1-methansulfonyl-piperidin-4-yloxy)-7-(2-methoxy-ethoxy)-chinazoline 4-[(3-Chlor-4-fluor-phenyl)amino]-6-[1-(2-methoxy-acetyl)-piperidin-4-yloxy]-7-(2-methoxy-ethoxy)-chinazoline 4-[(3-Chlor-4-fluor-phenyl)amino]-6-(cis-4-acetylamino-cyclohexan-1-yloxy)-7-methoxy-chinazoline 4-[(3-Ethinyl-phenyl)amino]-6-[1-(tert.-butyloxycarbonyl)-piperidin-4-yloxy]-7-methoxy-chinazoline 4-[(3-Ethinyl-phenyl)amino]-6-(tetrahydropyran-4-yloxy]-7-methoxy-chinazoline 4-[(3-Chlor-4-fluor-phenyl)amino]-6-(cis-4-{N-[(piperidin-1-yl)carbonyl]-N-methyl-amino}-cyclohexan-1-yloxy)-7-methoxy-chinazoline 4-[(3-Chlor-4-fluor-phenyl)amino]-6-(cis-4-{N-[(4-methyl-piperazin-1-yl)carbonyl]-N-methyl-amino}-cyclohexan-1-yloxy)-7-methoxy-chinazoline 4-[(3-Chlor-4-fluor-phenyl)amino]-6-{cis-4-[(morpholin-4-yl)carbonylamino]-cyclohexan-1-yloxy}-7-methoxy-chinazoline 4-[(3-Chlor-4-fluor-phenyl)amino]-6-{1-[2-(2-oxopyrrolidin-1-yl)ethyl]-piperidin-4-yloxy}-7-methoxy-chinazoline 4-[(3-Chlor-4-fluor-phenyl)amino]-6-{1-[(morpholin-4-yl)carbonyl]-piperidin-4-yloxy}-7-(2-methoxy-ethoxy)-chinazoline
4-[(3-Ethinyl-phenyl)amino]-6-(1-acetyl-piperidin-4-yloxy)-7-methoxy-chinazoline
4-[(3-Ethinyl-phenyl)amino]-6-(1-methyl-piperidin-4-yloxy)-7-methoxy-chinazoline
4-[(3-Ethinyl-phenyl)amino]-6-(1-methansulfonyl-piperidin-4-yloxy)-7-methoxy-chinazoline
4-[(3-Chlor-4-fluor-phenyl)amino]-6-(1-methyl-piperidin-4-yloxy)-7(2-methoxy-ethoxy)-chinazoline
4-[(3-Chlor-4-fluor-phenyl)amino]-6-(1-isopropyloxycarbonyl-piperidin-4-yloxy)-7-methoxy-chinazoline
4-[(3-Chlor-4-fluor-phenyl)amino]-6-(cis-4-methylamino-cyclohexan-1-yloxy)-7-methoxy-chinazoline
4-[(3-Chlor-4-fluor-phenyl)amino]-6-{cis-4-[N-(2-methoxy-acetyl)-N-methyl-amino]-cyclohexan-1-yloxy}-7-methoxy-chinazoline
4-[(3-Ethinyl-phenyl)amino]-6-(piperidin-4-yloxy)-7-methoxy-chinazoline
4-[(3-Ethinyl-phenyl)amino]-6-[1-(2-methoxy-acetyl)-piperidin-4-yloxy]-7-methoxy-chinazoline
4-[(3-Ethinyl-phenyl)amino]-6-{1-[(morpholin-4-yl)carbonyl]-piperidin-4-yloxy}-7-methoxy-chinazoline
4-[(3-Chlor-4-fluor-phenyl)amino]-6-{1-[(cis-2,6-dimethyl-morpholin-4-yl)carbonyl]-piperidin-4-yloxy}-7-methoxy-chinazoline
4-[(3-Chlor-4-fluor-phenyl)amino]-6-{1-[(2-methyl-morpholin-4-yl)carbonyl]-piperidin-4-yloxy}-7-methoxy-chinazoline
4-[(3-Chlor-4-fluor-phenyl)amino]-6-{1-[(S,S)-(2-oxa-5-aza-bicyclo[2.2.1]hept-5-yl)carbonyl]-piperidin-4-yloxy}-7-methoxy-chinazoline
4-[(3-Chlor-4-fluor-phenyl)amino]-6-{1-[(N-methyl-N-2-methoxyethyl-amino)carbonyl]-piperidin-4-yloxy}-7-methoxy-chinazoline
4-[(3-Chlor-4-fluor-phenyl)amino]-6-(1-ethyl-piperidin-4-yloxy)-7-methoxy-chinazoline
4-[(3-Chlor-4-fluor-phenyl)amino]-6-{1-[(2-methoxyethyl)carbonyl]-piperidin-4-yloxy}-7-methoxy-chinazoline
4-[(3-Chlor-4-fluor-phenyl)amino]-6-{1-[(3-methoxypropyl-amino)-carbonyl]-piperidin-4-yloxy}-7-methoxy-chinazoline
4-[(3-Chlor-4-fluor-phenyl)amino]-6-[cis-4-(N-methansulfonyl-N-methyl-amino)-cyclohexan-1-yloxy]-7-methoxy-chinazoline
4-[(3-Chlor-4-fluor-phenyl)amino]-6-[cis-4-(N-acetyl-N-methyl-amino)-cyclohexan-1-yloxy]-7-methoxy-chinazoline
4-[(3-Chlor-4-fluor-phenyl)amino]-6-(trans-4-methylamino-cyclohexan-1-yloxy)-7-methoxy-chinazoline
4-[(3-Chlor-4-fluor-phenyl)amino]-6-[trans-4-(N-methansulfonyl-N-methyl-amino)-cyclohexan-1-yloxy]-7-methoxy-chinazoline
4-[(3-Chlor-4-fluor-phenyl)amino]-6-(trans-4-dimethylamino-cyclohexan-1-yloxy)-7-methoxy-chinazoline
4-[(3-Chlor-4-fluor-phenyl)amino]-6-(trans-4-{N-[(morpholin-4-yl)carbonyl]-N-methyl-amino}-cyclohexan-1-yloxy)-7-methoxy-chinazoline
4-[(3-Chlor-4-fluor-phenyl)amino]-6-[2-(2,2-dimethyl-6-oxo-morpholin-4-yl)-ethoxy]-7-[(S)-(tetrahydrofuran-2-yl)methoxy]-chinazoline
4-[(3-Chlor-4-fluor-phenyl)amino]-6-(1-methansulfonyl-piperidin-4-yloxy)-7-methoxy-chinazoline
4-[(3-Chlor-4-fluor-phenyl)amino]-6-(1-cyano-piperidin-4-yloxy)-7-methoxy-chinazoline optionally in racemic form, as enantiomers, diastereomeres or as pharmaceutically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

Examples of preferred dopamin antagonists which may be mentioned include Bromocriptine, Cabergoline, Alpha-Dihydroergocryptine, Lisuride, Pergolide, Pramipexole, Roxindole, Ropinirole, Talipexole, Terguride and Viozane, optionally in racemic form, as enantiomers, diastereomeres or as pharmaceutically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, to hydroacetate, hydrocitrate, hydrofumarate, hydrotartrate, hydrooxalate, hydrosuccinate, hydrobenzoate und hydro-p-toluenesulfonate.

Examples of preferred antiallergic agents which may be mentioned include Epinastine, Cetirizine, Azelastine, Fexofenadine, Levocabastine, Loratadine, Mizolastine, Ketotifene, Emedastine, Dimetindene, Clemastine, Bamipine, Cexchlorpheniramine, Pheniramine, Doxylamine, Chlorphenoxamine, Dimenhydrinate, Diphenhydramine, Promethazine, Ebastine, Desloratidine and Meclozine, optionally in racemic form, as enantiomers, diastereomeres or as pharmaceutically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate und hydro-p-toluenesulfonate.

Examples of preferred PAF antagonists which may be mentioned include
4-(2-Chlorphenyl)-9-methyl-2-[3(4-morpholinyl)-3-propanon-1-yl]-6H-thieno-[3,2-f]-[1,2,4]triazolo[4,3-a][1,4]diazepine
6-(2-Chlorphenyl)-8,9-dihydro-1-methyl-8-[(4-morpholinyl)carbonyl]-4H,7H-cyclo-penta-[4,5]thieno-[3,2-f][1,2,4]triazolo[4,3-a][1,4]diazepine optionally in racemic form, as enantiomers, diastereomeres or as pharmaceutically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

Formulations

The compounds according to the invention may be administered by oral, transdermal, inhalative, parenteral or sublingual route. The compounds according to the invention are present as active ingredients in conventional preparations, for example in compositions consisting essentially of an inert pharmaceutical carrier and an effective dose of the active substance, such as for example tablets, coated tablets, capsules, lozenges, powders, solutions, suspensions, emulsions, syrups, suppositories, transdermal systems etc. An effective dose of the compounds according to the invention is between 0.1 and 5000, preferably between 1 and 500, more preferably between 5-300 mg/dose for oral administration, and between 0.001 and 50, preferably between 0.1 and 10 mg/dose for intravenous. subcutaneous or intramuscular administration.

For inhalation, according to the invention, solutions containing 0.01 to 1.0, preferably 0.1 to 0.5% active substance are suitable. For administration by inhalation the use of powders, ethanolic or aqueous solutions is preferred. It is also possible to use the compounds according to the invention as a solution for infusion, preferably in a physiological saline or nutrient saline solution.

The compounds according to the invention may be used on their own or in conjunction with other active substances according to the invention, optionally also in conjunction with other pharmaceutically active substances. Suitable formulations include, for example, tablets, capsules, suppositories, solutions, syrups, emulsions or dispersible powders. Corresponding tablets may be obtained for example by mixing the active substance(s) with known excipients, for example inert diluents, such as calcium carbonate, calcium phosphate or lactose, disintegrants such as maize starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced to analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection are prepared in the usual way, e.g. with the addition of preservatives such as p-hydroxybenzoates, or stabilisers such as alkali metal salts of ethylenediamine tetraacetic acid, and transferred into injection vials or ampoules.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

A therapeutically effective daily dose is between 1 and 2000 mg, preferably 10-500 mg per adult.

The Examples which follow illustrate the present invention without restricting its scope:
Examples of Pharmaceutical Formulations

| A) | Tablets | per tablet |
|---|---|---|
| | active substance | 100 mg |
| | lactose | 140 mg |
| | maize starch | 240 mg |
| | polyvinylpyrrolidone | 15 mg |
| | magnesium stearate | 5 mg |
| | | 500 mg |

The finely ground active substance, lactose and some of the corn starch are mixed together. The mixture is screened, then moistened with a solution of polyvinylpyrrolidone in water, kneaded, granulated while wet and dried. The granulate, the rest of the corn starch and the magnesium stearate are screened and mixed together. The mixture is compressed to form tablets of a suitable shape and size.

| B) | Tablets | per tablet |
|---|---|---|
| | active substance | 80 mg |
| | corn starch | 190 mg |
| | lactose | 55 mg |
| | microcrystalline cellulose | 35 mg |
| | polyvinylpyrrolidone | 15 mg |
| | sodium-carboxymethyl starch | 23 mg |
| | magnesium stearate | 2 mg |
| | | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodium-carboxymethyl starch and the magnesium stearate are added and mixed in and the mixture is compressed to form tablets of a suitable size.

| C) | Coated tablets | per coated tablet |
|---|---|---|
| | Active substance | 5 mg |
| | Corn starch | 41.5 mg |
| | Lactose | 30 mg |
| | Polyvinylpyrrolidone | 3 mg |
| | Magnesium stearate | 0.5 mg |
| | | 80 mg |

The active substance, corn starch, lactose and polyvinylpyrrolidone are thoroughly mixed and moistened with water. The moist mass is pushed through a screen with a 1 mm mesh size, dried at about 45° C. and the granules are then passed through the same screen. After the magnesium stearate has been mixed in, convex tablet cores with a diameter of 6 mm are compressed in a tablet-making machine. The tablet cores thus produced are coated in a known manner with a covering consisting essentially of sugar and talc. The finished coated tablets are polished with wax

| D) | Capsules | per capsule |
|---|---|---|
| | Active substance | 50 mg |
| | Corn starch | 268.5 mg |
| | Magnesium stearate | 1.5 mg |
| | | 320 mg |

The substance and corn starch are mixed and moistened with water. The moist mass is screened and dried. The dry granules are screened and mixed with magnesium stearate. The finished mixture is packed into size 1 hard gelatine capsules.

| E) | Ampoule solution | |
|---|---|---|
| | active substance | 50 mg |
| | sodium chloride | 50 mg |
| | water for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

| F) | Suppositories | |
|---|---|---|
| | Active substance | 50 mg |
| | Solid fat | 1650 mg |
| | | 1700 mg |

The hard fat is melted. At 40° C. the ground active substance is homogeneously dispersed. It is cooled to 38° C. and poured into slightly chilled suppository moulds.

| G) | Oral suspension | |
|---|---|---|
| | active substance | 50 mg |
| | hydroxyethylcellulose | 50 mg |
| | sorbic acid | 5 mg |
| | sorbitol (70%) | 600 mg |
| | glycerol | 200 mg |
| | flavouring | 15 mg |
| | water ad | 5 ml |

Distilled water is heated to 70° C. Hydroxyethyl-cellulose is dissolved therein with stirring. After the addition of sorbitol solution and glycerol the mixture is cooled to ambient temperature. At ambient temperature, sorbic acid, flavouring and substance are added. To eliminate air from the suspension it is evacuated with stirring.

The invention claimed is:
1. A compound of formula 1

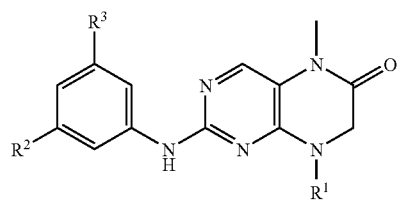

wherein:
$R^1$ denotes isopropyl;
$R^2$ denotes
(i) halogen or a group selected from -Q-CO—NR$^4$—C$_{6-14}$-aryl-Z$^1$—R$^5$, -Q-CO—NR$^4$—Z$^1$—R$^5$, -Q-NR$^4$—CO—X—R$^6$, -Q-NR$^4$—SO$_2$—X—R$^7$, -Q-NR$^4$—SO$_2$—Z$^1$—R$^7$, —Z$^1$—SO$_2$—R$^{16}$, —SO$_2$—Z$^1$—R$^{16}$, NO$_2$, and CONR$^4$R$^8$; or (ii) a group selected from the compounds of formula (III) or (IV),

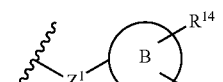

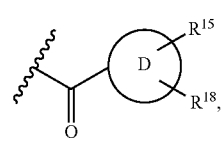

wherein
X denotes a bond or O;
Z$^1$ denotes a bond or C$_{1-3}$-alkylene;
Q denotes a bond;
R$^4$ denotes H;
R$^5$ denotes
  (i) NR$^4$R$^8$;
  (ii) an optionally substituted group selected from C$_{3-6}$-cycloalkyl, C$_{3-8}$-heterocycloalkyl and C$_{5-10}$-heteroaryl; or
  (iii) an optionally substituted group selected from

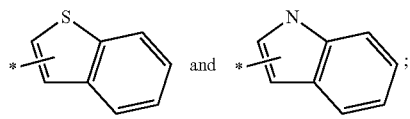

R$^6$ denotes C$_{1-5}$-alkyl;
R$^7$ denotes C$_{1-3}$-alkyl or phenyl;
R$^8$ denotes H;
R$^{14}$ and R$^{17}$ are each independently H, C$_{3-6}$-cycloalkyl, or =O;
R$^{15}$ and R$^{18}$ are each independently H or COOH;
R$^{16}$ denotes H or C$_{1-3}$-alkyl;
B denotes C$_{3-8}$-heterocycloalkyl;
D denotes C$_{6-14}$-aryl; or
R$^2$ denotes a group of formula (VIII) or (IX)

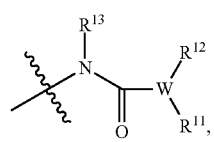

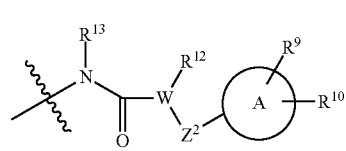

wherein
A denotes a group selected from C$_{3-6}$-cycloalkyl, C$_{6-14}$-aryl, C$_{3-8}$-heterocycloalkyl and C$_{5-10}$-heteroaryl;
W denotes N, C or O;
Z$^2$ denotes a bond or C$_1$-C$_4$-alkylene;

$R^9$ and $R^{10}$ each independently denote H, halogen, or a group selected from $C_{1-3}$-alkyl, $NR^4R^8$, =O, —$C_{1-2}$-alkylene-phenyl, —$NR^4$—$C_{1-2}$-alkylene-phenyl, —COO—$C_{1-5}$-alkyl, —CO-phenyl, —CO—$C_{1-5}$-alkyl, —CO—$Z^2$—$C_{3-6}$-cycloalkyl, $C_{6-14}$-aryl, $C_{5-10}$-heteroaryl, $C_{3-6}$-cycloalkyl and optionally substituted $C_{5-8}$-heterocycloalkyl $R^{11}$ denotes H or $C_{1-3}$-alkyl;

$R^{12}$ denotes H, $C_{1-4}$-alkyl, —$Z^2$—$NR^4R^8$ or —$Z^2$—O—$C_{1-3}$-alkyl; or $R^{11}$ and $R^{12}$ join to form an optionally substituted N-containing 5-to 6-membered heterocyclic ring;

$R^{13}$ denotes H or $C_{1-3}$-alkyl; or $R^{13}$ and $R^{12}$ join to form an N-containing 5- to 6-membered heterocyclic ring;

$R^3$ denotes H, $SO_2Me$, $SO_2NH_2$, —$NHSO_2Me$, or $CF_3$;

or a pharmaceutically acceptable salt, diastereomer, enantiomer, or racemate thereof.

2. A compound of formula 1 according to claim 1, wherein at least one of $R^9$ or $R^{10}$ denotes hydrogen.

3. A compound of formula 1 according to claim 1, wherein $R^2$ denotes
    (i) a group selected from —CO—$NR^4$—$C_{6-14}$-aryl-$Z^1$—$R^5$, —CO—$NR^4$—$Z^1$—$R^5$, —$NR^4$—CO—$Z^1$—$R^5$, —$NR^4$—CO—X—$R^6$, —$NR^4$—$SO_2$—$Z^1$—$R^7$, —$Z^1$—$SO_2$—$R^{16}$, $NO_2$ and $CONR^4R^8$; or
    (ii) a group of formula (III) or (IV)

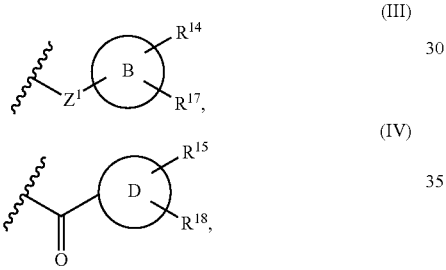

wherein
    X denotes a bond or O;
    $Z^1$ denotes a bond or $C_{1-3}$-alkylene;
    $R^4$ denotes H;
    $R^5$ denotes
        (i) $NR^4R^8$;
        (ii) an optionally substituted group selected from $C_{3-6}$-cycloalkyl, $C_{3-8}$-heterocycloalkyl and $C_{5-10}$-heteroaryl; or
        (iii) an optionally substituted group of formula (X)

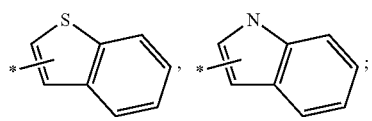

$R^6$ denotes $C_{1-5}$-alkyl;
$R^7$ denotes an optionally substituted group selected from $C_{1-3}$ alkyl and phenyl;

$R^8$ denotes H;
$R^{14}$ and $R^{17}$ are each independently H, $C_{3-6}$-cycloalkyl or =O;
$R^{15}$ and $R^{18}$ are each independently H or COOH; or
$R^{16}$ denotes H or $C_{1-3}$-alkyl;
    B denotes $C_{3-8}$-heterocycloalkyl;
    D denotes $C_{6-14}$-aryl;, or
$R^2$ denotes:
    a group of formula (VIII) or (IX)

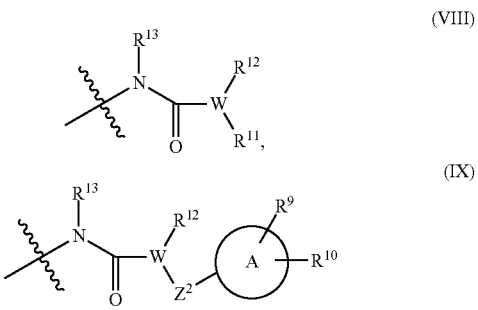

wherein
    A denotes a group selected from $C_{3-6}$-cycloalkyl, $C_{6-14}$-aryl, $C_{3-8}$-heterocycloalkyl and $C_{5-10}$-heteroaryl;
    W denotes N, C or O;
    $Z^2$ denotes a bond or $C_1$-$C_4$-alkylene;
    $R^9$ and $R^{10}$ are each independently H, halogen, or a group selected from $C_{1-3}$-alkyl, $NR^4R^8$, =O, —$C_{1-2}$-alkylene-phenyl, —$NR^4$—$C_{1-2}$-alkylene-phenyl, —COO—$C_{1-5}$-alkyl, —CO-phenyl, —CO—$C_{1-5}$-alkyl, —CO—$Z^2$—$C_{3-6}$-cycloalkyl, $C_{6-14}$-aryl, $C_{5-10}$-heteroaryl, $C_{3-6}$-cycloalkyl and optionally substituted $C_{5-8}$-heterocycloalkyl;
    $R^{11}$ denotes H, $C_{1-3}$-alkyl;
    $R^{12}$ denotes H, $C_{1-4}$-alkyl, —$Z^2$—$NR^4R^8$ or —$Z^2$—O—$C_{1-3}$-alkyl; or
    $R^{11}$ and $R^{12}$ join to form an optionally substituted N-containing 5-to 6-membered heterocyclic ring;
    $R^{13}$ denotes H or $C_{1-3}$-alkyl; or
    $R^{13}$ and $R^{12}$ join to form an N-containing 5- to 6-membered heterocyclic ring.

4. A pharmaceutical composition comprising the compound of formula 1 according to claim 1.

5. The pharmaceutical formulation according to claim 4 for administration by inhalation.

6. A compound of formula 1 according to claim 1, wherein $R^2$ denotes a group selected from —$NR^4$—$SO_2$—X—$R^7$, —$NR^4$—$SO_2$—$Z^1$—$R^7$, $Z^1$—$SO_2$—$R^{16}$ and —$SO_2$—$Z^1$—$R^{16}$.

* * * * *

UNITED STATES PATENT AND TRADEMARK OFFICE
CERTIFICATE OF CORRECTION

PATENT NO. : 8,410,100 B2
APPLICATION NO. : 12/524791
DATED : April 2, 2013
INVENTOR(S) : Giovannini et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 162 days.

Signed and Sealed this
Eighth Day of October, 2013

Teresa Stanek Rea
*Deputy Director of the United States Patent and Trademark Office*